US008847015B2

(12) United States Patent
Hatzfeld et al.

(10) Patent No.: US 8,847,015 B2
(45) Date of Patent: Sep. 30, 2014

(54) RICE PROMOTERS

(75) Inventors: Yves Hatzfeld, Lille (FR); Willem Broekaert, Dilbeek (BE)

(73) Assignee: Cropdesign N.V. (BE)

( * ) Notice: Subject to any disclaimer, the term of this patent is extended or adjusted under 35 U.S.C. 154(b) by 733 days.

(21) Appl. No.: 12/229,130

(22) Filed: Aug. 20, 2008

(65) Prior Publication Data

US 2009/0282587 A1 Nov. 12, 2009

Related U.S. Application Data

(62) Division of application No. 10/525,647, filed as application No. PCT/EP2004/050081 on Feb. 4, 2004, now Pat. No. 7,427,676.

(30) Foreign Application Priority Data

Feb. 4, 2003 (EP) .................................... 03075331

(51) Int. Cl.
*C12N 15/82* (2006.01)
*C12N 15/87* (2006.01)

(52) U.S. Cl.
CPC ........ *C12N 15/8234* (2013.01); *C12N 15/8216* (2013.01); *C12N 15/8222* (2013.01)
USPC ........ 800/287; 536/24.1; 800/278; 435/320.1

(58) Field of Classification Search
USPC ......................................................... 800/287
See application file for complete search history.

(56) References Cited

U.S. PATENT DOCUMENTS 7,365,185 B2 * 4/2008 Boukharov et al. .......... 536/24.1
2004/0016025 A1 1/2004 Budworth et al.

FOREIGN PATENT DOCUMENTS

WO WO 00/70067 11/2000
WO WO 03/000898 A1 1/2003

OTHER PUBLICATIONS

Evans et al 1992, Plant Mol. Biol. 20:1019-1028.*
Fourgoux-Nicol et al. (1999, Plant Molecular Biology 40 :857-872.*
Kim et al. 1994, Plant Molecular Biology 24: 105-117.*
Evans et al, 'Expression of the Pea . . . for $P_sMT_A$ function ' Plant Mol. Biol., 1992, 1019-1028, V. 20, Kluwer Academic Pub., Belgium.
Sasaki et al, Genbank Accession : AP004004. 2001.
Wu et al, Genbank Accession : AF541859. 2002.
Wu et al, 'Rice HMGB1 Protein . . . bends DNA efficiently' Archives of Biochemistry and Biophysics 411 (2003) 105-111 Academic Press.
Padgette et al, 'Development, Identification . . . Soybean Line', Crop Sci. 35: 1451-1461, Crop Science Society of America, Madison, WI USA 1995.
An et al , 'Transformation of Tobacco, . . . Ti Vector System' Plant Physiol. 81:301-305, 1986.
Kim et al, 'A 20 nucleotide upstream . . . promoter Activity' Plant Moleclar Biology 24: 105-117, 1994, Kluwer Academic Publishers, Belgium.
Fourgoux-Nicol et al, 'Isolation of rapseed genes . . . male gametophyte', Plant Molecular Biology 40-857-872, 1999, Kluwer Academic Publishers, Netherlands.
Jang et al, 'High Level and Ubiquitous . . . Transgenesis of Monocots', Plant Physiology. Aug. 2002, V129, 1473-1481 American Society of Plant Biologists.
Vibok et al, Endospeam Specific expression . . . in Transgenic rice (orysa Sativa L.) , Cereal Research Comm., V 27, No. 3, 1999 241-249.
Xu et al, 'Characterization of a rice gene . . . root-Specific proteins', Plant Molecular Biology 27, 237-248, 1995, Kluwer Academic Publishers, Belgium.
Sasaki et al. 2001 Genbank accession AP004004.
Wu et al. 2002, Genbank accession AF541859.
Padgette et al. 1995, Crop Sci. 35:1451-1461.
An et al. 1986 Plant Physiol 81:301-305.
Evans et al. 1992, Plant Mol. Biol. 20:1019-1028.
Kim et al., 1994, Plant Molecular Biol. 24:105-117.
Wu et al., "Rice HMGB1 protein . . . efficiently," Elsevier Science, Archives of Biochemistry and Physics 411 (2003) 105-111.
Jang et al., "High-level and Ubiquitous . . . " Plant Physiology Aug. 2002 vol. 129, pp. 1473-1481.
Vibok et al, "Endosperm specific expression . . . " Cereal Research Communications, vol. 27, No. 3, 1999.
Xu et al., "Characterization of a rice gene family . . . "Plant Molecular Biology vol. 27, pp. 237-248 (1995).
Fourgoux-Nicol et al. 1999, Plant Molecular Biology 40: 857-872.
Chung et al., "Studies on the promoter of the *Arabidopsis thaliana* cdc2a gene," FEBS Letters, 1995, vol. 362, pp. 215-219.

* cited by examiner

*Primary Examiner* — Li Zheng
(74) *Attorney, Agent, or Firm* — Barbara E. Johnson, Esq.

(57) ABSTRACT

The invention provides several promoters isolated from *Oryza sativa*, which promoters are capable of driving and/or regulating the expression of an operably linked nucleic acid in a plant. The expression patterns of the promoters according to the invention have been studied in *Oryza sativa* and some of the promoters displayed specific activity in particular cells, tissues or organs of the plant, while others displayed constitutive expression throughout substantially the whole plant. Some promoters showed weak expression, while others were strongly active.

3 Claims, 11 Drawing Sheets

PRO0110 RCc3

PRO0005 putative beta-amylase
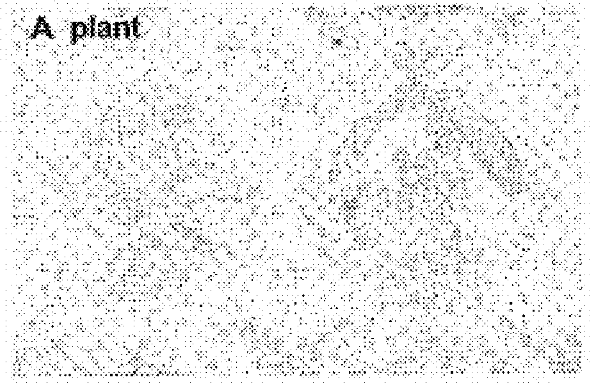
FIGURE 4
PRO0009 putative cellulose synthase
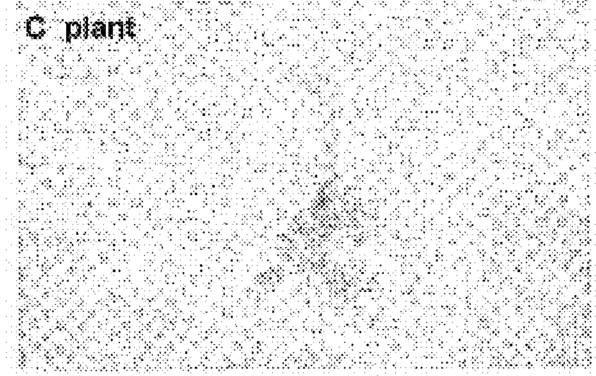
FIGURE 5
PRO058 proteinase inhibitor Rgpi9
A plant
FIGURE 6

PRO061 beta-expansion EXPB9

A

B

C

PRO0063 structural protein

A

B

A plant

OLD YOUNG SEED

PRO0081 putative caffeoyl CoA 3-O-methyltransferase

PRO0091 prolamin RP5

A

B

B plant

PRO0095 putative methionine aminopeptidase

PRO0111 uclacyanin 3-like protein

PRO0116 26S proteaseome regulatory particle non-ATPase subunit 11

PRO0117 putative 40S ribosomal protein

PRO0122 chlorophyll a/b binding protein precursor (Cab27)

PRO0123 putative protochlorophyllide reductase

PRO0133 chitinase Cht-3

PRO01151 WSI18

A Calli

B Seed

PRO0169 acquaporine

PRO0170 high mobility group protein

A

B

C

PRO0171 reversibly glycosylated protein RGP1

PRO0173 cytosolic MDH

PRO0175 RAB21

A Calli

PRO0177 Cdc2-1

SEQUENCE LISTING

```
<160> NUMBER OF SEQ ID NOS: 88

<210> SEQ ID NO 1
<211> LENGTH: 1264
<212> TYPE: DNA
<213> ORGANISM: Oryza sativa
<220> FEATURE:
<221> NAME/KEY: misc_feature
<223> OTHER INFORMATION: PRO0110 - RCc3

<400> SEQUENCE: 1

tcgacgctac tcaagtggtg ggaggccacc gcatgttcca acgaagcgcc aaagaaagcc      60

ttgcagactc taatgctatt agtcgcctag gatatttgga atgaaaggaa ccgcagagtt     120

tttcagcacc aagagcttcc ggtggctagt ctgatagcca aaattaagga ggatgccaaa     180

acatgggtct tggcgggcgc gaaacacctt gataggtggc ttacctttta acatgttcgg     240

gccaaaggcc ttgagacggt aaagttttct atttgcgctt gcgcatgtac aattttattc     300

ctctattcaa tgaaattggt ggctcactgg ttcattaaaa aaaaaagaat ctagcctgtt     360

cgggaagaag aggattttgt tcgtgagaga gagagagaga gagagagaga gagagagaga     420

gaaggaggag gaggattttc aggcttcgca ttgcccaacc tctgcttctg ttggcccaag     480

aagaatccca ggcgcccatg ggctggcagt ttaccacgga cctacctagc ctaccttagc     540

tatctaagcg ggccgaccta gtagccacgt gcctagtgta gattaaagtt gccgggccag     600

caggaagcca cgctgcaatg gcatcttccc ctgtccttcg cgtacgtgaa aacaaaccca     660

ggtaagctta gaatcttctt gcccgttgga ctgggacacc caccaatccc accatgcccc     720

gatattcctc cggtctcggt tcatgtgatg tcctctcttg tgtgatcacg gagcaagcat     780

tcttaaacgg caaaagaaaa tcaccaactt gctcacgcag tcacgctgca ccgcgcgaag     840

cgacgcccga taggccaaga tcgcgagata aaataacaac caatgatcat aaggaaacaa     900

gcccgcgatg tgtcgtgtgc agcaatcttg gtcatttgcg ggatcgagtg cttcacagct     960

aaccaaatat tcggccgatg atttaacaca ttatcagcgt agatgtacgt acgatttgtt    1020

aattaatcta cgagccttgc tagggcaggt gttctgccag ccaatccaga tcgccctcgt    1080

atgcacgctc acatgatggc agggcagggt tcacatgagc tctaacggtc gattaattaa    1140

tcccggggct cgactataaa tacctcccta atcccatgat caaaaccatc tcaagcagcc    1200
```

```
taatcatctc cagctgatca agagctctta attagctagc tagtgattag ctgcgcttgt   1260

gatc                                                                1264


<210> SEQ ID NO 2
<211> LENGTH: 1215
<212> TYPE: DNA
<213> ORGANISM: Oryza sativa
<220> FEATURE:
<221> NAME/KEY: misc_feature
<223> OTHER INFORMATION: PRO0005 - putative beta-amylase

<400> SEQUENCE: 2

cccgatttag tagaccacat tttggcatca aaccaaaata gaccctctcc cagaatttgt     60

aaatggcttt gtggttcgtg atatcactga acctgctggg tgaataaagt aaaaaaaaaa    120

acccataaat tggccttctg caagatctcg tcgtcttgcc caaactatag ccttcgatct    180

ttccatcagg accgcatggg gggagagcag gggcaagtat gaaatggagt tcagattcag    240

attctagaac agtctgaaca tgcgacgacg acgatggcga tgtatctgaa caatctggtc    300

ctctccctct cctcccgggc gggcttccac gcggctgagt ttcaggctcc caatctgcag    360

ctcctcccag aaccttactc tgattgattg gttcatcgtt tccatggctc caatgaatgc    420

aacgtgttgt tcagattttc tgaatcttgt tctcaatccg gagtacgtgc tgtagcagca    480

gcaatctgtc cctgatctga gaattttaga cactcgtaga ttcgctgatc aatcattccg    540

tcccttcgag tggtctagat tgagcttaat catcctgcta ctcgaatcaa atcttcagca    600

agtgagagct agataattca gaagaaatca acatattctt cgcgaaaaaa agaaataacc    660

gatgaaacca cggtaattag gttcttcgaa tcaccgggag agtaggaaaa aacgagctaa    720

aatcccacat aggaggaaac ggttaaaaac ggccactccg cgtctccgcc gcgagactag    780

ctctcgccag tccacgtagc ccaatccaca accgccacgt gctccgacaa tcccgcccgt    840

ccatcgccgc ggccccggcc tcatctcgac cactcgtttc ctcccttcac accagccacg    900

tggcactctc tcgagagctc ccgcccgcct atataaactt gttcgcgctc ggctcctcct    960

cctcatcgac ctccacccca cattgaataa ttatttttaa taattttagt ttttttttg    1020

gctttagata tattcccaat ccccaacctc ccaataatcc gatctctccc agttctgttc   1080

ggatcaaggc tgtgtcgatc gcaaaaaaga aaaaaaaaac aatttccttt tggggtggtt   1140

catctgttga tcacttcttt gtttcccgcg ttttgttggg gattcgattt tcgggttaag   1200

attttctaca cgacc                                                    1215


<210> SEQ ID NO 3
<211> LENGTH: 1038
<212> TYPE: DNA
<213> ORGANISM: Oryza sativa
<220> FEATURE:
<221> NAME/KEY: misc_feature
<223> OTHER INFORMATION: PRO0009 - putative cellulose synthase

<400> SEQUENCE: 3

gccatcgagt ggtgtgccga taccggcgcc tgttctttac agcctcagct agtgttgttg     60

tccgaggcaa tttttccgac ctattgtgtt gctttcctct ctgatagctt atggtaaaag    120

atacaaagat gttgaggagt ttgtacgcca cttaattttg ctcgtaacat acattgacaa    180

tcaagaggag ccatggcatt gcgatctgct tacacggcat attcttactg gatggtgtac    240

actacttacc ctttttaatg caagcatcaa tccattgctt ttctcactgc acacctgatt    300
```

```
cgtactgaaa acgtgaaaca taaaaaaaaa acaaaaatct agctgatgtt ggctctcggg    360

gcctcgagtc tagtttgtcc tagatggcta acctgatatg tgttggtcac gctcacgttt    420

gaaccgagaa agagtgtgtg tgtgtgtgtg tcggcgtgct gctacaccag agcctccctg    480

aatcgcaatg cgtgttaacg ccagcatcgc aggatttcat ctcacttgac aggttcagat    540

ggccttcctc ctaccgtctg ccatttatac acgcagtgac ttaacgctta cacgagccgg    600

atggcccgga tctcccccct gcaccatctc accagaaaaa cggtgaggcg tcaccgcaac    660

ccacccacca aacacatcca cgtcccttca ccgttggcct tcgattttgc ttcagctgca    720

ctacgacccc tccaacacat ttccctcgcg tctcgttgcg atctcacctt acgacgatct    780

cgttccagca gcagcagcat cggcagcggc ggcttgcttc cgaagcgagc aatgcatggc    840

gcgcgcggcc gcgtgcgtgc gtgccttggc ttgcgctcta atcaaaccgg gacgccccaa    900

ctcacggttg gtgcgggacg ccaccccgcc accttaccgc ccccgcctcc ctgcatctga    960

tcatcaacca gctgctatat cacctagcta gccgccgcct cctcctcgcc caccaacgtc   1020

gcttccccgg cacctcac                                                 1038


<210> SEQ ID NO 4
<211> LENGTH: 1301
<212> TYPE: DNA
<213> ORGANISM: Oryza sativa
<220> FEATURE:
<221> NAME/KEY: misc_feature
<223> OTHER INFORMATION: PRO0058 - proteinase inhibitor Rgpi9

<400> SEQUENCE: 4

tctcttctga agctgaagcc ctgcgaaata ggcctttaaa cgctttaagg ttactggatg     60

atcatatcgg cgtaagaccg gtttaaacat ggtttcgctt tgtgaatcca atgtgagtca    120

cgacgtgaca catggcacgt ccttggagct ttagacatat cgaatctgag cactggagtg    180

gccgagtggg tgagcggcca aatccgtttt agacagatcg cactgacacg atgttgatca    240

ttgatactaa taccatttta tcaagcagta gtgttgaaaa aaaaacttat gttctcttca    300

actgtgagat ttcatcccgt ttcaagatga acaagccatg catgtgagat gtgaacagaa    360

ggcagaagac agtggaaaga caggacaaat aagtgaagag ggatcaaatc aatgggcctg    420

acggtttctg aaagttgaca tggaaatcgc cggtgatcac cggtttatac gttatttaaa    480

tctgcgattt ccactttcgt ttgctttcgg ggttccaatt tgagtcacgc acatattctt    540

catcgtgctt tggatctcag caccgtagta acttttggac aaattgcatt cgccgacact    600

aataacatgt tctttttatg ctgctttaca tatactgctt atccacaccc aatcccatgt    660

tcatatatta tgagatggag ggagtaaact ttgttaacag caacattttt tatattaaag    720

catcaactaa ttaaagcaca agatacgcat gttatctcaa taaatcttcc agtgcatgta    780

taaagaagat gtcgccgcta acttagataa tttttgtgac ttttatcctg gccggcataa    840

ttaattcttc cggaaattaa aagctagttt ttccatattc atcagtacag acaagacagc    900

atagtaagcg aagcatacct gacgtgttag ctcattgtaa ctcgatctgg aacactcgat    960

gctagataca gacagacact cctcgtgatg aacgttagca tttagcaaca tacggtgata   1020

aagcagctgg ggatcgatcc atccatccat cgtctttaca cgtacttacc ttgctaaccg   1080

cactgtcgac tcttgcatgt ttgcatgtaa tccaaatgga ccccacgtgg aacatgctca   1140

cagtgctttg cagctgcttt ccaaaatgct ttctttcact tcttccattc ctctgtccac   1200

aaaaaaagta gtgtgttctt gagcctatat aagagagggt cacacgctcc agtcgactca   1260
```

ccatcgatcc atctgacggt tagttccaag ggaaagaaga a 1301

<210> SEQ ID NO 5
<211> LENGTH: 1243
<212> TYPE: DNA
<213> ORGANISM: Oryza sativa
<220> FEATURE:
<221> NAME/KEY: misc_feature
<223> OTHER INFORMATION: PRO0061 - beta-expansin EXPB9

<400> SEQUENCE: 5
aaaaccaccg agggacctga tctgcaccgg ttttgatagt tgagggaccc gttgtgtctg 60
gttttccgat cgagggacga aaatcggatt cggtgtaaag ttaagggacc tcagatgaac 120
ttattccgga gcatgattgg gaagggagga cataaggccc atgtcgcatg tgtttggacg 180
gtccagatct ccagatcact cagcaggatc ggccgcgttc gcgtagcacc cgcggtttga 240
ttcggcttcc cgcaaggcgg cggccggtgg ccgtgccgcc gtagcttccg ccggaagcga 300
gcacgccgcc gccgccgacc cggctctgcg tttgcaccgc cttgcacgcg atacatcggg 360
atagatagct actactctct ccgtttcaca atgtaaatca ttctactatt ttccacattc 420
atattgatgt taatgaatat agacatatat atctatttag attcattaac atcaatatga 480
atgtaggaaa tgctagaatg acttacattg tgaattgtga aatggacgaa gtacctacga 540
tggatggatg caggatcatg aaagaattaa tgcaagatcg tatctgccgc atgcaaaatc 600
ttactaattg cgctgcatat atgcatgaca gcctgcatgc gggcgtgtaa gcgtgttcat 660
ccattaggaa gtaaccttgt cattacttat accagtacta catactatat agtattgatt 720
tcatgagcaa atctacaaaa ctggaaagca ataaggaata cgggactgga aaagactcaa 780
cattaatcac caaatatttc gccttctcca gcagaatata tatctctcca tcttgatcac 840
tgtacacact gacagtgtac gcataaacgc agcagccagc ttaactgtcg tctcaccgtc 900
gcacactggc cttccatctc aggctagctt tctcagccac ccatcgtaca tgtcaactcg 960
gcgcgcgcac aggcacaaat tacgtacaaa acgcatgacc aaatcaaaac caccggagaa 1020
gaatcgctcc cgcgcgcggc ggcggcgcgc acgtacgaat gcacgcacgc acgcccaacc 1080
ccacgacacg atcgcgcgcg acgccggcga caccggccat ccacccgcgc cctcacctcg 1140
ccgactataa atacgtaggc atctgcttga tcttgtcatc catctcacca ccaaaaaaaa 1200
aggaaaaaaa aacaaaacac accaagccaa ataaaagcga caa 1243

<210> SEQ ID NO 6
<211> LENGTH: 1019
<212> TYPE: DNA
<213> ORGANISM: Oryza sativa
<220> FEATURE:
<221> NAME/KEY: misc_feature
<223> OTHER INFORMATION: PRO0063 - structural protein

<400> SEQUENCE: 6
cctagctata tgcagaggtt gacaggttgt ctcttagatc gattaataat atcacattga 60
tgcaattaat tatctgagat caataaagtt tttctttatg ttaaattaat atcagtaata 120
gatgctaagt ccttcattag tagtatccca catttaatca cagttggaca cacaaaaaaa 180
aaggcaatgc cattaatatg ccatctctct tgttttccat tgcctaccaa gtgccatatg 240
atatcatcat caggcacacc aatccataac tagttcatta gagcaagttt aataatagag 300
ctaactataa gcttataatt tatattggag taaacatgta tagtaaatga gctataaggt 360
tatttctttt tttctcctcc tctctctatc tcttacctat atatttaatg tatttgtctt 420

```
gaagtatgtg aatagctagc tcttgtatga gagccaatcc tctgcatttt ttaaattctc    480

tttcctccac ataagcatat agttggctta tagcctgcta ttatacttgg tcttagtaca    540

ctaacccccc ttacatgcaa tgcaagctgt ctaattaaaa gggtttcaca acattttgaa    600

tgccactact agctcccaac cacaaccaca gatctagcta gggtttgttc atttctctcc    660

tctctcctcc tcctcctttc cgttgtgcca attcatccaa agtcattgag agccatacta    720

ctccatatca tattactcct acatgtgtac tacatttata ttgatgatct gtaagagcaa    780

aagtattaat ggggatcaca ggattgcagt aacagcagca ggtacccccct cctttaacat   840

ccgcagttac gcctcccacc taccgtcttc tctgccgatc gatgacgatg agcttctcct    900

ccgctataaa tcctctcccc tcctctctcc ctcctcctcc aactccacat cgatcagcag    960

cagcagcagc ttgcacactc gagcttagct tagcttttgc aagagagatc gagctagag    1019
```

<210> SEQ ID NO 7
<211> LENGTH: 1212
<212> TYPE: DNA
<213> ORGANISM: Oryza sativa
<220> FEATURE:
<221> NAME/KEY: misc_feature
<223> OTHER INFORMATION: PRO0081 - putative caffeoyl-CoA 3-O-methyltransferase

<400> SEQUENCE: 7

```
atggtgccat gtcaataaga catcataata gaaactacac tccacaaccc atagtttctt     60

aaagtgggtc attaataaat acatcatcta tcttttctat caatcatatt tattctttat    120

ctattatgac ggcactattt tctcccaatg taaaacttga taatgtctag tgcataggtt    180

ctcgtgttga agctgtttct tacatgagac ccagtttctt cttctctcca ctctctctta    240

attaatataa tgtcacataa gttaaaagtt ctagtaaata ataatatagt taatgacata    300

gacaacatcc tagatgtagg gttaggagtc ttcggacagt agcaaccctg ttttgactcc    360

tttttggct gcccatccac agtcgccacc agaaaattca ctgtgcccaa atcaatggaa    420

gcgcctacta gatccatcca tcttcgtgac agctccgagc tttctcctgg ttatttttct    480

cccaaaaata cattcagaac acgatctcaa atttaaacta atggagtgct actgcatttc    540

ttaattataa gtcgcagcac cactcattaa tcatttccat cacaggtaaa tcgtggtgag    600

ctggtggttg ctactgtact actagtacta cctgtcgcag ctttgtagaa gccgttttcg    660

ctgaagcttc ttcttcttcc ctgggcaaaa taattttaag caggcggaat aatattggga    720

taaacagggt ggacaaaagc gtgcgatccc tttctttaac caaaccacga cgaaagcagg    780

ttaggtcgcg gcaggtggtg gtggtaggaa gaagaagaaa gagaggggaa aaaaaacaaa    840

aatttcacat gcatcatgca tgaagtagta catgtagtac tgagtactgt aataatgttc    900

agtttactgg accgtctcaa cgggaagacc aaattaacgc ttataaaata cccttttttt    960

gggcactgat catggccact acgtttggtg gctcaacaac caggtcaccg tgcgatcgat   1020

cgattgctaa tttatttttt gaaaaggaag ggaggaaaaa agaccgggtg tttggtggcg   1080

ccaccaaccc tgctctcgtg agccgataaa tattgctcgc cggagctctc ggttgacgac   1140

ccaaccaatc gactcgcacc accaccagca gctcaagcag caacagctca aacggaggaa   1200

gatctcatcg cc                                                        1212
```

<210> SEQ ID NO 8
<211> LENGTH: 1052
<212> TYPE: DNA

```
<213> ORGANISM: Oryza sativa
<220> FEATURE:
<221> NAME/KEY: misc_feature
<223> OTHER INFORMATION: PRO0091 - prolamine RP5

<400> SEQUENCE: 8

gtttttctat gaaccggtca ttaaaccgtc cccggttaga ccgaacaagc cacaataatc     60

ttgaaatggg ccttgatgtg gcccaattgg tctgcctaga gcgttttggt tggcaaaaat    120

caatctccta ttctcggcac gtgtgatata caatggtaag tgagatatac aattctcggc    180

acggctacat tacaaggtgt cgcattgtgt caatgtttgg ttaatttgct agattcacat    240

aatacatgcc aggaagttca gaacaatgtg ttgcctttca ccggaaaact ttgttggagc    300

aaatgccttc ttcttttttg cttctgcttc ttgagtccat gtggaggaag cagtagatag    360

ctgatgatat caggattcct tctgtgtctg tgtaggtgta gcaacaccac tataattttt    420

atttagcaac acaatatcaa tttggtctat aaaagtatga attaaatcaa tccccaacca    480

caattagagt aagttggtga gttattgtaa agctctgcaa agttaattta aaagttattg    540

cattaactta tttcgtatca caaacaagtt ttcacaagag tattaatgga acaatgaaaa    600

ccattgaaca tactataatt ttttttctta ctgaaattat ataattcaaa gagcataaac    660

ccacacagtc gtaaagttcc acgtgtagtg cattatcaaa ataatagctt acaaaacata    720

acaaacttag tttcaaaagt tgcaatcctt atcacattga cacataaagt gagcgatgag    780

tcatgtcatt atttttttgc tcaccatcat gtatatatga tgggcataaa agttactttg    840

atgatgatat caaagaacat ttttaggtgc acctaacaga atatccaaat aatatgactc    900

acttagatcc taatatagca tcaagcaaaa ctaacactct aaagcaaccg atagggaaac    960

atctataaat agacaagcat aatgaaaacc ctcctcatcc ttcacacaat tcaaacatta   1020

tagttgaagc atagtagtag aatcctacaa aa                                 1052


<210> SEQ ID NO 9
<211> LENGTH: 1216
<212> TYPE: DNA
<213> ORGANISM: Oryza sativa
<220> FEATURE:
<221> NAME/KEY: misc_feature
<223> OTHER INFORMATION: PRO0095 - putative methionine aminopeptidase

<400> SEQUENCE: 9

cctgatggat gatgaatcac tgatcgattt ctagttctta ttctctgaag atgaaccgaa     60

gatccaagat tggtccatga aattatcctt tcttgatttg gccctccgag aatagattcc    120

tgtgcaatct agtcagtagt tgttcaggtc atgtaaacgt acggtaagaa atttatgtgc    180

agagggtttt ccagtttatc ctatgcattt gacctctggt catgtattga ttctgagaca    240

aagtgtagtg atcgcttgat gatactagta cacattgctg ccttcttttt tgtcctgtaa    300

aagatttatt attggcagca atggatggta gagagggcaa tctgcttctt agttttgagt    360

ataaagtttt aagttttgag cagagtttcg aaaatttgca gtagaaagtt tgaaatttca    420

aattggaagt acagtttttc aaatttccag tataaatttt taaacccact gagaaaccaa    480

gagcatatgg gcgatcaaaa atttcttttc taaaggaaaa atattttttta aaaaacactt    540

agtagtatat caaaattctg aggtaagctc attaggccca ttcactgtac ggcccatgaa    600

gcccagtctg gtgagatggg cctacccgtg caggcagaga tggatgggcc tttaattgta    660

ggcccatgtt ggaaagccca ccaaagccca ataatatatc ctcctcacct tcaaccctaa    720

tcctcctctt cttctagaag actgaaaatt cctctccttt cttctctcgc cctcaccgct    780
```

```
cgccgaggtt gccgtctcct tgtctcctcc gctccttgcg ccgccgccgc gacgagtcgc    840
ggggaggggc ggcgatctcc atctccatct gaggcgagga gagcagggga ggtgagggga    900
tcctggtgag gtgagcatcc acgtcctctt tcttttttc tgattcatct ctctctctct    960
cgcacatcgg gactggaatt tgcttgcgtt cgttcgttaa gttaacccta gcttctcttc   1020
tagatctgga agaaactctt cttcttttaa tttcagagcc ttaaccttaa tagtacaagt   1080
aacagtttgt ttgttccccg aaaagtttgg atgccttcca aatagagaca catgttattt   1140
attttggaat gtaatttgtc cctggattta ttcattcagg tttgtgatta ctggacaata   1200
gaaatattta cacaat                                                   1216
```

<210> SEQ ID NO 10
<211> LENGTH: 1237
<212> TYPE: DNA
<213> ORGANISM: Oryza sativa
<220> FEATURE:
<221> NAME/KEY: misc_feature
<223> OTHER INFORMATION: PRO0111 - uclacyanin 3-like protein

<400> SEQUENCE: 10

```
tcgttaagtt tgatgatttc tgatgaccca tggtcaccta gcggctagca gtaccatgca     60
tgatcaccct ccacaaagaa atggtacagt acatctccgt cccaaaataa gtgcagccat    120
gtatatccat gcctaacgtt tgaccgtccg tcttatttaa aaaaattatg aaaaatttaa    180
aaatatttag tcacacataa agtattattc atgttttatc atctaatagc aacaaaaaat    240
actaatcata aaattttttt taataagata aacggttaaa cgttgaacgt gaatagtgca    300
aaacttattt tagaacggag ggagtacgaa gtaactccgg aactacatat agggcaatta    360
ttgccctatg tatgcatata gtcaatcaat taactgctga caatggaaaa gctaatcaat    420
caatcaatgg tttgattaat caaattaagc caggtcagtc cgtcagtgta cattcactaa    480
ttaaattaac aggtttgttc aacggttcaa ccaacatctg ccatcaacat cttttcgttg    540
cacctttctt gactctttat gctattttgc taaaaaaaaa cttctcttta catcacttat    600
aacaatatat atttctgctt taatttgtaa tctttttttt ctgcgttgca acggaaatca    660
cgagcgatat atggtgaaga ctgatgataa tcgtatttct gatgacccat gattccgcgg    720
tgtaccatct gttctgtcaa ctaaaaagtg gagtagttcc ttgacggaag aagggagcaa    780
aatagaagat attctcagtt gatctgcagt tgttgttagg tcactatatt cagaaatcgc    840
agttgctgtt gtttaaattg tgtgtgacag cagacagcta attatcagta cacgtatatg    900
agcaatacta gtgaatctgt actaatttaa cgagagtatt ttctatatac aaatacaaca    960
gcaaaactgt gccactggcg ccgaatacgt acggacagag ctcaggcaat caggggagca   1020
gcaaaagagg agagagttgg tgccaagcac aactaaaccc aactgcaccc aaaaactaat   1080
cagcatttca gttcgcttta gttagtacta ccacctgcat ctctttacca acactatata   1140
acccgcagtg gacctgcagt catctcacta attcagtgaa gccaccagta ctagtacggc   1200
tctaatcagt tcgcgtttgc taattaactc tgccatc                            1237
```

<210> SEQ ID NO 11
<211> LENGTH: 1100
<212> TYPE: DNA
<213> ORGANISM: Oryza sativa
<220> FEATURE:
<221> NAME/KEY: misc_feature
<223> OTHER INFORMATION: PRO0116 - 26S proteasome regulatory particle
non-ATPase subunit 11

<400> SEQUENCE: 11

```
ctaagggcag cagccattgg gctctatagg tgtggttgca agtgcactta caagcgagca      60
acctggtaga atatccccga gatcagtagt taccgtgatt ggttcagact tgagaggcta     120
atttttcgt acctgtagct ttattacatc gcatttcctc ttattgaagt ttagccgagg      180
tggtgcggat ggatattcag tctaacagac tcaatgaacg ctttgttgta tgacttgtac     240
agtactggct gctcgaacag gatggttcag cttccagaaa tttggcaacg ctccatttca     300
aagaaaatca ttcagtattt gccttcttgt tgttacattg atctcatata aagtcacttt     360
gatcgttgac atcttgtttt ttggttcgtt tgccatggta gtttcccttg ctgctgggag     420
gattgccgcc tgaacttttt ctttttgcg aggatgttat ttttgccaga caagaacggg      480
aataagcaaa ttgtttggtg gaactaaagt aaactcgatc tctttccgag aagtgtatta     540
ttttcacgtg taccatcaat ttttttgaaa gtaaatattt ttccccttta actaatgttc     600
actttggacc ggataatctt acctttattt aactttgggc tatctaactc tcttctaaag     660
catataaacg atcttgagta catcgattcc tacttatcat ttaactctcg tagcttaatg     720
taagattatt tctttgaaat atgataaatt ggatgcatat gaatgaaaga gtcaaggatt     780
aagtgattcc tcaaaaaaaa aaaagagtga aatttattta tttttcccct ttcgacacga     840
agaagggctt ggttggagga aaatggccca gattcagatg accgaggccg agtaccatgg     900
ggcccacaag aataataagc cccgagccca aacgctaagg cccacgagaa gccgtgcgct     960
ggaagaaaga aagaaaccgc ggccgtcttc acaccgaagc ggcggacgag acgactcgca    1020
gtcgcagcct ctttcctcct ccgtctctct ctcccctctt cctctcctcc gcgcggcgaa    1080
cgaagcgagc gagcggcggc                                                1100
```

<210> SEQ ID NO 12
<211> LENGTH: 1216
<212> TYPE: DNA
<213> ORGANISM: Oryza sativa
<220> FEATURE:
<221> NAME/KEY: misc_feature
<223> OTHER INFORMATION: PRO0117 - putative 40S ribosomal protein

<400> SEQUENCE: 12

```
cgtgttcatg ttcgcattta ggattggact tttttaggat ggagaggata tgtcctaacg      60
gaaatgtcat gtctatgctc cgatcttata aatttgttca atagcgttgc aaacgcgatc     120
attaaaaagg cggtaagaga actaccacat tttcgaaagc ccattctctt cgtgagttac     180
tggaattatt tggcatagca catgcataaa gatgctttag taatgagctc aataaaacac     240
gacagctttg catgtagcca caatgctata gtaaatgagt tgtacttctt ttgcattgca     300
aagtggtact gaccttgttt aggcagctag cttcattcat tttttgaatt ctatagttat     360
agttataaag attatcataa tttagataag aatccggtat gtttgagaag ctggagtttc     420
tagagaagct ataacaactc gaagctccct aaacagagcc attgaacatt gagctgtcca     480
gtatatcatg acaaaatgat acattttgca tgggcatatg tgtctaagaa aacaaacatc     540
acaattcaat gagtcactct aaaaaaaaag gcaaaacact caacaaaacc ataccgtgaa     600
agtgaaccta taatgaaatg aaattttgat aagcatgctt acccaggtgg aaatttcaat     660
ctaagaacaa tttccaaaac caccgtccat agaaatatgt ggaattcatt cagaattttc     720
ataccacacg ataaaattta tagggaattt aacttttgcc atttttaccg aacaccacct     780
tttcatttgc tcctataatg ttatcgaaaa gagagtgttt gttaattatt tgtcactttt     840
```

```
atcacgacat gtagccgtga caacgtggcg ttcctcgtgg agcccacccg tcagccgccg     900

tacgcaccac catcaaagaa ttcaagacgg agagcgtcgt cgccgtcggc aaggcggcgt     960

gttttgttca ctgtacgttg cttcggcgtg ggcccaatct tgttcgggcc taactagttc    1020

ttcccagccc aggcccatta agcctaccaa cccggacggc ccgggaggag ctagggtttc    1080

acccttcact atataaacct ctctctcctc ctccggccgc cgcctccgaa gccctagctc    1140

ctcccgccgc cgccgccgcc gccgccgccg cctctccact cgagagaccc agccgccgcc    1200

gccgccgccg ccgcca                                                    1216
```

```
<210> SEQ ID NO 13
<211> LENGTH: 1210
<212> TYPE: DNA
<213> ORGANISM: Oryza sativa
<220> FEATURE:
<221> NAME/KEY: misc_feature
<223> OTHER INFORMATION: PRO0122 - chlorophyll a/b-binding protein
      presursor (Cab27)

<400> SEQUENCE: 13

cagatgccac agtatggtgt accaccagct gctccacacc atgctccacc ggctggccaa      60

ccaatgtatt tcccgaaata atctatcttt atccgatgta caagcaatta gagcaattgc     120

aaatgttgcc tgcaatactc gggtctgggt atcttctctt caaattttgg gttgtaactc     180

gtctatgcag ctattcatat tgtaactcag tgagctccct gtcgcaaatg tgcctctgcg     240

tcagtcgctg tctgtaaact gtccggcaat tagaaattcc catccttagc atgcctggta     300

ttgttcagct cgaaactgaa atttttcttc gtgccctata ttttttcggt gtagataagt     360

gttccgctgg aattttatgc aggtgctgta ccctatgtgc tgcttttttt ttgtgtgggg     420

cgcccccccg gggggggggg ggggtttcct ggcatgattg caaataagaa ccccggggca     480

aatctgctgg ttggttgcaa ataataaccc ctccaaatct gcgcagatga aaccccattc     540

aggacatgaa ttacgattgt tcatgagcta tttggatcat ggaaagattg gaaacaaaca     600

cttacgtcaa ggtttctact aattacgtga ttccgatttc agagtcagcc atggctatac     660

tgcctttgct ccagtaaaca tcgctgctct agtaacaaac attgcagtaa acatcacaac     720

tatccaattc ccttgttgct gctctagtaa aaaacattgc aattatccaa ttcccagata     780

ttttctttca ctactccaaa acctaaagta catatacgtg agttgagtga tccagcaaca     840

taaaaatccg aggctccgag cgatctgcac caaccatctc acccgtccga cgtggcagca     900

gcaaccagcc acagctgaga cctccatcca atagaaaccc tccctttgat tcccccgtat     960

cccggcatcc ggataacgct ggataagagg cgacgcctcc cattggccac acccacccaa    1020

caacgcatcc tggccgtccg atccaccccc accgccgatc tccgccgtcc gtcgccgccc    1080

tcgccaccgt ggccacctgg cagcgccggc cactcccgga cagtttaata caagccacgc    1140

ctttgctccg tgccggccaa aacgtaccct tgtgactaca cccgcttcgc ttcctcccct    1200

ctctaagccg                                                           1210
```

```
<210> SEQ ID NO 14
<211> LENGTH: 1179
<212> TYPE: DNA
<213> ORGANISM: Oryza sativa
<220> FEATURE:
<221> NAME/KEY: misc_feature
<223> OTHER INFORMATION: PRO0123 - putative protochlorophyllide
      reductase
```

<400> SEQUENCE: 14

```
ttgcagttgt gaccaagtaa gctgagcatg cccttaactt cacctagaaa aaagtatact     60
tggcttaact gctagtaaga catttcagaa ctgagactgg tgtacgcatt tcatgcaagc    120
cattaccact ttacctgaca ttttggacag agattagaaa tagtttcgta ctacctgcaa    180
gttgcaactt gaaaagtgaa atttgttcct tgctaatata ttggcgtgta attcttttat    240
gcgttagcgt aaaaagttga aatttgggtc aagttactgg tcagattaac cagtaactgg    300
ttaaagttga aagatggtct tttagtaatg gagggagtac tacactatcc tcagctgatt    360
taaatcttat tccgtcggtg gtgatttcgt caatctccca acttagtttt tcaatatatt    420
cataggatag agtgtgcata tgtgtgttta tagggatgag tctacgcgcc ttatgaacac    480
ctacttttgt actgtatttg tcaatgaaaa gaaaatctta ccaatgctgc gatgctgaca    540
ccaagaagag gcgatgaaaa gtgcaacgga tatcgtgcca cgtcggttgc caagtcagca    600
cagacccaat gggcctttcc tacgtgtctc ggccacagcc agtcgtttac cgcacgttca    660
catgggcacg aactcgcgtc atcttcccac gcaaaacgac agatctgccc tatctggtcc    720
cacccatcag tggcccacac ctcccatgct gcattatttg cgactcccat cccgtcctcc    780
acgcccaaac accgcacacg ggtcgcgata gccacgaccc aatcacacaa cgccacgtca    840
ccatatgtta cgggcagcca tgcgcagaag atcccgcgac gtcgctgtcc cccgtgtcgg    900
ttacgaaaaa atatcccacc acgtgtcgct ttcacaggac aatatctcga aggaaaaaaa    960
tcgtagcgga aaatccgagg cacgagctgc gattggctgg gaggcgtcca gcgtggtggg   1020
gggcccaccc ccttatcctt agcccgtggc gctcctcgct cctcgggtcc gtgtataaat   1080
accctccgga actcactctt gctggtcacc aacacgaagc aaaaggacac cagaaacata   1140
gtacacttga gctcactcca aactcaaaca ctcacacca                          1179
```

<210> SEQ ID NO 15
<211> LENGTH: 1808
<212> TYPE: DNA
<213> ORGANISM: Oryza sativa
<220> FEATURE:
<221> NAME/KEY: misc_feature
<223> OTHER INFORMATION: PRO0133 - chitinase Cht-3

<400> SEQUENCE: 15

```
tttggcgcgg ggcagaagag tggactttaa ctttcttttt aataaaatct ccaattaata     60
tgtaattata atatactttt aatcaaaaca tgcaaagcta gcagtattta catcactaga    120
agtaaatctt tcttgctcat gatgcttcag ccggacggaa ccctaaaata tagatggggc    180
ggatacactc gattaaaaca gctaattgca acacatatca tataaggttt tggaattcat    240
accaaatgct ccgaaattcg tctatttcga tgaggcccaa gacatgacct cctgtttcgc    300
ccatagttta tggtgtttgg taaaatttgg ttaaaatctg tctattttag taggtcccga    360
aattcttatg caattgaatc ctagaaccct atcatattta tattgcaatt gcacaaaaat    420
aatgtgcaat caatatattc caattgcaat acatatcaag catgaggtgt aatacatatc    480
cagccgctag cactgggtct gttgaggtgc ttcttgcagc aacagctgca atctgtttgg    540
ctaggctgtt ggcgccaggc actgctgtcg tgctgcaaca atggcacatt cgtcgagcac    600
acaaccgcgc ctatgcacag cgcaagctcg ctgccttgga ccgtggttcc agtgttgcat    660
caaggcttag tggattgagc gagaagacga actgacaatg ccaaagatgc gatgctgcga    720
gtgtggactg cggaagatga atcgagatca atcaattcgt tatgcttgaa aggctggaat    780
```

```
aactgatcag ttggctggat cgatggtatg tactagataa tatgcggtct aggcctagac    840

caagaagcag aagaggagtc gggtcgggag tgtggggcga cgtaggctgt agctgggccg    900

gccgccccag gccgcctaat gagtgtgtcc gcccctggcc tgacacgatg ggtaattaaa    960

tagttatgca tgtccctctt tgtctaaaca atatgtataa aattgacgat atcttgggca   1020

aaatcactgg gcatggcaca caggagagct actttagcga catgaatcta ggcgaaaatc   1080

tattgaacca aaaatcgact gtaatctcat gaaaattttc gtcataatta tagcaaaatc   1140

gttgttggat tgattgcacg agaaaacaga agaagggagc taggtgatat tatattgttt   1200

tgttgcctac ataaatctta aagcaatcga atggtctaaa atttacaaga tttttaaaga   1260

ggttttcgta ccgtatagac cccggccggg tcaaacttat ttggtcgtcg ctggttgttt   1320

gtagcacgcc agctccatat atgtggattg cagctggtct atgataagtt cggtcgatct   1380

gagatcaatc tatcaatcgt caaccctttg cctttgttag cgagctagcg tgtacacatt   1440

tcaattatat atggtgcatg catggcatcc acgcctccac ggtcaacgtg gaaatatctc   1500

tggaaactta ctttttctaa ataactgaac ggattggagg caggagacaa atttgaccaa   1560

cacaatatat ccacgacggc tagacaatac tagtagatgc atgcatggaa ggatatagta   1620

gtacttgtta atcgtggaaa ctttggtaat gcgaatgcat ttcaattcgt tgctgaagat   1680

cgatgcacca tgcatatcca tctctatata aagccatgcg atcccaccga ttcttgcaca   1740

cacactagct acttctactt ctatcatacc aaacaaacta gcttaatttg cattgcatca   1800

cattgccg                                                            1808
```

<210> SEQ ID NO 16
<211> LENGTH: 1828
<212> TYPE: DNA
<213> ORGANISM: Oryza sativa
<220> FEATURE:
<221> NAME/KEY: misc_feature
<223> OTHER INFORMATION: PRO0151 WSI18

<400> SEQUENCE: 16

```
gcttgagtca tagggagaaa acaaatcgat catatttgac tcttttccct ccatctctct     60

taccggcaaa aaaagtagta ctggtttata tgtaaagtaa gattctttaa ttatgtgaga    120

tccggcttaa tgcttttctt ttgtcacata tactgcattg caacaattgc catatattca    180

cttctgccat cccattatat agcaactcaa gaatggattg atatatcccc tattactaat    240

ctagacatgt taaggctgag ttgggcagtc catcttccca acccaccacc ttcgtttttc    300

gcgcacatac ttttcaaact actaaatggt gtgtttttta aaaatatttt caatacaaaa    360

gttgctttaa aaaattatat tgatccattt ttttaaaaaa aatagctaat acttaattaa    420

tcacgtgtta aaagaccgct ccgttttgcg tgcaggaggg ataggttcac atcctgcatt    480

accgaacaca gcctaaatct tgttgtctag attcgtagta ctggatatat taaatcatgt    540

tctaagttac tatatactga gatgaataga ataagtaaaa ttagacccac cttaagtctt    600

gatgaagtta ctactagctg cgtttgggag gacttcccaa aaaaaaaagt attagccatt    660

agcacgtgat taattaagta ctagtttaaa aaacttaaaa aataaattaa tatgattctc    720

ttaagtaact ctcctataga aaacttttac aaaattacac cgtttaatag tttggaaaat    780

atgtcagtaa aaaataagag agtagaagtt atgaaagtta gaaaaagaat tgttttagta    840

gtatacagtt ataaactatt ccctctgttc taaaacataa gggattatgg atggattcga    900

catgtaccag taccatgaat cgaatccaga caagtttttt atgcatattt attctactat    960
```

```
aatatatcac atctgctcta aatatcttat atttcgaggt ggagactgtc gctatgtttt   1020

tctgcccgtt gctaagcaca cgccaccccc gatgcgggga cgcctctggc cttcttgcca   1080

cgataattga atggaacttc cacattcaga ttcgataggt gaccgtcgac tccaagtgct   1140

ttgcacaaaa caactccggc ctcccggcca ccagtcacac gactcacggc actaccaccc   1200

ctgactccct gaggcggacc tgccactgtt ctgcatgcga agctatctaa aattctgaag   1260

caaagaaagc acagcacatg ctccgggaca cgcgccaccc ggcggaaaag ggctcggtgt   1320

ggcgatctca cagccgcata tcgcatttca caagccgccc atctccaccg gcttcacgag   1380

gctcatcgcg gcacgaccgc gcacggaacg cacgcggccg acccgcgcgc ctcgatgcgc   1440

gagcccatcc gccgcgtcct ccctttgcct ttgccgctat cctctcggtc gtatcccgtt   1500

tctctgtctt ttgctccccg gcgcgcgcca gttcggagta ccagcgaaac ccggacacct   1560

ggtacacctc cgccggccac aacgcgtgtc ccccctacgt ggccgcgcag cacatgccca   1620

tgcgcgacac gtgcacctcc tcatccaaac tctcaagtct caacggtcct ataaatgcac   1680

ggatagcctc aagctgctcg tcacaaggca agaggcaaga ggcaagagca tccgtattaa   1740

ccagcctttt gagacttgag agtgtgtgtg actcgatcca gcgtagtttc agttcgtgtg   1800

ttggtgagtg attccagcca agtttgcg                                      1828
```

```
<210> SEQ ID NO 17
<211> LENGTH: 1267
<212> TYPE: DNA
<213> ORGANISM: Oryza sativa
<220> FEATURE:
<221> NAME/KEY: misc_feature
<223> OTHER INFORMATION: PRO0169 - aquaporine

<400> SEQUENCE: 17

cgtcctcctt ttgtaacggc tcgcaaatac aatgggttgt ttagattcat gtcattttaa     60

atcatattat tttttataaa gttatcaaaa tgtacatata tttatttatt tttaccaaac    120

tttactaaat gagataatcc aacaaatggc atttaaagcg ttcaaatcca agaaatgcca    180

tcgccgttat gcttccgtcc gtttcacgcc gttaaaatac aatgttcatc ctataacact    240

taatggtgtg gaatggacgg aaccctaacg gcgatggcat ttttgggata aagtcgtttg    300

tacgatggca tttcttagaa ctcatatttg tcgatggcat tttttgaatt tggatgattg    360

tcaatggtat tttttggatt atctcttagt aaatacataa ggaatcatgc caaaacttga    420

caatattgtc aacttatcaa aatttaattg ggattatttt ggcgataata tgaacagccc    480

ttacatttct gaagaattat agctcaaata tggctatggc cctgtttgga ttcggagggc    540

tatttaatag ccctccggaa tcttgctatt taagagtatt aaacgtagat tactgataaa    600

actcattcca taacccctac gctattctac gagacgaatc taacgaggta tattaatcca    660

tgatttgcta cagtaatcag ccgctaatcg tggattaata tacatcatta gattcgtctc    720

gtaaaatagg ctagggatta tggaatcggt tttatcggta atctatgttt aatacttcta    780

aatagcaaga ttccgaaggg ctatttaata gctcggagca tccaaacaag gcctatgttt    840

agatccaaac ttccaacttt ttctatcaca ttaaactgtc atacatacat aacttttcag    900

tcacatcgta ccaatttcaa cccaaacttt caactttgga agaactaaac acagcatatg    960

acagtgcagt tcagctcaat tttgttcgga gcctaaaaaa aagaaaagaa aaaaagctca   1020

atttggataa ggctatgaat aaactcaaaa aagcatccaa cctaaccacc acactggccc   1080

accagggccc acgctccact cccgtgatca tcacctcctt ccctttccag aaccaccttc   1140
```

```
tccttccttc ctcctcttct tcttcagtgt actctgcctt tataacaccc tactcctctc   1200

tctcacctcc accatctagc tcactcacac agtctccact cacacgcatt gcagaggaga   1260

ggcgaca                                                             1267


<210> SEQ ID NO 18
<211> LENGTH: 1130
<212> TYPE: DNA
<213> ORGANISM: Oryza sativa
<220> FEATURE:
<221> NAME/KEY: misc_feature
<223> OTHER INFORMATION: PRO0170 - High mobility group protein

<400> SEQUENCE: 18

catgcggcta atgtagatgc tcactgcgct agtagtaagg tactccagta cattatggaa     60

tatacaaagc tgtaatactc gtatcagcaa gagagaggca cacaagttgt agcagtagca    120

caggattaga aaaacgggac gacaaatagt aatggaaaaa caaaaaaaaa caaggaaaca    180

catggcaata taaatggaga aatcacaaga ggaacagaat ccgggcaata cgctgcgaaa    240

gtactcgtac gtaaaaaaaa gaggcgcatt catgtgtgga cagcgtgcag cagaagcagg    300

gatttgaaac cactcaaatc caccactgca aaccttcaaa cgaggccatg gtttgaagca    360

tagaaagcac aggtaagaag cacaacgccc tcgctctcca ccctcccacc caatcgcgac    420

gcacctcgcg gatcggtgac gtggcctcgc cccccaaaaa tatcccgcgg cgtgaagctg    480

acaccccggg cccacccacc tgtcacgttg gcacatgttg gttatggttc ccggccgcac    540

caaaatatca acgcggcgcg gcccaaaatt tccaaaatcc cgcccaagcc cctggcgcgt    600

gccgctcttc cacccaggtc cctctcgtaa tccataatgg cgtgtgtacc ctcggctggt    660

tgtacgtggg cgggttaccc tgggggtgtg ggtggatgac gggtgggccc ggaggaggtc    720

cggccccgcg cgtcatcgcg gggcggggtg tagcgggtgc gaaaaggagg cgatcggtac    780

gaaaattcaa attaggaggt ggggggcggg gcccttggag aataagcgga atcgcagata    840

tgcccctgac ttggcttggc tcctcttctt cttatccctt gtcctcgcaa ccccgcttcc    900

ttctctcctc tcctcttctc ttctcttctc tggtggtgtg ggtgtgtccc tgtctcccct    960

ctccttcctc ctctcctttc ccctcctctc ttccccccctc tcacaagaga gagagcgcca   1020

gactctcccc aggtgaggtg agaccagtct ttttgctcga ttcgacgcgc ctttcacgcc   1080

gcctcgcgcg gatctgaccg cttccctcgc ccttctcgca ggattcagcc               1130


<210> SEQ ID NO 19
<211> LENGTH: 1230
<212> TYPE: DNA
<213> ORGANISM: Oryza sativa
<220> FEATURE:
<221> NAME/KEY: misc_feature
<223> OTHER INFORMATION: PRO0171 - reversibly glycosylated protein RGP1

<400> SEQUENCE: 19

tagtaccatt cttccctcgt gagcataaat gtattcatac aaaatagtaa aatgtatcct     60

cacaaagatt gtaagtatat ctcgcaacta taaatatgtt gtcattttag taacaattgt    120

tcataaaata gtaatcatgt tctccataac agtaaatgac gaggcgttaa tagtggttta    180

ggttctcatg attgtaaatg ttgagtcgct tgtagcggct taagatatag tagagagtat    240

atctagtttt atcaagacaa acattgcgta atgcctcgga cctaatataa aagtaggaat    300

tttaaccttt gagaaactgt aaccaattga aactgcaagc tttaaaaaaa catctattgg    360

aagtgatatt atatagacaa aataagtttc ttactcttac tctctcagtt tcaagttata    420
```

```
aaatgttttg gctttggtca aaatcaaact tcttcaagtt taatcaagtt tatagaaaaa    480
atagtaatat ccaagataaa tttattataa aaatatattt aattattatt ttaataaaac    540
taatttggta atgtaaatat tactatattt gtctataaac ttagtcaaat ttaaaacagt    600
ttaactttga ccaaagtcaa aacatcttat aacctgaaat ggatggagta tttgtttgtt    660
tctattttag gaaacggccg tttctttcca ttgattttga gataagcaga gctttaaacc    720
actgccacta ttgtgcattt catttgattt aacactttta ccccttatct ccaataaaaa    780
cgatattaag ataccccctat cttttatcca ccgcttggaa caaaccaaaa aaaataaaaa    840
ttcaaacctt ctacactggt acacacgttc tctctttcca tgcaccgaca ggtctctccc    900
agatccaacc caaaataaat ttggacgcat cccaaaattc ggcaaacata tgacgcaaac    960
caaaacaaaa taggcacaaa ataatataat actcctatct aattaattat acacaatttt   1020
ttttaaaaaa aaagcaaggc aagcgaagca aagcaaagaa ggaaacgaat aacaaagtcg   1080
tcgtcctccc ggagctcccg ctctataaat cgctcctcct ccccacccac ccaaacccac   1140
acacacctca cacctcacca ccatcacctc ctcctcctcc tcctcttcct ccgcgcgcgc   1200
gagatccagg gagagggaga gggagagatc                                    1230
```

<210> SEQ ID NO 20
<211> LENGTH: 1234
<212> TYPE: DNA
<213> ORGANISM: Oryza sativa
<220> FEATURE:
<221> NAME/KEY: misc_feature
<223> OTHER INFORMATION: PRO0173 - cytosolic MDH

<400> SEQUENCE: 20

```
gtttggttgg tgaccgcaat ttgctatacc aaaatcttag acacagttga attaagctac     60
actttattag cacattggcc cgtgcgttat attgtcattt tctagccaaa gtttgccata    120
attgtggcta acaaattgtt ggccacattt tggctacgtt cgataggaca tgttcccaac    180
ttctccttct cgtttttcgc gcgtacgctt tttcaaactg ttaaacggtg tgtttttttgc    240
aaaatatttt tttacgaaag ttgcttaaaa aattatatta atctattttt tttaaaaaaa    300
gtagctaaaa cttaattaat ctcacgctag acgctgcttc gttttacgtg tcgggtaccc    360
aaccctcact cccgaacaca gcctttgtgt ggtttactac agttatagta aagctagtct    420
ccatccaaac aatcctttag tccatataac ttcgtatact ccaaaattcc actcgttcta    480
cggacatcac taatacgaag atcaagtgga agatagatat ttttaatgac atgttatttt    540
cagtgaacac ttgaggtcct cacgatccac aaacacacat tttcgtagat aagttctgaa    600
atactccata cggcggttgt cacgatgtca tgatcgtcgt tacccaagga agaagaaaag    660
agtggcatct tctccacgcc agtgttccca acggagcatc ttttcttccc ccacacggca    720
tcgacgtcac actttctggt gcaaacttta ataattagtc caaaaacaaa aaaagaattt    780
cggccacatc ttctcccgaa acgccaggtg ggccccacct gcatcactga cagcctgtcc    840
ccacaacgcg cagtcgtgtc cccacctgtc aggatgttag cgtctccgtt gcaggtttcc    900
cagatcccat cgccgatctg tgggccagcg cccacggtgt cacgcccgcg cacacctggc    960
tccaacccac ccaccccacg cgctccgtgg ccgacagcgt ggacccacct aggtggggcc   1020
caccgtcagt gggagatggg taggggagcc cccacgtggg agcaacgggg gttctccggg   1080
ctccccgtcg ccgcgaggtt aaataacggc cacccgtttc cccctctctc gcaaaactca   1140
cccaaaagag cagcgtcgcc tctcctcctc ccccctaacc cctacgcttc cagaaccttc   1200
```

```
tcgaagctcc cgctcccccc ccccttccgc tcca                              1234


<210> SEQ ID NO 21
<211> LENGTH: 1553
<212> TYPE: DNA
<213> ORGANISM: Oryza sativa
<220> FEATURE:
<221> NAME/KEY: misc_feature
<223> OTHER INFORMATION: PRO0175 RAB21

<400> SEQUENCE: 21

gtcaccaccg tcatgtacga ggctgcttca ccactgcctc actgccacca gcgtctcccg     60

ccgcgtgcaa tacaagaaga aacatcgaac ggtcatataa ggtaagaccc actaccgatt    120

taacctatca ttcccacaat ctaatccact tatttctctt cccatgatct tatcctctca    180

tttctcctca ctacttttgc atttgtagga aacacaatga caccgtcgaa gaaagctggt    240

ggagcaccgt agccagcaat caccaaaaca cagaggggag gaggtcggca gcggccatgc    300

ggacggcgat gagacaacgc gacgcaaaga gggaggagga cgttggcgat catgctggtg    360

ttggcggagg aggtcactgg ccatgcgaat gacagcgggg cagcgcaaca caaaaagggg    420

ggaggatgcc ggcgaccacg ctagtaccat gaagcaagat gatgtgaaag ggaggaccgg    480

acgagggttg gacctctgcc gccgacgtga agagcgtgat gtgtagaagg agatgttaga    540

ccagatgccg acgcaactta gccctgcaag tcacccgact gcatatcgct gcttgccctc    600

gtcctcatgt acacaatcag cttgcttatc tctccatact tgtcgtttgt ttcccgtggc    660

cgaaatagaa gaagacagag gtgggttttg ttggagagtt ttagtggtat tgtaggccta    720

tttgtaattt tgttgtactt tattgtatta atcaataaag gtgtttcatt ctattttgac    780

tcaatgttga atccattgat ctcttggtgt tgcactcagt atgttagaat attcattccg    840

ttgaaacaat cttggttaag ggttggaaca tttttatctg ttcggtgaaa catccgtaat    900

attttcgttg aaacaatttt tatccgacag caccgtccaa caatttacac caatttggac    960

gtgtgataca tagcagtccc caagtgaaac tgaccaccag ttgaaaggta tacaaagtga   1020

acttattcat ctaaaagacc gcagagatgg gccgtggccg tggctgcgaa acgacagcgt   1080

tcaggcccat gagccattta ttttttaaaa aaatatttca acaaaaaaga gaacggataa   1140

aatccatcga aaaaaaaaaa ctttcctacg catcctctcc tatctccatc cacggcgagc   1200

actcatccaa accgtccatc cacgcgcaca gtacacacac atagttatcg tctctccccc   1260

cgatgagtca ccacccgtgt cttcgagaaa cgcctcgccc gacaccgtac gtgcgccacc   1320

gccgcgcctg ccgcctggac acgtccggct cctctcccgc cgcgctggcc accgtccacc   1380

ggctcccgca cacgtctccc tgtctccctc cacccatgcc gtggcaatcg agctcatctc   1440

ctcgcctcct ccggcttata aatggcggcc accaccttca cctgcttgca caccacagca   1500

agagctaagt gagctagcca ctgatcagaa gaacacctcg atctctgaga gtg          1553


<210> SEQ ID NO 22
<211> LENGTH: 1087
<212> TYPE: DNA
<213> ORGANISM: Oryza sativa
<220> FEATURE:
<221> NAME/KEY: misc_feature
<223> OTHER INFORMATION: PRO0177 - Cdc2-1

<400> SEQUENCE: 22

cagacaccta gaatatagac attcccaaaa aataatcact atgcatcagc atcactatac     60
```

```
atgacttggg tctagtgatg gaagtggata gttccactac ctacataaaa acccactact    120

agtttattac ttttcacatg atagcataaa atttaaagaa aaaataaaca gaagtggaat    180

aagcgaaaaa ccccgcttac ccgccccatt tacatcccta cttggatcct gcatgtcagt    240

aagatatcag aattatatgt tttagaatta tatgtttttt tggaaggtgg aaatcggatt    300

attagacgca acataccaag tggcgtatac ttggcttcac tctttccatc agagcaagcg    360

taaaagatca cgtattcacg tcacatggag taactgagcg aatttttttc atttttaaat    420

ttttgttttt taatatttac ataaatatta taccggcgaa aatatttaca aaagtagacc    480

ctgctgccct tctccttctc gagaagagcg gcagggtgat gtcagggaca gaaataaact    540

ccaaaaatgc atttttggct gggcgaaaat tgcacttacc cccttgctgc cctctacaaa    600

ggttgcaagg gacctcagtg caaaatacgc acaccttgcc gtcctccact tggacggcat    660

gggctatttc tgtaaatatt ttggatggta taatatttct gtaaatatta aaaaataaaa    720

atttaaaaat gaaaaaattc tatctgggct cccttctctc atctcacacg gcccaccaca    780

caatcccggc ccacatattt cctgggccca tttccgtgtg aatggagacg gcccattggc    840

gcgcacatgc ggaaaagcgt acacacgatt cgaaatttga aatctcaaaa agcgcccgtt    900

agagcgcgtc ccctccaacg gctatcccca atacaaaaga tcactcgaat cccccccaaa    960

tcgaccaaac cctaaatcca cgcgcattcc acaccaccca accagcgaga gagagatggc   1020

ggcgctccac caccaggcgg cggcggcgcc ggtgacgacg acgacggacg gggcgagct   1080

gcgggcg                                                             1087
```

<210> SEQ ID NO 23
<211> LENGTH: 1272
<212> TYPE: DNA
<213> ORGANISM: Oryza sativa
<220> FEATURE:
<221> NAME/KEY: misc_feature
<223> OTHER INFORMATION: TC89946 (PRO0110)
<220> FEATURE:
<221> NAME/KEY: misc_feature
<222> LOCATION: (17)..(17)
<223> OTHER INFORMATION: n = any nucleotide
<220> FEATURE:
<221> NAME/KEY: misc_feature
<222> LOCATION: (50)..(50)
<223> OTHER INFORMATION: n = any nucleotide

<400> SEQUENCE: 23

```
tttgacgact gaatcgnggc tcgcctctgc ggcggccgct ctagattagn gtttcccctg     60

tctgttgtaa ttcggcacga gggctgatca agagctctta attagctagc tagtgattag    120

ctgcgcttgt gatcgatcga tctcgggtac gtagcaatgg cgtccaaggc gttcgctctg    180

ttcctggccg tgaacctcgt cgtgctcggg gtggcaagcg cctgcggcgg cagcccgtcg    240

tgcccgacgc cgacgccgtc gaccccgaca ccgtcaacgc cgacgccgac gccgtcggcg    300

ttcgggaggt gcccccgcga cgcgctgaag ctgggcgtgt gcgccaacgt gctgggcctg    360

atcaaggcca aggtgggcgt gcctccggcg gagccgtgct gcccgctgct ggaggggctc    420

gtcgacctcg aggcggcggt gtgcctctgc acggccatca ggggcaacat cctcggaatc    480

aacctcaacc tccccatcga cctcagcctc atcctcaact actgcggcaa gaccgtcccc    540

accggcttca agtgctaagc agcgtgcata tgcaatgcct gcatgggttg atcctacgta    600

cggtgattag ttggctttga cgactcttga tttgatttgc ttgctgctct gtttatttgc    660

tactacgtta cgtacgtact ttgcatgcaa cgcaacgcat gatcgatcgt gcatgctggc    720
```

```
tgtttgtacg tatcacggta ccagtttgga ttctctctgt actctctcct ttgtcttctt    780

tgtagtactc ttattcccgc tatccgtacg tgcgcatttg ttgtaagggc cggtgctagc    840

ttgtgtgccg gtaccaactt ctaataaagc tatgggtgga acttcaaaaa aaataaaaaa    900

aaaactggag ggggggcccg ggtccaattt agactataat gagtttaaca ccccgctcat    960

cggccgaaga taacaacacc gggcttggaa aacctagact gcccaactaa tggacggaag   1020

acagactctt ggactgaaac tgaacgaaac aagaccaccc accccatcta accacagcca   1080

cctaccgcca aagattccaa taatgtgaat cagtcggtaa tagaacactc ctcttgtacg   1140

attttactgc ccgcgccacc cctcggtacg cacttatata tatcgggccg tagtaatttc   1200

ctggttccgt cacttccctc atcgcacctg ctagtcgtgg cttacatacg tgcgtcctct   1260

tattatcgag cg                                                       1272
```

```
<210> SEQ ID NO 24
<211> LENGTH: 2425
<212> TYPE: DNA
<213> ORGANISM: Oryza sativa
<220> FEATURE:
<221> NAME/KEY: misc_feature
<223> OTHER INFORMATION: TC90358 (PRO0005)
<220> FEATURE:
<221> NAME/KEY: misc_feature
<222> LOCATION: (1558)..(1558)
<223> OTHER INFORMATION: n = any nucleotide

<400> SEQUENCE: 24
```

```
cccacattga ataattattt taaataattt aagttttttt tttttggctt tagatatatt     60

cccaatcccc aacctcccaa taatccgatc tctcccagtt ctgttcggat caaggctgtg    120

tcgatcgcaa aaaagaaaaa aaaaacaatt tccttttggg gtggttcatc tgttgatcac    180

ttctttgttt cccgcgtttt gttggggatt cgattttcgg gttaagattt tctacacgat    240

ggccttgaac ttggctcaga gcgccgcggc ggcagcgtgc ttcgcgaccg ccggtgatgc    300

gcggcgagct gcttcggtgg tcgccatgcc gtcgtcgtcg tcgtcggcca cgacgagcct    360

gaggatgaag aggcaggcgg cgtgcgagcc ggtggcgtgc cgggcggtgg ccaggcacgt    420

ggcggcggcg gcggcgagca gcaggaggaa cggcgtgccg gtgttcgtga tgatgccgct    480

ggacacggtg agcaagtgcg ggagcgcgct gaaccggagg aaggcggtgg cggcgagcct    540

ggcggcgctg aagagcgccg gcgtggaggg gatcatggtg gacgtgtggt ggggcatcgt    600

ggagagcgag ggcccccggcc ggtacaactt cgacggctac gtggagctca tggagatggc    660

ccgcaagacc ggcctcaagg tccaggccgt catgtccttc caccagtgcg gcggcaacgt    720

cggcgactcc gtcaacatcc cgctcccgag gtgggtggtg gaggagatgg agaaggacaa    780

cgacctcgcc tacaccgacc aatggggacg ccgcaacttc gagtacatct ccctcggctg    840

cgacgccatg cccgtcttca agggccgcac gcccgtcgag tgctacaccg acttcatgcg    900

cgccttccgc gaccacttcg cctccttcct cggcgacacc atcgtcgaaa tccaagtcgg    960

catgggcccc gccggcgagc ttcggtaccc gtcctacccg gagagcaacg gcacctggag   1020

gttccccggc atcggcgcct tccaatgcaa cgacaggtac atgcgtagca gcctgaaggc   1080

ggcggcggag gcgaggggca agccggtagt ggggccacgg cgggccgacg gacgccggcg   1140

gctacaacaa ctggccggaa gacacggtgt tcttccgcgg cgactgcggc gggtggagca   1200

ccgagtacgg cgagttcttc ctgtcgtggt attcgcagat gctgctggag cacggcgagc   1260

gcgtgctgtc gggcgcgacg tccgtgttcg gcgacggcgc cggcgccaag atctcggtca   1320
```

```
aggtggccgg catccactgg cactacggca cgcggtcgca cgcgccggag ctcacggcgg   1380

ggtactacaa cacgcggcac cgcgagcggc tacctcccga tcgcgcgcat gctggcgcgc   1440

cacggcgccg tgctcaactt cacctgcgtg gagatgcgcg accacgagca gccgcaggag   1500

gcgcagtgca tgcccgaggc gctcgtcagg caggtggccg ccgcggcgcg cgcggcgnga   1560

cgtcgggctc gccggggaga acgcgctgcc gcggtacgac ggcacggcgc acgaccaggt   1620

ggtcgccgcc gccgccgacc gcgcggcgaa ggaccggatg gtcgccttca cctacctccg   1680

gatggggccc gacctcttcc acccggacaa ctggcgccgg ttcgtcgcct tcgtccgccg   1740

catgtccgag tccggctcgc cgcgggaggc cgccgagagc gccgcgcacg gcgtcgcgca   1800

ggccaccggc tcgctcgtgc acgaggccgc ggtcgcgctc cggagctagc accggtcaga   1860

cgctcatata caccgtcgcc tcgaggtcgg attccgatgt gggatcattc gatctccctt   1920

tttttttct tctttttgcc attttgtaca gccttttggg gagctttgga tttgtgcttt   1980

ttgtctcggg aggaaaaccg ctctggaggt cgaagagagc gtcattttcc tcccgttgaa   2040

gatcacgaat catttacgtt agagatgatg taattaagca gggaggggag gggaacacac   2100

acacactggc actcaaaagt tgttgtcacg cttggggaat atatccattt ccagccaaaa   2160

aaaaaacgca gaaatgcgtt gtgttcttgc gctctggttc gttgctgctg tgggtcagat   2220

tcagctggtg aaaaaactac agtactactg aaactgaaac tactagagcc tagagggaga   2280

ttaagctaag ttaattgcac gagtaattac tccacggttg tgtttagggt ctacgtcggc   2340

agattttgct ttctggtaga tccctaacct tatgtttgtt gggaatttta taaaggagct   2400

aagtttgcct attgatttgc aatct                                         2425


<210> SEQ ID NO 25
<211> LENGTH: 3410
<212> TYPE: DNA
<213> ORGANISM: Oryza sativa
<220> FEATURE:
<221> NAME/KEY: misc_feature
<223> OTHER INFORMATION: TC83635 (PRO0009)

<400> SEQUENCE: 25

ccatggacac cgcctccgtc accggtggcg agcacaaggg gaaggagaag acgtgccggg     60

tgtgcggcga ggaggtggcg gcgagggagg acgggaagcc gttcgtggcg tgcgccgagt    120

gcggcttccc ggtgtgcaag ccctgctacg agtacgagcg cagcgagggc acccagtgct    180

gcccccagtg caacacccgc tacaagcgcc acaaagggtg cccacgggtg gaaggcgacg    240

aggacgacgg cggcgacatg gacgacttcg aggaggagtt ccagatcaag agccccacca    300

agcagaaacc cccccacgag cccgtcaact tcgacgtcta ctcggagaac ggcgagcagc    360

cggcacagaa gtggcgccct ggaggcccgg cgctctcttc cttcaccgga agcgtggctg    420

ggaaggatct ggagcaggag agggagatgg agggtggcat ggagtggaag gacaggatcg    480

acaagtggaa gacgaagcag gagaagcggg gcaagctcaa ccgcgacgac agcgacgacg    540

acgacgacaa gaacgacgac gagtacatgc tgctcgcgga ggcgaggcag ccgctgtgga    600

ggaaggtgcc gatcccgtcg agcaagatca acccgtaccg gatcgtgatc gtgctccggc    660

tggtggtgct ctgcttcttc ctcaagttcc ggatcacgac gccggcgatg gacgcggtgc    720

cgctgtggct ggcctcggtg atctgcgagc tgtggttcgc gctgtcgtgg atcctcgacc    780

agctgcccaa gtggtcgccg gtgacgaggg agacgtacct ggaccggctg gccctccggt    840

acgagcgcga cggcgagccg tgccgcctgg ccccgatcga tttcttcgtc agcacggtgg    900
```

-continued

```
acccgctcaa ggagccgccc atcatcaccg ccaacaccgt gctgtccatc ctcgccgtcg     960
actaccccgt cgaccgcgtc tcctgctacg tctccgacga cggcgcgtcc atgctgctct    1020
tcgacacgct ctccgagacc gccgagttcg cccgccggtg ggtccccttc tgcaagaagt    1080
tcaccatcga gccccgcgcc cccgagttct acttctccca gaagatcgac tacctcaagg    1140
acaaggtcca gcccaccttc gtcaaagaac gccgcgccat gaagagagag tatgaggagt    1200
tcaaggtgag gataaacgcg ctggtggcga aggcgcagaa gaagccggag gaagggtggg    1260
tgatgcagga cgggacgcca tggccgggga acaacacgag ggaccacccg gggatgatcc    1320
aggtgtacct gggcagccag ggcgcgctcg acgtcgaggg cagcgagctg ccgcggctgg    1380
tgtacgtgtc ccgcgagaag cggcccggct acaaccacca caagaaggcc ggcgccatga    1440
actccctcgt tcgcgtctcc gccgtgctta ccaacgcccc cttcatcctc aacctcgact    1500
gcgaccacta cgtcaacaac agcaaggccg tccgcgaggc catgtgcttc ctcatggaca    1560
agcagctcgg caagaagctg tgctacgtcc agttccccca gcgcttcgac ggcatcgacc    1620
gccacgatcg ctacgccaac cgcaacaccg tcttcttcga catcaacatg aaggggctgg    1680
acgggataca ggggccggtg tacgtgggga cggggacggt gttcaacagg caggcgctgt    1740
acggatacga cccgccgcgg ccggagaaga ggccgaagat gacgtgcgac tgctggccgt    1800
cgtggtgctg ctgctgctgc tgcttcggcg gggggaagcg cggcaagtcg cacaagaaca    1860
agaagggcgg cggcggcggc gagggcggcg gcctcgacga gccgcgccgc gggctgctcg    1920
ggttctacaa gaagaggagc aagaaggaca agctcggcgg cggcgcggcg tcgctcgccg    1980
gagggaagaa agggtaccgg aagcaccagc gcgggttcga gctggaggag atcgaggagg    2040
gcctcgaggg gtacgacgag ctggagcgct cgtcgctcat gtcgcagaag agcttcgaga    2100
agcggttcgg ccagtcgccg gtgttcatcg cctccaccct cgtcgaggac ggcggcctcc    2160
cccagggcgc cgccgccgac cccgccgccc tcatcaagga ggccatccac gtcatcagct    2220
gcggctacga ggagaagacc gagtggggca aggagattgg gtggatctac gggtcggtga    2280
cggaggacat cttaacgggg ttcaagatgc attgccgtgg gtggaagtcg gtgtactgca    2340
cgccggcgag ggcggcattc aaggggtcgg cgcccatcaa cctgtcggat cgtctgcacc    2400
aggtgctccg gtgggcgctc ggctccgtcg agatcttcat gagccgccat tgcccgctct    2460
ggtaccctat ggcggccgcc tcaagtggct cgagcgcttc gcctacacca acaccatcgt    2520
ctaccccttc acctccattc cctcctcgc ctactgcacc atccccgccg tctgcctcct    2580
caccggcaag ttcatcatcc ccacgcttaa caatttggcg agcatatggt tcatagcgct    2640
tttcctgtcg atcatcgcga cgggggtgct ggagctgcgg tggagcgggg tgagcatcga    2700
ggactggtgg aggaacgagc agttctgggt gatcggcggc gtgtcggcgc acctgttcgc    2760
cgtgttccaa ggcctcctca aggtgctcgg cggcgtggac accaacttca cggtgacgtc    2820
caaagccgcc gccgacgaag accgacgcgt tcggcgagct ctaactgttc aagtggacga    2880
cgctgctggt gccgccgacg acgctgatca tcatcaacat ggtggggatc gtcgccggcg    2940
tgtcggacgc cgtgaacaac gggtacgggt cgtggggccc gctgttcggg aagctcttct    3000
tctccttctg ggtcatcctc cacctctacc ccttcctcaa ggggctcatg gggaggcaga    3060
accggacgcc cacaattgtc gtgctctggt ccaacctcct cgcctccatc ttctccctcg    3120
tctgggtcag gatcgacccc ttcatcccca agcccaaggg ccccgtcctc aagccatgcg    3180
ggtctcgtg ctgagctgct gctgctactt ctctgtgtct ctgcattttg caagagggat    3240
gaccggatgg atgattcttg ttgtatggag tattttgact tgttcatgta caagtttttg    3300
```

```
tgagtgggat aaaagtgttt tgggggtaaa atttgtaaga actgaggtgg agattatact   3360

cgaatttaag aacaattgtt tttgaatttt cttttaagat ttttgggagt              3410


<210> SEQ ID NO 26
<211> LENGTH: 602
<212> TYPE: DNA
<213> ORGANISM: Oryza sativa
<220> FEATURE:
<221> NAME/KEY: misc_feature
<223> OTHER INFORMATION: TC83117 (PRO0058)

<400> SEQUENCE: 26

cccccccctc gaggttcgac ccactcgtcc gctgacggtt agttccaagg gaaagaagaa     60

atggaggctt cacgcaaggt gttctcggcc atgcttctca tggtgctgct gcttgcagcc    120

actggtgaga tgggcgggcc ggtgatggtg gcggaggctc ggacgtgcga gtcgcagagc    180

caccggttca agggcccgtg cgcccgcaag gcgaactgcg ccagcgtatg caacacggag    240

ggcttccccg acggctactg ccacggcgtc cgccgccgct gcatgtgcac caagccctgc    300

ccctgatcga tgaaccagca gctagcgcag cagcttgtgc cgccacctcg cgcatgtgtc    360

atcgtgtcga tcgatcggat cctagctgcc ctatgaatga ataaaagtgt gtggcttatg    420

cgtggttttc tcttggagaa ctttggcttt tgtggtgtta agttcgatcg ttttgtgcat    480

ccaccatcca tccatcctcc cattctgctt gttctaaggt tatactacta cttgagaagg    540

tgatgcaatt gtgctcaaca gtttattaat acttcatccg ttttaaaatg tttgaccccg    600

tt                                                                   602


<210> SEQ ID NO 27
<211> LENGTH: 1170
<212> TYPE: DNA
<213> ORGANISM: Oryza sativa
<220> FEATURE:
<221> NAME/KEY: misc_feature
<223> OTHER INFORMATION: TC89913 (PRO0061)
<220> FEATURE:
<221> NAME/KEY: misc_feature
<222> LOCATION: (15)..(16)
<223> OTHER INFORMATION: n = any nucleotide
<220> FEATURE:
<221> NAME/KEY: misc_feature
<222> LOCATION: (1162)..(1162)
<223> OTHER INFORMATION: n = any nucleotide

<400> SEQUENCE: 27

aattcggcac gagannaaaa ggaaaaaaaa acaaaacaca ccaagccaaa taaaagcgac     60

aatgggatcg ctcaccacca acatcgtcct cgccgtcgcc gtggtggcag cgctggtcgg    120

cggcgggtcg tgcggcccgc ccaaggtgcc acccggcccg aacatcacga ccaactacaa    180

cgccccgtgg ctccccgcca gggccacctg gtacggccag ccctacggct ccggctccac    240

cgacaatggt ggcgcgtgcg ggatcaagaa cgtcaacctg cctccctaca acggcatgat    300

ctcctgcggc aacgtcccaa tcttcaagga cggcagggga tgcggctcat gctacgaggt    360

gaagtgtgag cagccggcgg cgtgctcgaa gcagccggtg acggtgttca tcacggacat    420

gaactacgag cccatctcgg cgtaccactt cgacttctcc ggcaaggcgt tcggcgccat    480

ggcttgcccg gggaaggaga ccgagctccg caaggccggc atcatcgaca tgcagttcag    540

gagggtgcgc tgcaagtacc ccggcggcca gaaggtcacc ttccacgtcg agaagggctc    600

caaccccaac tacctcgccg tgctcgtcaa gttcgtcgcc gacgacggtg acgtcatcca    660
```

```
gatggacctc caggaggccg gattgccagc gtggaggccc atgaagctgt cgtggggcgc    720

catctggagg atggacaccg ccacgccact caaggcaccc ttctccattc gcgtcaccac    780

cgagtccggc aagagcctca tcgccaaaga cgtcatcccg gtcaactgga tgccagacgc    840

catctacgta tcaaacgtcc agttctattg agatcggacg gaaacgatcc tcctaattta    900

tttccctatt aatttgttca aatggtttcc ttctataacc tatatttttc ccgttgttag    960

aaatggttcc atttcctcct acagcttact ttaagatagt tgcgcttgta tatctgcgcc   1020

atcttgtaag ttgtaagatg ctgaagaaca ctatgaattc tgagcatctg attctccggg   1080

aagatttact atgataaaca acagtttgat ttactatgtg tgtccccttg tttattgtat   1140

gctatcctaa tacttatgaa angttttgat                                    1170


<210> SEQ ID NO 28
<211> LENGTH: 861
<212> TYPE: DNA
<213> ORGANISM: Oryza sativa
<220> FEATURE:
<221> NAME/KEY: misc_feature
<223> OTHER INFORMATION: TC89985

<400> SEQUENCE: 28

ccacgcgtcc gcccacgcgt ccgcgatcag cagcagcagc agcttgcaca ctcgagctta     60

gcttagcttt tgcaagagag atcgagctag agatggagaa gtcgagcaag atgatggcgg    120

tggcggcggt gctggtgctc gcggtggtcg gcgcggcgga ggcgaggaac atcaaggcgg    180

cggcggcggc ggcggcggag agcaaggaca cggtggtgca gccgacgacg ttcccgccgt    240

tcgaccgctt cgggagcgcg gtgccggcgt tcggcggcat gcccggcagc agcatcccgg    300

ggttcagcct ccccggcagc agcggctcca cccccggcgg cctcggcggc ttcggcagca    360

tgcccatgtt cggcggcctc ggcggcggct cacctggcct cggcggcggc atgcccggct    420

cccccgccgc cgccgacaag caggccaaga agccatgaga gacctcgccg tcgccggcgg    480

cgtcgccgct gctgcgcggg taatgtgctc tatgtagcgc acggcgttgc atgcaatatg    540

gatggctata tgacgcgcgc gcgttatatc ttcatatgtg cagttagctt gcactgtgtc    600

tagctagcgt tctattatga gtagtgtctc ttctatctct tttctttaca tgcatttgga    660

ggaggattat tctatctgtt tgttggttgg ttgtgtttgt ttgttttaat taggtccctt    720

cttatatttt gtgttttaat taagttcgtg atcatgtagt agtactacca ctgtttcgag    780

ctcgaggcat gaataatgct aaatgtgatc attattgtgt tattgtatgg tgatggctat    840

atatattact atctctgctt c                                              861


<210> SEQ ID NO 29
<211> LENGTH: 1252
<212> TYPE: DNA
<213> ORGANISM: Oryza sativa
<220> FEATURE:
<221> NAME/KEY: misc_feature
<223> OTHER INFORMATION: TC89891 (PRO0081)
<220> FEATURE:
<221> NAME/KEY: misc_feature
<222> LOCATION: (5)..(5)
<223> OTHER INFORMATION: n = any nucleotide

<400> SEQUENCE: 29

cccangcgtc cgaaccaatc gactcgcacc accaccagca gctcaagcag caacagctca     60

aacggaggaa gatctcatcg ccatgacgac cggcaatggc gacgcaccgg tgatcaagaa    120

cgcccacagc gacatcgaca gcaccaacaa gacgctgctc aagagcgacg ccctgtacaa    180
```

```
gtatgtcctg gacacgacgg tgctgccacg ggagccggag tgcatgcgcg atctgcgcct    240

catcacggac aagcaccagt gggggttcat gcagtcgtcg gcggatgagg cgcagtgctg    300

gggatgctgc tgaagatggc cggagcgaag aggacaatcg aggtgggtgt cttcaccggc    360

tactcgctgc tggcgacggc gctggcgctg ccggaggacg ggaaggtggt ggcgatcgac    420

ccggacaggg agagctacga gatcgggcgg ccgttcttgg agaaggccgg ggtggcgcac    480

aaggtggact tccgcgaggg gaaggggctg gagaagctgg acgagctgct cgccgaggag    540

gcggcggcgg ggcgcgaggc ggcgttcgac ttcgcgttcg tggacgcgga caagcccaac    600

tacgtcaagt accacgagca gctgctgcag ctggtgcgcg tcggcgggca catcgtgtac    660

gacaacacgc tgtgggccgg cacggtggcg ctgccgccgg acacgccgct gtcggacctg    720

gaccggaggt tctccgtcgc catcagggac ctcaactcca ggctcgccgc cgacccgcgc    780

atcgacgtct gccagctcgc catcgccgac ggcatcacca tctgccgccg cctcgtgtga    840

ggtcgagacc gagaccttac cggccgatcc atccatcgct ctcgcgtgat taattaacgt    900

gtgttgctgt actcttctac tgctacaact atactattac ttccttaatt gccgcttaaa    960

ttttcctata cgtgtttcaa tcaatgagat tattatattc ttcgagcatg agagagacgg   1020

agttgtaggg acatttgatg atggttgtta ctgtactaca tgttgataag tgcaacatct   1080

ctttccatgg ttgctactct actcaccgtg tcatgttggt tgcggatttt gatctcatct   1140

gcaagatgga ctactggggc ccaaaatgga acagactggt ccctcgatcc tgcaggagct   1200

tgcacctgtt gcaagggcct ttttaactgg ctaactaggt gggtaagtag gg           1252
```

```
<210> SEQ ID NO 30
<211> LENGTH: 671
<212> TYPE: DNA
<213> ORGANISM: Oryza sativa
<220> FEATURE:
<221> NAME/KEY: misc_feature
<223> OTHER INFORMATION: TC89670 (PRO0091)
<220> FEATURE:
<221> NAME/KEY: misc_feature
<222> LOCATION: (3)..(3)
<223> OTHER INFORMATION: n = any nucleotide
<220> FEATURE:
<221> NAME/KEY: misc_feature
<222> LOCATION: (14)..(14)
<223> OTHER INFORMATION: n = any nucleotide

<400> SEQUENCE: 30
```

```
gcnggcttcg gcangagttc aaacattata gttgaagcat agtagtagaa tcctacaaaa     60

atgaagatca ttttcgtatt tgctctcctt gctattgttg catgcaacgc ttctgcacgg    120

tttgatgctc ttagtcaaag ttatagacaa tatcaactac aatcgcatct cctgctacag    180

caacaagtgc tcagcccatg cagtgagttc gtaaggcaac agcatagcat agtggcaacc    240

cccttctggc aaccagctac gtttcaattg ataaacaacc aagtcatgca gcaacagtgt    300

tgccaacagc tcaggctggt agcgcaacaa tctcactacc aggccattag tagcgttcag    360

gcgattgtgc agcaactaca gctgcagcag gtcggtgttg tctactttga tcagactcaa    420

gctcaagctc aagctttgct ggccttaaac ttgccatcca tatgtggtat ctatcctaac    480

tactacattg ctccgaggag cattcccacc gttggtggtg tctggtactg aattgtaata    540

gtataatggt tcaaatgtta aaaataaagt catgcatcat catgcgtgac agttgaaact    600

tgatgtcata taaatctaaa taaaatcacc tatttaaata gcattcatgt atgagttcca    660

ttatcatagc t                                                         671
```

<210> SEQ ID NO 31
<211> LENGTH: 436
<212> TYPE: DNA
<213> ORGANISM: Oryza sativa
<220> FEATURE:
<221> NAME/KEY: misc_feature
<223> OTHER INFORMATION: TC89883 (PRO0095)

<400> SEQUENCE: 31

```
cctcgagggt cgacccacgc gtccgctctc ctctcttctc tcgccctcac cgctcgccga     60

ggttgccgtc tccttgtctc ctccgctcct tgcgccgccg ccgcgacgag tcgcggggag    120

gggcggcgat ctccatctcc atctgaggcg aggagagcag gggaggtgag gggatcctgg    180

tgaggtttgt gattactgga caatagaaat atttacacaa tatggctggc ggctctgctg    240

atgcagtgac caaggagatg gaggcgctac tcgttggaca aaatccaaat gcggttagtg    300

gagaaacatg cgagacctca tcaaaagaag gcaaagttgc agatagcaat ggatctcatt    360

cttcaccacc agaagatgat gatgatgaag cgcaagggga tggtccatct caagattgga    420

ggatccagaa gctttc                                                    436
```

<210> SEQ ID NO 32
<211> LENGTH: 860
<212> TYPE: DNA
<213> ORGANISM: Oryza sativa
<220> FEATURE:
<221> NAME/KEY: misc_feature
<223> OTHER INFORMATION: TC90434 (PRO0111)
<220> FEATURE:
<221> NAME/KEY: misc_feature
<222> LOCATION: (1)..(1)
<223> OTHER INFORMATION: n = any nulceotide
<220> FEATURE:
<221> NAME/KEY: misc_feature
<222> LOCATION: (10)..(10)
<223> OTHER INFORMATION: n = any nulceotide

<400> SEQUENCE: 32

```
nagggctaan attaccggag tatttttgca aagggagtaa tcaaagttcc aatacgaaat     60

cgcggtcgta gtagtacaat acaaagacga gttcacggag cgcgtaaact aataaggaaa    120

aattaaacgt cgcggagaaa taatagccga actggatgaa gatgagcagc actgcctctt    180

gcctagccta gcccatcatg gcgaggccga cggccccgac cagcaggccc atcaccgaac    240

gggcctcgct gccgctggcc ccgccggtgc tgcccgtcga cttcgtcgtc gtcgtcgtcg    300

gcgtcgtggt cgcgtccggc gtcgacgagg gcgtgtccat gccggggtcc gatgacggcg    360

tggcgggcgt cgcggtggac ggcggggacg acgacgccgt cggggtgggg gtggtgccgg    420

ccgccgcgga gaccgtgacg gcgagcttca tgccgccgga gcagtggccg ctggtgccgc    480

agatgaagta gcgggtgccg ggcttggtga gcgcgatctt ggtgttctgg tcgctgtagg    540

actggatcga gttgctggcg gacacgcgct gtagtcagcc gagctcacct ccgccaccgt    600

gtgcatcatg ctgtactgga acacgagcga gtcaccaacg ctgaaggttt tgctcttcgc    660

ccaggtatcg tagtccacgc cactgctcca gccggatgtg tcgccgacgg tgtagtccac    720

ggcgaaagcc ggcgcaacgg cggcgaggag tagcaccacc agacctgcag ctgcaagtcc    780

atgtactcca gccatgatgg cagagttaat tagcaaacgc gaactgatta gagccgtact    840

agtactggtg gccctcgtgc                                                860
```

<210> SEQ ID NO 33

<211> LENGTH: 1167
<212> TYPE: DNA
<213> ORGANISM: Oryza sativa
<220> FEATURE:
<221> NAME/KEY: misc_feature
<223> OTHER INFORMATION: TC83072 (PRO0116)

<400> SEQUENCE: 33

```
aggaaaagaa gaaaaaagat cctgtgaacc ctacgaaact accgaagcga acggaaggca     60
ggaatcggcg gcggcggcgg cggcggcggt ggggagaagc catggagcgg ctgcagcgga    120
tcttcggcgc ctccggcatg ggcagccgcc cgtcggactc gccgctgctc gactcctccg    180
agcaggtcta catctcctcc ctcgccctcc tcaagatgct caagcacggg agggccggcg    240
tgccgatgga ggtgatgggg ctgatgctgg gggagttcgt cgacgactac acggtcaggg    300
tggtcgacgt cttcgccatg ccgcagagcg ggaccggggt cagcgtcgag gccgtcgacc    360
atgtcttcca gaccaacatg ctcgacatgc tcaagcagac cgggaggcca gaaatggtgg    420
taggttggta ccattcccat cctggatttg gttgctggct ttcaggagtt gacatcaata    480
ctcaacagag ttttgaagct ttaaacccca gggcagttgc cgtcgtgata gatcccatcc    540
aaagtgtcaa ggggaaagtt gtcattgatg catttcgcct tattaaccct cagaccatga    600
tgcttggtca ggagccacga cagacaacat caaatgttgg gcacctaaat aagccatcta    660
ttcaggctct tattcatggg ctgaacaggc actactattc aattgcaatc aattaccgga    720
aaaatgagct tgaggaaaag atgttactga acttgcacaa aaagaaatgg accgatggat    780
tgattctgaa gaggtttgac actcattcaa agaccaatga gcagactgtt caggaaatgc    840
tgaaccttgc tatcaagtac aacaaggcgg tgcaagagga ggatgagctg ccgcctgaga    900
aattagcgat agcaaatgtg ggacggcaag atgctaagaa gcacttggaa gagcatgtct    960
ccaatttgat gtcatcaaac atagttcaga cgctaggaac catgctcgat acagttgtat   1020
tttagatcac tactgctgtt atcccaacac tgtacccaga gctcgtttat tttttatttt   1080
tttatgttta tcgaagccta ccataattca gtgaacttaa cgccagttac atttgggtta   1140
tgaaagctta ccacttgaca acttcat                                        1167
```

<210> SEQ ID NO 34
<211> LENGTH: 871
<212> TYPE: DNA
<213> ORGANISM: Oryza sativa
<220> FEATURE:
<221> NAME/KEY: misc_feature
<223> OTHER INFORMATION: TC90038 (PRO0117)

<400> SEQUENCE: 34

```
cctagctcct cccgccgccg ccgccgccgc cgccgccgcc tctccactcg agagacccag     60
ccgccgccgc cgccgccgcc gccatgtcgc tgatcgccgg ggaggacttc cagcacatcc    120
tgcgtctgct gaacaccaac gtcgatggga agcagaagat catgttcgcg ctcacctcca    180
tcaagggtgt cggccgcagg ttctccaaca tcgcctgcaa gaaggccgac atcgacatga    240
acaagagggc cggtgagctt acgccggagg agctggagcg gctgatgacc gtggtggcga    300
acccgcggca gttcaaggtg cccgactggt tcctcaacag gaagaaggac tacaaggacg    360
ggaggttctc ccaggttgtc tccaacgcgc tcgacatgaa gctcagggat gatcttgaga    420
ggctcaagaa gatcaggaac caccgtggtc tgaggcacta ctggggcctc cgtgtgcgtg    480
ggcagcacac caagacaacc ggaaggaggg gtaagactgt cggtgtgtcc aagaagcgat    540
aagcctaaga accacccgag acttgatgaa gcgtttcgtt gggtgatgtt ttgccctagg    600
```

```
ataatatttt gcagctatgg aaccttgtcg taatgtatct tgaagagtgt ctttgggaac     660

taagagtaat ttacttttct tgaaactatt gcagtattga ctccttgttt attgcttttc     720

tccactttct tctacccact taaaactatt gcagtatcga ctccttgttt attgctattc     780

tccactggct tctgccttaa ttttggatgt tgcatgcgct gtgtatctgg ttcatgtgat     840

gtacccatgg cagctttgat gcattgggat t                                     871


<210> SEQ ID NO 35
<211> LENGTH: 1245
<212> TYPE: DNA
<213> ORGANISM: Oryza sativa
<220> FEATURE:
<221> NAME/KEY: misc_feature
<223> OTHER INFORMATION: TC82936 (PRO0122)

<400> SEQUENCE: 35

acgcggccaa aacgtaccct tgtgactaca cccgcttcgc ttcctcccct ctctaagccg      60

gggaagctaa gccatggcgt ccgtcaccgc ccgcaccccg gtcgcagccc tccgctcgtc     120

ggcgtcgctc aagtctacct tcctagggca atcctccacc cgcctcgccc gcgcaccgac     180

tacgaggcgt aatgttcggg cggaggccaa gggagagtgg ctccccggcc tcccttctcc     240

cacctacctc aacggcagct tgccaggcga taacgggttc gacccgttgg gtctggcgga     300

ggacccggag aacctgcggt ggttcgtgca ggcggagtgg tgaacgggcg gtgggcgatg     360

ctgggggtgg ccgggatgct gctgcctgag gtgctgacga agatcgggtt gatcgacgcg     420

ccgcagtggt acgacgccgg caaggccacc tacttcgcgt cgtcgtcgac gctgttcgtc     480

atcgagttca tcctgttcca ctacgtggag atccggcggt ggcaggacat caagaaccct     540

ggctgcgtca accaggaccc catcttcaag agctacagcc tcccgccgca cgagtgcggc     600

taccccggca gcgtcttcaa ccccctcaac ttcgagccca ccctcgaggc caaggagaag     660

gagctcgcca acgggaggct ggcgatgctg gcgttcttgg ggttcctggt gcagcacaac     720

gtgacgcaga aggggccctt cgacaacctg ctgcagcacc tgtctgaccc gtggcacaac     780

accatcatcc agacgctgtc aggctgagcg tgtgatcgat ttcatcaggg ccagggcatc     840

tcaaggagct tgatgagttc aggctggtga aaccgatgat tgggcgatgg aagatgttct     900

cttcttgttt cttctttttt tttttgtgga gtatgcatgt ataagatgtt aatgaattgg     960

ggggaggaga gagagagaga tggatgtgat gagattcaga cttactgtgt gtgttgtggt    1020

aattgtttcc tgcatgcatg gatctggatg catgggtgag ggggtgagtt gagtggtgaa    1080

tttctgatgt acagtactac agggggataa actatctcat ggtagcagca gtgttctagc    1140

tatctcatgg tctcgatctt aattatggtg gataaactac gcttaattgc ttgtcaagtg    1200

cttcatttgc gcattgattc agtattgcgt atcgattcaa agacc                    1245


<210> SEQ ID NO 36
<211> LENGTH: 1416
<212> TYPE: DNA
<213> ORGANISM: Oryza sativa
<220> FEATURE:
<221> NAME/KEY: misc_feature
<223> OTHER INFORMATION: TC89839 (PRO0123)

<400> SEQUENCE: 36

cccacgcgtc cgcccacgcg tccgggacac cagaaacata gtacacttga gctcactcca      60

aactcaaaca ctcacaccaa tggctctcca agttcaggcc gcactcctgc cctctgctct     120
```

```
ctctgtcccc aagaagggta acttgagcgc ggtggtgaag gagccggggt tccttagcgt    180

gagcagaagg ccaagaagcc gtcgctggtg gtgagggcgg tggcgacgcg gcgggccggt    240

ggcgagcccc ggcgcgggca cgtcgaaggc ggacgggaag aagacgctgc ggcagggggt    300

ggtggtgatc accggcgcgt cgtcggggct cgggctcgcg gcggcgaagg cgcttggcgg    360

agacggggaa gtggcacgtg gtgatggcgt tccgcgactt tcctgaaggc ggcgacggcg    420

gcgaaggcgg cggggatggc ggcggggagc tacaccgtca tgcacctgga cctcgcctcc    480

ctcgacagcg tccgccagtt cgtggacaac ttccggcgct ccggcatgcc gctcgacgcg    540

ctggtgtgca acgccgcaca tctaccggcc gacggcgcgg caaccgacgt tcaacgccga    600

cgggtacgag atgagcgtcg ggtgaaccca cctgggccac ttcctcctcg cccgcctcat    660

gctcgacgac ctcaagaaat ccgactaccc gtcgcggcgg ctcatcatcc tcggctccat    720

caccggcaac accaacacct tcgccggcaa cgtccctccc aaggccgggc taggcgacct    780

ccgggggctc gccggcgggc tccgcgggca gaacgggtcg gcgatgatcg acggcgcgga    840

gagcttcgac ggcgccaagg cgtacaagga cagcaagatc tgtaacatgc tgacgatgca    900

ggagttccac cggagattcc acgaggagac cgggatcacg ttcgcgtcgc tgtacccggg    960

gtgcatcgcg acgacgggct tgttccgcga gcacatcccg ctgttccggc tgctgttccc   1020

gccgttccag cggttcgtga cgaaggggtt cgtgtcggag gcggagtccg ggaagcggct   1080

ggcgcaggtg gtgggcgacc cgagcctgac caagtccggc gtgtactgga gctggaacaa   1140

ggactcggcg tcgttcgaga accagctctc gcaggaggcc agcgacccgg agaaggccag   1200

gaagctctgg gacctcagcg agaagctcgt cggcctcgtc tgagtttatt atttacccat   1260

tcgtttcaac tgttaatttc ttcggggttt agggggtttc agctttcagt gagagaggcc   1320

tgtcaagtga tgtacaatta gtaatttttt tttacccgac aaatcatgca ataaaaccac   1380

aggcttacat tatcgatttg tccacctaaa ttaagt                             1416
```

<210> SEQ ID NO 37
<211> LENGTH: 1149
<212> TYPE: DNA
<213> ORGANISM: Oryza sativa
<220> FEATURE:
<221> NAME/KEY: misc_feature
<223> OTHER INFORMATION: TC85888 (PRO0133)

<400> SEQUENCE: 37

```
cttctacttc tatcatacca aacaaactag cttaatttgc attgcatcac attgccggcc     60

gccatgagag ctctcgctct cgcggtggtg gccatggcgg tggtggccgt gcgcggcgag    120

cagtgcggca gccaggccgg cggcgcgctc tgccccaact gcctctgctg cagccagtac    180

ggctggtgcg gctccacctc cgattactgc ggcgccggct gccagagcca gtgctccggc    240

ggctgcggcg gcggcccgac cccgccctcc agcggtggcg gcagcggcgt cgcctccatc    300

atatcgccct cgctcttcga ccagatgctg ctccaccgca acgaccaggc gtgcgccgct    360

aagggcttct acacctacga cgccttcgtc gccgccgcca acgcctaccc ggacttcgcc    420

accacccgcg acgccgacac ctgcaagcgc gaggtcgccg ccttcctggc gcagacgtcc    480

cacgagacca ccggcggctg gcccacggcg cccgacggcc cctactcctg gggctactgc    540

ttcaaggagg agaacaacgg caacgccccc acatactgcg agcccaagcc ggagtggccg    600

tgcgccgccg cgaagaagta ctacggccgg ggacccatcc agatcaccta caactacaac    660

tacggccgcg gggcaggcat cggctccgac ctgctcaaca acccggacct ggtggcgtcg    720
```

-continued

```
gacgccagtc tccttcaaga cggcgttctg gttctggatg acgccgcagt cgcccaagcc    780

gtcgtgccac gcggtgatca ccggccagtg gacgccgtcc gccgacgacc aggcggcggg    840

gcgcgttccg ggctacggcg agatcaccaa catcatcaac ggcggtgtgg agtgcgggca    900

cggcgcggac gacaaggtgg ccgaccggat cgggttctac aagcgctact gcgacatgct    960

gggcgtcagc tatggcgata acctggattg ctacaaccag aggccctacc cgccttccta   1020

gttgatattt gatccgagca gacgaataaa atacaatgca cacgagattg tgagactcga   1080

gaaaacatat actacctctg aattttaata catatctcta aaacaaaaaa aaaaaaaaaa   1140

aaaatatac                                                           1149
```

<210> SEQ ID NO 38
<211> LENGTH: 981
<212> TYPE: DNA
<213> ORGANISM: Oryza sativa
<220> FEATURE:
<221> NAME/KEY: misc_feature
<223> OTHER INFORMATION: TC84300 (PRO0151)

<400> SEQUENCE: 38

```
aagaggcaag agcatccgta ttaaccagcc ttttgagact tgagagtgtg tgtgactcga     60

tccagcgtag tttcagttcg tgtgttggtg agtgattcca gccaagtttg cgatggcttc    120

tcagcaggaa cgggctagct accacgccgg cgagaccaag gcccgcgccg aggagaagac    180

ggggcgcatg atgggcacgg cgcaggagaa ggcgcgggag gccaaggaca cggcgtccga    240

cgccgcgggg cgcgcgatgg gcaggggaca cggcgccaag gaggcgacca aggagaaggc    300

gtacgagacc aaggacgcga ccaaggagaa ggcgtacgag gcaaaggacg cggcctccga    360

cgccaccggc cgcgccatgg acaagggccg cggcgccgcg ggcgccacga gggacaaggc    420

gtacgatgcc aaggacaggg cggctgacac ggcgcagtcc gccgccgacc gcgcccgcga    480

cggcgccggg cagaccggga gctacattgg acagaccgcc gaggccgcca agcagaaagc    540

ggccggcgcc gcgcagtacg ccaaggagac cgcgatcgcc ggcaaggaca agaccggcgc    600

cgtgctccag caggcagggg agcaggtgaa gagcgtggcg gtgggggcga aggacgcggt    660

gatgtacacg ctcgggatgt caggcgataa caagaacaac gccgctgccg gcaaggacac    720

cagcacctac aagcctggaa ctgggagtga ctaccagtaa tacggtagaa gaagcatgtg    780

tcgtctttgg cactgatgcc aaagtgtacg tgttgtatcc tctttttaa gtttcagctc     840

gacttcgacg tgttcggtgt cacactttgg tttttcagtt gtgctcaact gttcatgttt    900

ctggttccat ggagggccag tgtggaggtc aatgtttaag ctttcgtttt aaaatctgat    960

aataaagttg gttaagacct g                                              981
```

<210> SEQ ID NO 39
<211> LENGTH: 1203
<212> TYPE: DNA
<213> ORGANISM: Oryza sativa
<220> FEATURE:
<221> NAME/KEY: misc_feature
<223> OTHER INFORMATION: TC89687 (PRO0169)

<400> SEQUENCE: 39

```
tactcctctc tctcacctcc accatctagc tcactcacac agtctccact cacacgcatt     60

gcagaggaga ggcgacaatg gaggggaagg aggaggacgt gcggctgggg gcgaacaggt    120

actcggagag gcagccgata gggacggcgg cgcagggcgc gggggacgac aaggactaca    180

aggagccgcc gccgggccgc tgttcgagcc aggggagctc aagtcgtggt ctttctaccg    240
```

```
ggccgggatc gccgagttcg tcgccacctt cctcttcctc tacatcacca tcctcaccgt    300

catgggggtc tccaagtcct cctccaagtg cgccaccgtc ggcatccagg gcatcgcctg    360

gtccttcgga ggcatgatct tcgcgctcgt ctactgcacc gccggcatct ccggaggaca    420

catcaaccca gcagttactt ttgggctgtt cttggccagg aagctgtccc tgacccgggc    480

catcttctac atagtgatgc aatgcctagg ggccatctgc ggagctggag ttgtgaaggg    540

cttccagcag ggtctgtaca tgggcaatgg cggtggtgcc aatgtagttg ccagtggcta    600

caccaagggt gacggtcttg gtgctgagat tgttggcacc ttcatcctgg tctacaccgt    660

cttctcagcc actgatgcca agaggaatgc cagggactca catgttccta tccttgcccc    720

actgccaatt ggttttgcgg tgttcctggt ccacctggcc accatcccca tcaccggtac    780

tggcatcaac ccagccagga gccttggcgc tgccatcatc tacaacaagg accatgcctg    840

gaatgaccat tggatcttct gggttggtcc cttcgttggc gctgccctgg ctgccatcta    900

ccaccaggtg atcatcaggg cgatcccatt caagagcagg tcttaagccc cgcgccgccg    960

ctgcgcagcc gacgacatgc aacgcaatcg tgatgtcctg tttcccgcgc gctactgctg   1020

cgcatctgtc gattccctct atctctagtc cccaagatgt tttcctatc tgaaccctga   1080

acaactcaat cgtgtaatcc agtactcagt cactgtatgt ttttatgtga tggagatctt   1140

aattcttaag ttatcatctc tgttgctgga aatccggttt cctcttcgtg catgaaccgc   1200

gcc                                                                 1203
```

<210> SEQ ID NO 40
<211> LENGTH: 964
<212> TYPE: DNA
<213> ORGANISM: Oryza sativa
<220> FEATURE:
<221> NAME/KEY: misc_feature
<223> OTHER INFORMATION: TC89846 (PRO0170)

<400> SEQUENCE: 40

```
cccacggttc cgcccacggt ccgcccacgg tccgcttctc ttctctggtg gtgtgggtgt     60

gtccctgtct cccctctcct tcctcctctc ctttcccctc ctctcttccc ccctctcaca    120

agagagagag cgccagactc tccccaggtg aggattcagc catgaagggg gccaaatcca    180

agggcgccgc caagcccgac gccaagttgg ctgtgaagag taagggcgcg gagaagcccg    240

ccgccaaggg caggaagggg aaggccggca aggaccccaa caagcccaag agggctccct    300

ccgctttctt cgtttttatg gaggagttcc gtaaggagtt caaggagaag aaccccaaga    360

ataaatctgt cgctgctgta ggaaaagcag ccggtgatag gtggaaatcc ctgaccgaag    420

cggacaaggc tccctatgta gccaaggcca acaagctcaa ggccgagtac aacaaggcca    480

ttgctgccta caacaagggc gagagcactg ccaagaaggc acccgccaag gaggaagagg    540

aggacgacga ggaggaatct gacaagtcca agtccgaggt caatgatgag gatgacgacg    600

agggcagcga agaggatgaa gacgatgacg agtgagcctt ccagtggaca agatgggagc    660

agcaagacgc taagggcggc gggcgtccta aggagcctat ccatcatcat catcgtctac    720

tagaattatt cagtttcact tcacatcgtg atgttttact ttttctctcg tcctataacg    780

gatagcgctc cttgttggcg ccactggtgg gtgttgtggt gcagccaatg tcttgtctcc    840

accgtcaatg atccgcttgt acctagatta ctctttccat tgtcatcggc taacattgtg    900

ataatatcag tttgcgtatg ttagattaaa ttgtttctaa ttccgtcgtt ttcttcttcc    960

ttgc                                                                 964
```

<210> SEQ ID NO 41
<211> LENGTH: 1542
<212> TYPE: DNA
<213> ORGANISM: Oryza sativa
<220> FEATURE:
<221> NAME/KEY: misc_feature
<223> OTHER INFORMATION: TC82935 (PRO0171)

<400> SEQUENCE: 41

```
cacacctcac acctcaccac catcacctcc tcctcctcct cctcttcctc cgcgcgcgcg      60
agatccaggg agagggagag ggagagatca tggcggggac ggtgacggtg ccgtcggcgt     120
cggtgccgtc gacgccgctg ctcaaggacg agctggacat cgtgatcccg acgatccgca     180
acctggactt cctggagatg tggcggccct tcttccagcc ctaccacctc atcatcgtgc     240
aggacggcga cccgaccaag accatccgcg tccccgaggg cttcgactac gagctctaca     300
accgcaacga catcaaccgg atcctcggcc ccaaggcctc ctgcatctcc ttcaaggact     360
ccgcatgccg ctgcttcggc tacatggtct ccaagaagaa gtacgtcttc accatcgacg     420
acgactgctt cgttgccaag gacccatctg gcaaggacat caatgctctt gagcagcaca     480
tcaagaacct cctcagcccg tccaccccgt tcttcttcaa caccttgtat gatccctacc     540
gcgaaggcgc tgactttgtc cgtggttacc ccttcagcct cagggaggga gccaagactg     600
ctgtctctca cggcctgtgg cttaacatcc ctgactatga tgctcctact cagatggtca     660
agcctcgtga gaggaactcc aggtatgttg atgctgtcat gactgtgccc aagggaacct     720
tgttccccat gtgtggcatg aaccttgctt ttgaccgtga tctcatcggt cctgcaatgt     780
actttggtct catgggtgat ggccagccta ttggtcgcta cgacgacatg tgggctggat     840
ggtgcatgaa ggtcatctgt gaccacctga gcctgggagt gaagactgga ctgccgtaca     900
tctggcacag caaggctagc aacccccttcg tgaacttgaa gaaggaatac aagggcatct     960
tctggcagga ggacatcatc cccttcttcc agaacgccac catccccaag gagtgcgaca    1020
ccgtccagaa gtgctacctc tccctcgccg agcaggtcag ggagaagctc ggcaagatcg    1080
acccctactt cgtcaagctt gccgatgcca tggtcacctg gatcgaggcc tgggatgagc    1140
tgaacccctc gactgctgct gtcgagaacg gcaaggccaa gtagattgat cctgggagct    1200
tgtgtgtcgc aggatggaaa gtacccttta agtgaaagtg ttgctgtggc ctaggccccc    1260
tagatatagc tctttttgag atgaagggag agattactta agcaacttta taattctttg    1320
ttgttatgct ggttcttttg tagctggaaa aggatttgtt atcatcgttt acataattca    1380
agacaataat aattttatca tgtaattttg atagtcgtgc tttggttgct aaatggtgtt    1440
attgtattta ataacctttg caaatcacta tacctgttgg ttgttctgag aattgtatgc    1500
actaccatat tatatttcta aatcatttcg taggcattat gg                        1542
```

<210> SEQ ID NO 42
<211> LENGTH: 1432
<212> TYPE: DNA
<213> ORGANISM: Oryza sativa
<220> FEATURE:
<221> NAME/KEY: misc_feature
<223> OTHER INFORMATION: TC82977 (PRO0173)
<220> FEATURE:
<221> NAME/KEY: misc_feature
<222> LOCATION: (1429)..(1429)
<223> OTHER INFORMATION: n = any nucleotide

<400> SEQUENCE: 42

```
aaaagagcag cgtcgcctct cctcctccct aacccctacg cttccagaac cttctcgaag      60

ctcccgctcc ccccccccctt ccgctccaat ggcgaaggaa ccgatgcgcg tgctcgtcac    120

cggcgccgca ggacaaattg gatatgctct tgtccccatg attgctaggg gtgtgatgtt    180

gggtgctgac cagcctgtta ttctacacat gcttgacatt ccaccagcta ctgaatctct    240

taatggcctt aagatggagc tggttgatgc tgcatttcct cttttgaagg gaattgtcgc    300

aacaactgat gttgtggagg cctgcactgg tgtgaatgtt gcggttatgg ttggtgggtt    360

ccccaggaag gagggaatgg aaaggaagga tgttatgtca aaaaatgtct ccatctacaa    420

atcccaagct tctgctcttg aggctcatgc agcccctaac tgcaaggttc tggtagttgc    480

caatccagca aacaccaacg ctctcatctt aaaagaattc gctccatcca tccctgagaa    540

gaacattact tgcctcaccc gtcttgacca caacagggca cttggccaga tctctgaaaa    600

acttaatgtc caagttactg atgtgaagaa tgcgatcatc tggggcaacc actcatccac    660

ccagtaccct gatgttaacc acgccactgt gaagactccc agtggagaga agcctgtcag    720

ggaactcgtt gctgatgatg agtggttaaa tacggaattc atctctaccg tccagcagcg    780

tggtgccgcc atcatcaagg cgaggaagca atccagtgcc ctatctgctg ccagctctgc    840

atgcgatcac attcgtgact gggttcttgg cactcctgag ggaacatttg tctccatggg    900

tgtgtactct gatggttcgt atggtgtgcc tgctggtctg atctactcgt tcccagtaac    960

atgcagtggt ggcgaatgga cgattgttca gggtctcccg atcgacgagt tctcaaggaa   1020

gaagatggac gcgactgccc aggagctgtc ggaggagaag acgctcgctt actcatgcct   1080

caactaaaac taagcaatac ccagagggac agatagtgag cgattgcccg ctcccgtgtt   1140

tttgaataaa agagactttt aagttccatc acatagaaac tgtttatctc agaccgctgc   1200

acatcgcgag atgtggagcg cagatgccgt tgctggtttt actccagtgt gtattgaggc   1260

tttgtactag ctcccttttt tttgcctggt gattcgcagg acatttgctg aaaacattga   1320

acccatttga catctgatgg aatcatggac cagtagcaag tacatttttg cgaaagcata   1380

atctgcatcg ggcttgggct ggtggttgaa ctttctgcca catggcccnt gg             1432

<210> SEQ ID NO 43
<211> LENGTH: 659
<212> TYPE: DNA
<213> ORGANISM: Oryza sativa
<220> FEATURE:
<221> NAME/KEY: misc_feature
<223> OTHER INFORMATION: TC83646 (PRO0175)

<400> SEQUENCE: 43

gctaagtgag ctagccactg atcagaagaa cacctcgatc tctgagagtg ttttttcagc      60

tttagcttaa gcaggatgga gcaccagggg cagcacggcc acgtgaccag ccgcgtcgac    120

gagtacggca acccggtcgg caccggcgcc ggacacggcc agatgggcac cgccggcatg    180

gggacgcacg gcaccgccgg caccggcggc ggccagttcc agccgatgag ggaggagcac    240

aagaccggcg gcgtcctgca acgctccggc agctccagct caagctcgtc tgaggatgat    300

ggaatgggag ggaggaggaa gaaggggatc aaggagaaga tcaaggagaa gctccccggc    360

ggcaacaagg gcgagcagca gcatgccatg ggcggcaccg gcaccggcac cggcaccggc    420

accggaaccg gcggcgccta cgggcagcag ggccacggca ccgggatgac caccggcacc    480

accggcgcac acggcaccac caccaccgac accggcgaga agaagggcat catggacaag    540

atcaaggaga agctgcccgg ccagcactga gctcgacaca ccaccacacc atgtgtctgc    600
```

```
gcccccggcg accgccgcca cgtcaccttc ctgaataata agatgagcta accgagcgc      659


<210> SEQ ID NO 44
<211> LENGTH: 1310
<212> TYPE: DNA
<213> ORGANISM: Oryza sativa
<220> FEATURE:
<221> NAME/KEY: misc_feature
<223> OTHER INFORMATION: TC90619 (PRO0177)

<400> SEQUENCE: 44

ggaccagcga gcaaccagcc ccccgccccc aatggcggca gagcagcttt gcccaccgct      60

gccgcttttg cccacctctc ctccgattaa tcccctcccc tcctcttcct cccacttctc     120

cgcctcctct tcctcccctc gccgacccta cctactcgcg ccgccgccgt cgcattgggc     180

ggcaaacgga ggggggggtta accctgatgg agcagtacga gaaggaggag aagattgggg    240

agggcacgta cggggtggtg tacagggcgc gggacaaggt caccaacgag acgatcgcgc     300

tcaagaagat ccggcttgag caggaggatg agggcgtccc ctccaccgca atccgcgaga     360

tctcgctcct caaggagatg catcacggca acatcgtcag gttacacgat gttatccaca     420

gtgagaagcg catatatctt gtctttgagt atctggatct ggacctaaag aagttcatgg     480

actcttgtcc agagtttgcg aaaaacccca ctttaattaa gtcatatctc tatcagatac     540

tccgcggcgt tgcttactgt cattctcata gagttcttca tcgagatttg aaacctcaga     600

atttattgat agatcggcgt actaatgcac tgaagcttgc agactttggt ttagccaggg     660

catttggaat tcctgtccgc acgtttactc acgaggttgt aaccttgtgg tatagagctc     720

cagagatcct tcttggatca aggcagtatt ctacaccagt tgatatgtgg tcagttggtt     780

gtatctttgc agaaatggtg aaccagaaac cactgttccc tggtgattct gagattgatg     840

aattatttaa gatattcagg gtactaggaa ctccaaatga acaaagttgg ccaggagtta     900

gctcattacc tgactacaag tctgctttcc ccaagtggca agcacaggat cttgcaacta     960

ttgtccctac tcttgaccct gctggtttgg accttctctc taaaatgctt cggtacgagc    1020

caaacaaaag gatcacagct agacaggctc ttgagcatga atacttcaag gaccttgaga    1080

tggtacaatg accctgctat ggctttacat tggattggca tatgtatggg ctgggctcct    1140

catttcattc cttctgtgaa cgctgtgccc ttcgtttggg catttttgtc attcagctgg    1200

atatttcaaa tcttgtgtgt ttgatatgta ttcaggaacg ctaaatagat caccgtcttg    1260

gtctctattt gttcagagta aatatcttcc aatgctgcct ttcagtttcc               1310


<210> SEQ ID NO 45
<211> LENGTH: 55
<212> TYPE: DNA
<213> ORGANISM: Artificial sequence
<220> FEATURE:
<223> OTHER INFORMATION: prm3780

<400> SEQUENCE: 45

ggggacaagt ttgtacaaaa aagcaggctt cgacgctact caagtggtgg gaggc           55


<210> SEQ ID NO 46
<211> LENGTH: 55
<212> TYPE: DNA
<213> ORGANISM: Artificial sequence
<220> FEATURE:
<223> OTHER INFORMATION: prm2768

<400> SEQUENCE: 46
```

```
ggggacaagt ttgtacaaaa aagcaggctc ccgatttagt agaccacatt ttggc          55


<210> SEQ ID NO 47
<211> LENGTH: 54
<212> TYPE: DNA
<213> ORGANISM: Artificial sequence
<220> FEATURE:
<223> OTHER INFORMATION: prm2420

<400> SEQUENCE: 47

ggggacaagt ttgtacaaaa aagcaggcta tgccatcgag tggtgtgccg atac           54


<210> SEQ ID NO 48
<211> LENGTH: 54
<212> TYPE: DNA
<213> ORGANISM: Artificial sequence
<220> FEATURE:
<223> OTHER INFORMATION: prm2853

<400> SEQUENCE: 48

ggggacaagt ttgtacaaaa aagcaggctt ctcttctgaa gctgaagccc tgcg           54


<210> SEQ ID NO 49
<211> LENGTH: 53
<212> TYPE: DNA
<213> ORGANISM: Artificial sequence
<220> FEATURE:
<223> OTHER INFORMATION: prm2426

<400> SEQUENCE: 49

ggggacaagt ttgtacaaaa aagcaggcta aaaccaccga gggacctgat ctg            53


<210> SEQ ID NO 50
<211> LENGTH: 55
<212> TYPE: DNA
<213> ORGANISM: Artificial sequence
<220> FEATURE:
<223> OTHER INFORMATION: prm2855

<400> SEQUENCE: 50

ggggacaagt ttgtacaaaa aagcaggctc ctagctatat gcagaggttg acagg          55


<210> SEQ ID NO 51
<211> LENGTH: 53
<212> TYPE: DNA
<213> ORGANISM: Artificial sequence
<220> FEATURE:
<223> OTHER INFORMATION: prm3025

<400> SEQUENCE: 51

ggggacaagt ttgtacaaaa aagcaggcta tggtgccatg tcaataagac atc            53


<210> SEQ ID NO 52
<211> LENGTH: 56
<212> TYPE: DNA
<213> ORGANISM: Artificial sequence
<220> FEATURE:
<223> OTHER INFORMATION: prm3029

<400> SEQUENCE: 52

ggggacaagt ttgtacaaaa aagcaggctg tttttctatg aaccggtcat taaacc         56


<210> SEQ ID NO 53
<211> LENGTH: 55
<212> TYPE: DNA
<213> ORGANISM: Artificial sequence
```

<220> FEATURE:
<223> OTHER INFORMATION: prm3061

<400> SEQUENCE: 53

```
ggggacaagt ttgtacaaaa aagcaggctc ctgatggatg atgaatcact gatcg         55
```

<210> SEQ ID NO 54
<211> LENGTH: 57
<212> TYPE: DNA
<213> ORGANISM: Artificial sequence
<220> FEATURE:
<223> OTHER INFORMATION: prm3031

<400> SEQUENCE: 54

```
ggggacaagt ttgtacaaaa aagcaggctt cgttaagttt gatgatttct gatgacc       57
```

<210> SEQ ID NO 55
<211> LENGTH: 53
<212> TYPE: DNA
<213> ORGANISM: Artificial sequence
<220> FEATURE:
<223> OTHER INFORMATION: prm3051

<400> SEQUENCE: 55

```
ggggaccact ttgtacaaga aagctgggtg ccgccgctcg ctcgcttcgt tcg           53
```

<210> SEQ ID NO 56
<211> LENGTH: 58
<212> TYPE: DNA
<213> ORGANISM: Artificial sequence
<220> FEATURE:
<223> OTHER INFORMATION: prm3592

<400> SEQUENCE: 56

```
ggggacaagt ttgtacaaaa aagcaggctc gtgttcatgt tcgcatttag gattggac      58
```

<210> SEQ ID NO 57
<211> LENGTH: 55
<212> TYPE: DNA
<213> ORGANISM: Artificial sequence
<220> FEATURE:
<223> OTHER INFORMATION: prm5131

<400> SEQUENCE: 57

```
ggggacaagt ttgtacaaaa aagcaggctc agatgccaca gtatggtgta ccacc         55
```

<210> SEQ ID NO 58
<211> LENGTH: 56
<212> TYPE: DNA
<213> ORGANISM: Artificial sequence
<220> FEATURE:
<223> OTHER INFORMATION: prm3782

<400> SEQUENCE: 58

```
ggggacaagt ttgtacaaaa aagcaggctt tgcagttgtg accaagtaag ctgagc        56
```

<210> SEQ ID NO 59
<211> LENGTH: 54
<212> TYPE: DNA
<213> ORGANISM: Artificial sequence
<220> FEATURE:
<223> OTHER INFORMATION: prm2844

<400> SEQUENCE: 59

```
ggggacaagt ttgtacaaaa aagcaggctt ttggcgcggg gcagaagagt ggac          54
```

<210> SEQ ID NO 60
<211> LENGTH: 57
<212> TYPE: DNA
<213> ORGANISM: Artificial sequence
<220> FEATURE:
<223> OTHER INFORMATION: prm2973

<400> SEQUENCE: 60
ggggacaagt ttgtacaaaa aagcaggctg cttgagtcat agggagaaaa caaatcg 57

<210> SEQ ID NO 61
<211> LENGTH: 53
<212> TYPE: DNA
<213> ORGANISM: Artificial sequence
<220> FEATURE:
<223> OTHER INFORMATION: prm3770

<400> SEQUENCE: 61
ggggacaagt ttgtacaaaa aagcaggctc gtcctccttt tgtaacggct cgc 53

<210> SEQ ID NO 62
<211> LENGTH: 56
<212> TYPE: DNA
<213> ORGANISM: Artificial sequence
<220> FEATURE:
<223> OTHER INFORMATION: prm3772

<400> SEQUENCE: 62
ggggacaagt ttgtacaaaa aagcaggctc atgcggctaa tgtagatgct cactgc 56

<210> SEQ ID NO 63
<211> LENGTH: 53
<212> TYPE: DNA
<213> ORGANISM: Artificial sequence
<220> FEATURE:
<223> OTHER INFORMATION: prm3774

<400> SEQUENCE: 63
ggggacaagt ttgtacaaaa aagcaggctt agtaccattc ttccctcgtg agc 53

<210> SEQ ID NO 64
<211> LENGTH: 53
<212> TYPE: DNA
<213> ORGANISM: Artificial sequence
<220> FEATURE:
<223> OTHER INFORMATION: pm3776

<400> SEQUENCE: 64
ggggacaagt ttgtacaaaa aagcaggctg tttggttggt gaccgcaatt tgc 53

<210> SEQ ID NO 65
<211> LENGTH: 55
<212> TYPE: DNA
<213> ORGANISM: Artificial sequence
<220> FEATURE:
<223> OTHER INFORMATION: prm3800

<400> SEQUENCE: 65
ggggacaagt ttgtacaaaa aagcaggctg tcaccaccgt catgtacgag gctgc 55

<210> SEQ ID NO 66
<211> LENGTH: 55
<212> TYPE: DNA
<213> ORGANISM: Artificial sequence
<220> FEATURE:
<223> OTHER INFORMATION: prm5135

<400> SEQUENCE: 66
ggggacaagt ttgtacaaaa aagcaggctc agacacctag aatatagaca ttccc 55

<210> SEQ ID NO 67
<211> LENGTH: 55
<212> TYPE: DNA
<213> ORGANISM: Artificial sequence
<220> FEATURE:
<223> OTHER INFORMATION: prm3781

<400> SEQUENCE: 67
ggggaccact ttgtacaaga aagctgggtg atcacaagcg cagctaatca ctagc 55

<210> SEQ ID NO 68
<211> LENGTH: 57
<212> TYPE: DNA
<213> ORGANISM: Artificial sequence
<220> FEATURE:
<223> OTHER INFORMATION: prm2769

<400> SEQUENCE: 68
ggggaccact ttgtacaaga aagctgggtc gtgtagaaaa tcttaacccg aaaatcg 57

<210> SEQ ID NO 69
<211> LENGTH: 55
<212> TYPE: DNA
<213> ORGANISM: Artificial sequence
<220> FEATURE:
<223> OTHER INFORMATION: prm2421

<400> SEQUENCE: 69
ggggaccact ttgtacaaga aagctgggtg gtgaggtgcc ggggaagcga cgttg 55

<210> SEQ ID NO 70
<211> LENGTH: 54
<212> TYPE: DNA
<213> ORGANISM: Artificial sequence
<220> FEATURE:
<223> OTHER INFORMATION: prm2854

<400> SEQUENCE: 70
ggggaccact ttgtacaaga aagctgggtt tcttctttcc cttggaacta accg 54

<210> SEQ ID NO 71
<211> LENGTH: 54
<212> TYPE: DNA
<213> ORGANISM: Artificial sequence
<220> FEATURE:
<223> OTHER INFORMATION: prm2427

<400> SEQUENCE: 71
ggggaccact ttgtacaaga aagctgggtt gtcgctttta tttggcttgg tgtg 54

<210> SEQ ID NO 72
<211> LENGTH: 56
<212> TYPE: DNA
<213> ORGANISM: Artificial sequence
<220> FEATURE:
<223> OTHER INFORMATION: prm2856

<400> SEQUENCE: 72
ggggaccact ttgtacaaga aagctgggtc tctagctcga tctctcttgc aaaagc 56

<210> SEQ ID NO 73

<211> LENGTH: 49
<212> TYPE: DNA
<213> ORGANISM: Artificial sequence
<220> FEATURE:
<223> OTHER INFORMATION: prm3026

<400> SEQUENCE: 73
ggggaccact ttgtacaaga aagctgggtg gcgatgagat cttcctccg 49

<210> SEQ ID NO 74
<211> LENGTH: 59
<212> TYPE: DNA
<213> ORGANISM: Artificial sequence
<220> FEATURE:
<223> OTHER INFORMATION: prm3030

<400> SEQUENCE: 74
ggggaccact ttgtacaaga aagctgggtt tttgtaggat tctactacta tgcttcaac 59

<210> SEQ ID NO 75
<211> LENGTH: 62
<212> TYPE: DNA
<213> ORGANISM: Artificial sequence
<220> FEATURE:
<223> OTHER INFORMATION: prm3062

<400> SEQUENCE: 75
ggggaccact ttgtacaaga aagctgggta ttgtgtaaat atttctattg tccagtaatc 60
ac 62

<210> SEQ ID NO 76
<211> LENGTH: 54
<212> TYPE: DNA
<213> ORGANISM: Artificial sequence
<220> FEATURE:
<223> OTHER INFORMATION: prm3032

<400> SEQUENCE: 76
ggggaccact ttgtacaaga aagctgggtg atggcagagt taattagcaa acgc 54

<210> SEQ ID NO 77
<211> LENGTH: 50
<212> TYPE: DNA
<213> ORGANISM: Artificial sequence
<220> FEATURE:
<223> OTHER INFORMATION: prm3052

<400> SEQUENCE: 77
ggggacaagt ttgtacaaaa aagcaggctc taagggcagc agccattggg 50

<210> SEQ ID NO 78
<211> LENGTH: 60
<212> TYPE: DNA
<213> ORGANISM: Artificial sequence
<220> FEATURE:
<223> OTHER INFORMATION: prm3049

<400> SEQUENCE: 78
ggggaccact ttgtacaaga aagctgggtg gcggcggcgg cggcggcggc ggctgggtct 60

<210> SEQ ID NO 79
<211> LENGTH: 54
<212> TYPE: DNA
<213> ORGANISM: Artificial sequence
<220> FEATURE:
<223> OTHER INFORMATION: prm2195

<400> SEQUENCE: 79
ggggaccact ttgtacaaga aagctgggtc ggcttagaga ggggaggaag cgaa 54

<210> SEQ ID NO 80
<211> LENGTH: 58
<212> TYPE: DNA
<213> ORGANISM: Artificial sequence
<220> FEATURE:
<223> OTHER INFORMATION: prm2197

<400> SEQUENCE: 80
ggggaccact ttgtacaaga aagctgggtt ggtgtgagtg tttgagtttg gagtgagc 58

<210> SEQ ID NO 81
<211> LENGTH: 57
<212> TYPE: DNA
<213> ORGANISM: Artificial sequence
<220> FEATURE:
<223> OTHER INFORMATION: prm2845

<400> SEQUENCE: 81
ggggaccact ttgtacaaga aagctgggtc ggcaatgtga tgcaatgcaa attaagc 57

<210> SEQ ID NO 82
<211> LENGTH: 55
<212> TYPE: DNA
<213> ORGANISM: Artificial sequence
<220> FEATURE:
<223> OTHER INFORMATION: prm2974

<400> SEQUENCE: 82
ggggaccact ttgtacaaga aagctgggtc gcaaacttgg ctggaatcac tcacc 55

<210> SEQ ID NO 83
<211> LENGTH: 54
<212> TYPE: DNA
<213> ORGANISM: Artificial sequence
<220> FEATURE:
<223> OTHER INFORMATION: prm3771

<400> SEQUENCE: 83
ggggaccact ttgtacaaga aagctgggtt gtcgcctctc ctctgcaatg cgtg 54

<210> SEQ ID NO 84
<211> LENGTH: 52
<212> TYPE: DNA
<213> ORGANISM: Artificial sequence
<220> FEATURE:
<223> OTHER INFORMATION: prm3773

<400> SEQUENCE: 84
ggggaccact ttgtacaaga aagctgggtg gctgaatcct gcgagaaggg cg 52

<210> SEQ ID NO 85
<211> LENGTH: 54
<212> TYPE: DNA
<213> ORGANISM: Artificial sequence
<220> FEATURE:
<223> OTHER INFORMATION: prm3775

<400> SEQUENCE: 85
ggggaccact ttgtacaaga aagctgggtg atctctccct ctccctctcc ctgg 54

<210> SEQ ID NO 86

```
<211> LENGTH: 52
<212> TYPE: DNA
<213> ORGANISM: Artificial sequence
<220> FEATURE:
<223> OTHER INFORMATION: prm3777

<400> SEQUENCE: 86

ggggaccact ttgtacaaga aagctgggtt ggagcggaag gggggggga gc          52


<210> SEQ ID NO 87
<211> LENGTH: 57
<212> TYPE: DNA
<213> ORGANISM: Artificial sequence
<220> FEATURE:
<223> OTHER INFORMATION: prm3801

<400> SEQUENCE: 87

ggggaccact ttgtacaaga aagctgggtc actctcagag atcgaggtgt tcttctg     57


<210> SEQ ID NO 88
<211> LENGTH: 52
<212> TYPE: DNA
<213> ORGANISM: Artificial sequence
<220> FEATURE:
<223> OTHER INFORMATION: prm5136

<400> SEQUENCE: 88

ggggaccact ttgtacaaga aagctgggtc gcccgcagct cgcccccgtc cg          52
```

RICE PROMOTERS

This application is a divisional patent application of U.S. application Ser. No. 10/525,647 filed Feb. 4, 2004, now U.S. Pat. No. 7,427,676.

The present invention relates to the field of plant molecular biology, more particularly to nucleic acid sequences useful for driving and/or regulating expression of an operably linked nucleic acid in plants. The isolation of these nucleic acid sequences from rice, as well as their use in driving and/or regulating expression of an operably linked nucleic acid is disclosed. The present invention therefore concerns promoters, hybrid promoters, genetic constructs, expression cassettes, transformation vectors, expression vectors, host cells and transgenic plants comprising the isolated nucleic acids according to the present invention. The present invention also concerns methods for driving and/or regulating expression of a nucleic acid and methods for the production of transgenic plants.

Gene expression is dependent on initiation of transcription, which is mediated via the transcription initiation complex. Gene expression is also dependent on regulation of transcription, which regulation determines how strong, when or where a gene is expressed. Said regulation of gene expression may be mediated via transcriptional control elements, which are generally embedded in the nucleic acid sequence 5'-flanking or upstream of the expressed gene. This upstream nucleic acid region is often referred to as a "promoter" since it promotes the binding, formation and/or activation of the transcription initiation complex and therefore is capable of driving and/or regulating expression of the 3' downstream nucleic acid sequence.

Genetic engineering of plants with the aim of obtaining a useful plant phenotype, often involves heterologous gene expression, which is generally mediated by a promoter capable of driving and/or regulating expression of an operably linked heterologous nucleic acid. The phenotype of the host plant only depends on the contribution of the heterologous nucleic acid, but also on the contribution of the specific expression pattern of the chosen promoter determining how, where and when that heterologous nucleic acid is expressed. Accordingly, the choice of promoter with a suitable expression pattern is of crucial importance for obtaining the suitable phenotype. A person skilled in the art will need to have available different promoters, to determine the optimal promoter for a particular nucleic acid. For many different host plants, this availability is rather limited and there is therefore a continuing need to provide new promoters with various expression profiles.

The nucleic acids as presented in SEQ ID NO 1 to 22 were isolated from *Oryza sativa* and have been found to be capable of driving and regulating expression of an operably linked nucleic acid; their expression patterns have also been characterized. Therefore the present invention offers a collection of hitherto unknown isolated nucleic acids, which isolated nucleic acids are useful as promoters.

Accordingly, the present invention provides an isolated promoter capable of driving and/or regulating expression, comprising:

(a) an isolated nucleic acid as given in any one of SEQ ID NO 1 to 22 or the complement of any one of SEQ ID NO 1 to 22; or (b) an isolated nucleic acid having at least 90% sequence identity with any of the DNA sequences as given in any one of SEQ ID NO 1 to 22; or (c) an isolated nucleic acid specifically hybridizing under stringent conditions with any of the DNA sequences as given in any one of SEQ ID NO 1 to 22; or (d) an isolated nucleic acid as defined in any one of (a) to (c), which is interrupted by an intervening sequence; or (e) a fragment of any of the nucleic acids as defined in (a) to (d), which fragment is capable of driving and/or regulating expression.

The term "isolated" as used herein means being removed from its original source. Preferably, the "isolated" promoter is free of sequences (such as protein encoding sequences or other sequences at the 3' end) that naturally flank the promoter in the genomic DNA of the organism from which the promoter is derived. Further preferably, the "isolated" promoter is also free of sequences that naturally flank it at the 5' end. Further preferably, the "isolated" promoter may comprise less than about 5 kb, 4 kb, 3 kb, 2 kb, 1.5 kb, 1.2 kb, 1 kb, 0.8 kb, 0.5 kb or 0.1 kb of nucleotide sequences that naturally occur with the promoter in genomic DNA from the organism of which the promoter is derived.

The present invention is not limited to the nucleic acids as presented by SEQ ID NO 1 to 22. A person skilled in the art will recognize that variants or fragments of a nucleic acid may occur, whilst maintaining the same functionality. These variants or fragments may be man made (e.g. by genetic engineering) or may even occur in nature. Therefore the present invention extends to variant nucleic acids and fragments of any of SEQ ID NO 1 to 22, which variants or fragments are useful in the methods of the present invention. Such variants and fragments include:

(a) an isolated nucleic acid as given in any one of SEQ ID NO 1 to 22 or the complement of any one of SEQ ID NO 1 to 22; or (b) an isolated nucleic acid having at least 90% sequence identity with any of the DNA sequences as given in any one of SEQ ID NO 1 to 22; or (c) an isolated nucleic acid specifically hybridizing under stringent conditions with any of the DNA sequences as given in any one of SEQ ID NO 1 to 22; or (d) an isolated nucleic acid as defined in any one of (a) to (c), which is interrupted by an intervening sequence; or (e) a fragment of any of the nucleic acids as defined in (a) to (d), which fragment is capable of driving and/or regulating expression.

Suitable variants of any one of SEQ ID NO 1 to 22 encompass homologues which have in increasing order of preference at least 90%, 91%, 92%, 93%, 94%, 95%, 96%, 97%, 98% or 99% sequence identity with any one of the nucleic acids as represented in SEQ ID NO 1 to 22.

The percentage of identity may be calculated using an alignment program. Preferably a pair wise global alignment program may be used, which implements the algorithm of Needleman-Wunsch (J. Mol. Biol. 48: 443-453, 1970). This algorithm maximizes the number of matches and minimizes the number of gaps. Such programs are for example GAP, Needle (EMBOSS package), stretcher (EMBOSS package) or Align X (Vector NTI suite 5.5) and may use the standard parameters (for example gap opening penalty 15 and gap extension penalty 6.66). Alternatively, a local alignment program implementing the algorithm of Smith-Waterman (Advances in Applied Mathematics 2, 482-489 (1981)) may be used. Such programs are for example Water (EMBOSS package) or matcher (EMBOSS package). "Sequence identity" as used herein is preferably calculated over the entire length of the promoters as represented by any one of SEQ ID NO 1 to 22. The length of these promoters is presented in Table 2.

Search and identification of homologous nucleic acids, would be well within the realm of a person skilled in the art. Such methods involve screening sequence databases with the sequences provided by the present invention, for example any one of SEQ ID NO 1 to 22, preferably in a computer readable form. Useful sequence databases include but are not limited to Genbank, the European Molecular Biology Laboratory Nucleic acid Database (EMBL) or versions thereof, or the MIPS database. Different search algorithms and software for the alignment and comparison of sequences are well known in the art. Such software includes, for example GAP, BESTFIT, BLAST, FASTA and TFASTA. Preferably BLAST software is used, which calculates percent sequence identity and performs a statistical analysis of the similarity between the sequences. The suite of programs referred to as BLAST programs has 5 different implementations: three designed for nucleotide sequence queries (BLASTN, BLASTX, and TBLASTX) and two designed for protein sequence queries (BLASTP and TBLASTN) (Coulson, Trends in Biotechnology: 76-80, 1994; Birren et al., GenomeAnalysis, 1: 543, 1997). The software for performing BLAST analysis is publicly available through the National Centre for Biotechnology Information.

The sequences of the genome of *Arabidopsis thaliana* and the genome of *Oryza sativa* are now available in public databases such as Genbank. Other genomes are currently being sequenced. Therefore, it is expected that as more sequences of the genomes of other plants become available, homologous promoters may be identifiable by sequence alignment with any one of SEQ ID NO 1 to SEQ ID NO 22. The skilled person will readily be able to find homologous promoters from other plant species, for example from other crop plants, such as maize. Homologous promoters from other crop plants are especially useful for practising the methods of the present invention in crop plants.

One example of homologues having at least 90% sequence identity with any one of SEQ ID NO to 22 are allelic variants of any one of SEQ ID NO 1 to 22. Allelic variants are variants of the same gene occurring in two different individuals of the same species and usually allelic variants differ by slight sequence changes. Allelic variants may encompass Single Nucleotide Polymorphisms (SNPs) as well as Small Insertion/Deletion Polymorphisms (INDELs). The size of INDELs is usually less than 100 bp. SNPs and INDELs form the largest set of sequence variants in naturally occurring polymorphic strains of most organisms.

Homologues suitable for use in the methods according to the invention may readily be isolated from their source organism via the technique of PCR or hybridization. Their capability of driving and/or regulating expression may readily be determined, for example, by following the methods described in the Examples section by simply substituting the sequence used in the actual Example with the homologue.

Other suitable variants of any one of SEQ ID NO 1 to 22 encompassed by the present invention are nucleic acids specifically hybridising under stringent conditions to any one of the nucleic acids of SEQ ID NO 1 to 22. The term "hybridising" means annealing to substantially homologous complementary nucleotide sequences in a hybridization process. Tools in molecular biology relying on such a hybridization process include the polymerase chain reaction (PCR; and all methods based thereon), subtractive hybridisation, random primer extension, nuclease S1 mapping, primer extension, reverse transcription, cDNA synthesis, differential display of RNAs, and DNA sequence determination, Northern blotting (RNA blotting), Southern blotting (DNA blotting). The hybridisation process can also occur with one of the complementary nucleic acids immobilised to a matrix such as magnetic beads, Sepharose beads or any other resin. Tools in molecular biology relying on such a process include the isolation of poly (A+) mRNA. The hybridisation process can furthermore occur with one of the complementary nucleic acids immobilised to a solid support such as a nitro-cellulose or nylon membrane or immobilised by e.g. photolithography to, for example, a siliceous glass support (the latter known as nucleic acid arrays or microarrays or as nucleic acid chips). Tools in molecular biology relying on such a process include RNA and DNA gel blot analysis, colony hybridisation, plaque hybridisation, in situ hybridisation and microarray hybridisation. In order to allow hybridisation to occur, the nucleic acid molecules are generally thermally or chemically denatured to melt a double strand into two single strands and/or to remove hairpins or other secondary structures from single stranded nucleic acids. The stringency of hybridisation is influenced by conditions such as temperature, salt concentration and hybridisation buffer composition. Conventional hybridisation conditions are described in, for example, Sambrook (2001) Molecular Cloning: a laboratory manual, 3rd Edition Cold Spring Harbor Laboratory Press, CSH, New York, but the skilled craftsman will appreciate that numerous different hybridisation conditions can be designed in function of the known or the expected homology and/or length of the nucleic acid sequence. High stringency conditions for hybridisation include high temperature and/or low sodium/salt concentration (salts include sodium as for example in NaCl and $Na_3$-citrate) and/or the inclusion of formamide in the hybridisation buffer and/or lowering the concentration of compounds such as SDS (sodium dodecyl sulphate detergent) in the hybridisation buffer and/or exclusion of compounds such as dextran sulphate or polyethylene glycol (promoting molecular crowding) from the hybridisation buffer. Specifically hybridising under stringent conditions means that the sequences have to be very similar. Specific hybridization under stringent conditions is preferably carried out at a temperature of 60° C. followed by washes in 0.1 to 1×SSC, 0.1×SDS, and 1×SSC, 0.1×SDS.

The invention also relates to a nucleic acid molecule of at least 15 nucleotides in length hybridizing specifically with any of the nucleic acids of the invention. The invention also relates to a nucleic acid molecule of at least 15 nucleotides in length specifically amplifying a nucleic acid of the invention by polymerase chain reaction.

Another variant of any of SEQ ID NO 1 to 22 encompassed by the present invention are nucleic acids corresponding to any one of SEQ ID NO 1 to 22 or variants thereof as described hereinabove, which are interrupted by an intervening sequence. For example, any of the nucleic acids as presented in SEQ ID NO 1 to 22 may be interrupted by an intervening sequence. With "intervening sequences" is meant any nucleic acid or nucleotide, which disrupts another sequence. Examples of intervening sequences comprise introns, nucleic acid tags, T-DNA and mobilizable nucleic acids sequences such as transposons or nucleic acids that can be mobilized via recombination. Examples of particular transposons comprise Ac (activator), Ds (Dissociation), Spm (suppressor-Mutator) or En. The introduction of introns into promoters is now widely applied. The methods according to the present invention may also be practised using a nucleic acid sequence according to any one of SEQ ID NO 1 to 22 provided with an intron. In case the intervening sequence is an intron, alternative splice variants of the nucleic acids according to the invention may arise. The term "alternative splice variant" as used herein encompasses variants of a nucleic acid sequence in which intervening introns have been excised, replaced or added. Such splice variants may be found in nature or may be manmade. Methods for making such promoters with an intron or for making the corresponding splice variants are well known in the art.

Variants interrupted by an intervening sequence, suitable for use in the methods according to the invention may readily be determined for example by following the methods described in the Examples section by simply substituting the sequence used in the actual Example with the variant.

The variant nucleic acids as described hereinabove may be found in nature (for example allelic variants or splice variants). Additionally and/or alternatively, variants of any one of SEQ ID NO 1 to 22 as described hereinabove may be manmade via techniques well known in the art involving for example mutation, substitution, insertion, deletions or derivation. The present invention also encompasses such variants, as well as their use in the methods of the present invention.

A "mutation variant" of a nucleic acid may readily be made using recombinant DNA manipulation techniques or nucleotide synthesis. Examples of such techniques include site directed mutagenesis via M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols. Alternatively, the nucleic acid of the present invention may be randomly mutated.

A "substitutional variant" refers to those variants in which at least one residue in the nucleic acid sequence has been removed and a different residue inserted in its place. Nucleic acid substitutions are typically of single residues, but may be clustered depending upon functional constraints placed upon the nucleic acid sequence; insertions usually are of the order of about 1 to about 10 nucleic acid residues, and deletions can range from about 1 to about 20 residues.

An "insertional variant" of a nucleic acid is a variant in which one or more nucleic acid residues are introduced into a predetermined site in that nucleic acid. Insertions may comprise 5'-terminal and/or 3'-terminal fusions as well as intra-sequence insertions of single or multiple nucleotides. Generally, insertions within the nucleic acid sequence will be smaller than 5'- or 3'-terminal fusions, of the order of about 1 to 10 residues. Examples of 5'- or 3'-terminal fusions include the coding sequences of binding domains or activation domains of a transcriptional activator as used in the yeast two-hybrid system or yeast one-hybrid system, or of phage coat proteins, $(histidine)_6$-tag, glutathione S-transferase-tag, protein A, maltose-binding protein, dihydrofolate reductase, Tag•100 epitope, c-myc epitope, FLAG®-epitope, lacZ, CMP (calmodulin-binding peptide), HA epitope, protein C epitope and VSV epitope.

The term "derivative" of a nucleic acid may comprise substitutions, and/or deletions and/or additions of naturally and non-naturally occurring nucleic acid residues compared to the natural nucleic acid. Derivatives may, for example, comprise methylated nucleotides, or artificial nucleotides.

Also encompassed with in the present invention are promoters, comprising a fragment of any of the nucleic acids as presented by any one of SEQ ID NO 1 to 22 or variants thereof as described hereinabove. A "fragment" as used herein means a portion of a nucleic acid sequence. Suitable fragments useful in the methods of the present invention are functional fragments, which retain at least one of the functional parts of the promoter and hence are still capable of driving and/or regulating expression. Examples of functional fragments of a promoter include the minimal promoter, the upstream regulatory elements, or any combination thereof.

Suitable fragments may range from at least about 20 base pairs or about 50, 100, 150, 200, 250, 300, 350, 400, 450, 500, 550, 600, 650, 700, 750, 800, 850, 900, 950 or 1000 base pairs, up to about the full length sequence of the invention. These base pairs are typically immediately upstream of the transcription initiation start, but alternatively may be from anywhere in the promoter sequence.

Suitable fragments useful in the methods of the present invention may be tested for their capability of driving and/or regulating expression by standard techniques well known to the skilled person, or by the following method described in the Example section.

The promoters as disclosed in any one of SEQ ID NO 1 to 22 are isolated as nucleic acids of approximately 1.2 kb from the upstream region of particular rice coding sequences (CDS). These nucleic acids may include typical elements of a promoter, which are presented in FIG. 1. Generally, a promoter may comprises from coding sequence to the upstream direction: (i) an 5'UTR of pre-messenger RNA, (ii) a minimal promoter comprising the transcription initiation element (INR) and more upstream a TATA box, and (iii) may contain regulatory elements that determine the specific expression pattern of the promoter.

The term "promoter" as used herein is taken in a broad context and refers to regulatory nucleic acid sequences capable of effecting (driving and/or regulating) expression of the sequences to which they are operably linked. A "promoter" encompasses transcriptional regulatory sequences derived from a classical genomic gene. Usually a promoter comprises a TATA box, which is capable of directing the transcription initiation complex to the appropriate transcription initiation start site. However, some promoters do not have a TATA box (TATA-less promoters), but are still fully functional for driving and/or regulating expression. A promoter may additionally comprise a CCAAT box sequence and additional regulatory elements (i.e. upstream activating sequences or cis-elements such as enhancers and silencers). A "promoter" may also include the transcriptional regulatory sequences of a classical prokaryotic gene, in which case it may include a −35 box sequence and/or a −10 box transcriptional regulatory sequences.

"Driving expression" as used herein means promoting the transcription of a nucleic acid.

"Regulating expression" as used herein means influencing the level, time or place of transcription of a nucleic acid. The promoters of the present invention may thus be used to increase, decrease or change in time and/or place transcription of a nucleic acid. For example, they may be used to limit the transcription to certain cell types, tissues or organs, or during a certain period of time, or in response to certain environmental conditions.

The promoter is preferably a plant-expressible promoter. The term "plant-expressible" means being capable of regulating expression in a plant, plant cell, plant tissue and/or plant organ. Accordingly, the invention encompasses an isolated nucleic acid as mentioned above, capable of regulating transcription of an operably linked nucleic acid in a plant or in one or more particular cells, tissues or organs of a plant.

The expression pattern of the promoters according to the present invention were studied in detail and it was found that many of them were tissue-specific. Accordingly, the present invention provides "tissue-specific" promoters. The term "tissue-specific" shall be taken to indicate that expression is predominantly in a particular tissue, tissue-type, organ or any other part of the organism, albeit not necessarily exclusively in said tissue, tissue-type, organ or other part. Accordingly, the invention encompasses an isolated nucleic acid as mentioned above, capable of driving and/or regulating expression (of an operably linked nucleic acid) in a tissue-specific manner. Expression may be driven and/or regulated in the seed, embryo, scutellum, aleurone, endosperm, leaves, flower, calli, meristem, shoot meristem, discriminating centre, shoot, shoot meristem and root. In grasses the shoot meristem is located in the so-called discrimination zone from where the shoot and the leaves originate.

A tissue-specific promoter is one example of a so-called “regulated promoter”. These promoters are regulated by endogenous signals such as the presence of certain transcription factors, metabolites, plant hormones, or exogenous signals, such as ageing, stresses or nutritional status. These regulations may have an effect on one or more different levels such spatial specificity or temporal specificity. Encompassed within the present invention is a nucleic acid as described hereinabove, which is a “regulated promoter”. Examples of regulated promoters are cell-specific promoters, tissue-specific promoters, organ-specific promoters, cell cycle-specific promoters, inducible promoters or young tissue-specific promoters.

Alternatively and/or additionally, some promoters of the present invention display a constitutive expression pattern. Accordingly, the present invention provides a promoter as described hereinabove, which is a constitutive promoter. The term “constitutive” means having no or very few spatial or temporal regulations. The term “constitutive expression” as used herein refers to a substantially continuously expression in substantially all tissues of the organism. The skilled craftsman will understand that a “constitutive promoter” is a promoter that is active during most, but not necessarily all, phases of growth and development of the organism and throughout most, but not necessarily all, parts of an organism.

The “expression pattern” of a promoter is not only influenced by the spatial and temporal aspects, but also by the level of expression. The level of expression is determined by the so-called “strength” of a promoter. Depending on the resulting expression level, a distinction is made herein between “weak” or “strong” promoters. Generally by “weak promoter” is meant a promoter that drives expression of an operably linked nucleic acid at levels of about 1/10000 transcripts to about 1/100000 transcripts to about 1/500000 transcripts. Generally, by “strong promoter” is meant a promoter that drives expression at levels of about 1/10 transcripts, to about 1/100 or to about 1/1000 transcripts.

According to a particular embodiment, the invention provides an isolated promoter as mentioned hereinabove, which is a hybrid promoter. The term “hybrid promoter” as used herein refers to a chimeric promoter made, for example, synthetically, for example by genetic engineering. Preferred hybrid promoters according to the present invention comprise a part, preferably a functional part, of one of the promoters according to the present invention and at least another part, preferably a functional part of a promoter. The latter part, may be a part of any promoter, including any one of the promoters according to the present invention and other promoters. One example of a hybrid promoter comprises regulatory element(s) of a promoter according to the present invention combined with the minimal promoter of another promoter. Another example of a hybrid promoter is a promoter comprising additional regulatory elements to further enhance its activity and/or to alter its spatial and/or temporal expression pattern.

The present invention also provides use of a functional fragment of any one of SEQ ID NO 1 to 22 or variant thereof for changing the expression pattern of a promoter. In such methods, at least part of any of the nucleic acids according to the present invention are combined with at least one fragment of another promoter.

Further, the invention provides a genetic construct comprising:

(a) An isolated promoter as defined hereinabove (b) A heterologous nucleic acid sequence operably linked to isolated promoter of (a), and optionally (c) A 3' transcription terminator The term “genetic construct” as used herein means a nucleic acid made by genetic engineering.

The term “operably linked” to a promoter as used herein means that the transcription is driven and/or regulated by that promoter. A person skilled in the art will understand that being operably linked to a promoter preferably means that the promoter is positioned upstream (i.e. at the 5'-end) of the operably linked nucleic acid. The distance to the operably linked nucleic acid may be variable, as long as the promoter of the present invention is capable of driving and/or regulating the transcription of the operably linked nucleic acid. For example, between the promoter and the operably linked nucleic acid, there might be a cloning site, an adaptor, a transcription or translation enhancer.

The operably linked nucleic acid may be any coding or non-coding nucleic acid. The operably linked nucleic acid may be in the sense or in the anti-sense direction. Typically in the case of genetic engineering of host cells, the operably linked nucleic acid is to be introduced into the host cell and is intended to change the phenotype of the host cell. Alternatively, the operably linked nucleic acid is an endogenous nucleic acid from the host cell.

The term “heterologous” as used herein is intended to be “heterologous to the promoter of the present invention”. A nucleic acid that is heterologous to the promoter of the present invention is not naturally occurring in the nucleic acid sequences flanking the promoter of the present invention when it is in its biological genomic environment. While the nucleic acid may be heterologous to the promoter of the present invention, it may be homologous or native or heterologous or foreign to the plant host cell. The heterologous operably linked nucleic acid may be any nucleic acid (for example encoding any protein), provided that it comprises or it is flanked by at least one nucleotide which is normally not flanking the promoter of the present invention.

The term “transcription terminator” as used in (c) refers to a DNA sequence at the end of a transcriptional unit which signals termination of transcription. Terminators are 3'-non-translated DNA sequences usually containing a polyadenylation signal, which facilitates the addition of polyadenylate sequences to the 3'-end of a primary transcript. Terminators active in and/or isolated from viruses, yeasts, moulds, bacteria, insects, birds, mammals and plants are known and have been described in literature. Examples of terminators suitable for use in the genetic constructs of the present invention include the *Agrobacterium tumefaciens* nopaline synthase (NOS) gene terminator, the *Agrobacterium tumefaciens* octopine synthase (OCS) gene terminator sequence, the Cauliflower mosaic virus (CaMV) 35S gene terminator sequence, the *Oryza sativa* ADP-glucose pyrophosphorylase terminator sequence (t3'Bt2), the *Zea mays* zein gene terminator sequence, the rbcs-1A gene terminator, and the rbcs-3A gene terminator sequences, amongst others.

The present invention also provides an expression cassette, a transformation vector or a plant expression vector comprising a genetic construct as described above.

An “expression cassette” as meant herein refers to a minimal genetic construct necessary for expression of a nucleic acid. A typical expression cassette comprises a promoter-gene-terminator combination. An expression cassette may additionally comprise cloning sites, for example Gateway™ recombination sites or restriction enzyme recognition sites, to allow easy cloning of the operably linked nucleic acid or to allow the easy transfer of the expression cassette into a vector. An expression cassette may further comprise 5' untranslated regions, 3' untranslated regions, a selectable marker, transcription enhancers or translation enhancers.

With “transformation vector” is meant a genetic construct, which may be introduced in an organism by transformation and may be stably maintained in said organism. Some vectors may be maintained in for example *Escherichia coli, A. tumefaciens, Saccharomyces cerevisiae* or *Schizosaccharomyces pombe*, while others such as phagemids and cosmid vectors, may be maintained in bacteria and/or viruses. Transformation vectors may be multiplied in their host cell and may be isolated again therefrom to be transformed into another host cell. Vector sequences generally comprise a set of unique sites recognized by restriction enzymes, the multiple cloning site (MCS), wherein one or more non-vector sequence(s) can be inserted. Vector sequences may further comprise an origin of replication which is required for maintenance and/or replication in a specific host cell. Examples of origins of replication include, but are not limited to, the f1-ori and colE1.

“Expression vectors” form a subset of transformation vectors, which, by virtue of comprising the appropriate regulatory sequences, enable expression of the inserted non-vector sequence(s). Expression vectors have been described which are suitable for expression in bacteria (e.g. *E. coli*), fungi (e.g. *S. cerevisiae, S. pombe, Pichia pastoris*), insect cells (e.g. baculoviral expression vectors), animal cells (e.g. COS or CHO cells) and plant cells. One suitable expression vector according to the present invention is a plant expression vector, useful for the transformation of plant cells, the stable integration in the plant genome, the maintenance in the plant cell and the expression of the non-vector sequences in the plant cell.

Typically, a plant expression vector according to the present invention comprises a nucleic acid of any one of SEQ ID NO 1 to 22 or a variant thereof as described hereinabove, optionally operably linked to a second nucleic acid. Typically, a plant expressible vector according to the present invention, further comprises T-DNA regions for stable integration into the plant genome (for example the left border and the right border regions of the Ti plasmid).

The genetic constructs of the invention may further comprise a “selectable marker”. As used herein, the term “selectable marker” includes any gene, which confers a phenotype to a cell in which it is expressed, to facilitate the identification and/or selection of cells that are transfected or transformed. Suitable markers may be selected from markers that confer antibiotic or herbicide resistance. Cells containing the genetic construct will thus survive antibiotics or herbicide concentrations that kill untransformed cells. Examples of selectable marker genes include genes conferring resistance to antibiotics (such as nptII encoding neomycin phosphotransferase capable of phosphorylating neomycin and kanamycin, or hpt encoding hygromycin phosphotransferase capable of phosphorylating hygromycin), to herbicides (for example bar which provides resistance to Basta; aroA or gox providing resistance against glyphosate), or genes that provide a metabolic trait (such as manA that allows plants to use mannose as sole carbon source). Visual marker genes result in the formation of colour (for example beta-glucuronidase, GUS), luminescence (such as luciferase) or fluorescence (Green Fluorescent Protein, GFP, and derivatives thereof). Further examples of suitable selectable marker genes include the ampicillin resistance (Ampr), tetracycline resistance gene (Tcr), bacterial kanamycin resistance gene (Kanr), phosphinothricin resistance gene, and the chloramphenicol acetyltransferase (CAT) gene, amongst others.

Furthermore, the present invention encompasses a host cell comprising an isolated promoter, or a genetic construct, or an expression cassette, or a transformation vector or an expression vector according to the invention as described hereinabove. In particular embodiments of the invention, the host cell is selected from bacteria, algae, fungi, yeast, plants, insect or animal host cells.

In one particular embodiment, the invention provides a transgenic plant cell comprising an isolated promoter according to the invention, or an isolated nucleic acid, or a genetic construct, or an expression cassette, or a transformation vector or an expression vector according to the invention as described hereinabove. Preferably said plant cell is a dicot plant cell or a monocot plant cell, more preferably a cell of any of the plants as mentioned herein. Preferably, in the transgenic plant cell according to the invention, the promoter or the genetic construct of the invention is stably integrated into the genome of the plant cell.

The invention also provides a method for the production of a transgenic plant, comprising:

(a) Introducing into a plant cell an isolated promoter, for example any one of SEQ ID NO 1 to SEQ ID NO 22, or a variant or fragment thereof, or a genetic construct, or an expression cassette, or a transformation vector or an expression vector according to the present invention and as described hereinabove, and (b) Cultivating said plant cell under conditions promoting plant growth.

“Introducing” the above mentioned isolated promoter, or genetic construct, or expression cassette, or transformation vector or expression vector, into a host cell (e.g. plant cell) is preferably achieved by transformation. The term “transformation” as used herein encompasses the transfer of an exogenous polynucleotide into a host cell, irrespective of the method used for transfer. In particular for plants, tissues capable of clonal propagation, whether by organogenesis or embryogenesis, are suitable to be transformed with a genetic construct of the present invention and a whole plant may be regenerated therefrom. The particular tissue chosen will vary depending on the clonal propagation systems available for, and best suited to, the particular plant species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a plant cell and may be maintained non-integrated, for example, as a plasmid. Alternatively, it may be integrated into the plant genome.

Transformation of a plant species is now a fairly routine technique. Advantageously, any of several transformation methods may be used to introduce the nucleic acids of the invention into a suitable ancestor cell. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., 1882, Nature 296, 72-74; Negrutiu I. et al., June 1987, Plant Mol. Biol. 8, 363-373); electroporation of protoplasts (Shillito R. D. et al., 1985 Bio/Technol 3, 1099-1102); microinjection into plant material (Crossway A. et al., 1986, Mol. Gen Genet 202, 179-185); DNA or RNA-coated particle bombardment (Klein T. M. et al., 1987, Nature 327, 70) infection with (non-integrative) viruses and the like. A preferred transformation method for the production of transgenic plant cells according to the present invention, is an *Agrobacterium* mediated transformation method.

Transgenic rice plants comprising any one of the promoters of the present invention are preferably produced via *Agrobacterium*-mediated transformation using any of the well-known methods for rice transformation, such as the ones described in any of the following: published European patent application EP 1198985 A1, Aldemita and Hodges (Planta, 199, 612-617, 1996); Chan et al. (Plant Mol. Biol. 22 (3) 491-506, 1993); Hiei et al. (Plant J. 6 (2) 271-282, 1994); which disclosures are incorporated by reference herein as if fully set forth. In the case of corn transformation, the preferred method is as described in either Ishida et al. (Nat. Biotechnol. 1996 June; 14(6): 745-50) or Frame et al. (Plant Physiol. 2002 May; 129(1): 13-22), which disclosures are incorporated by reference herein as if fully set forth.

Generally after transformation, plant cells or cell groupings are selected for the presence of one or more markers which are encoded by plant-expressible genes co-transferred with the gene of interest (which could be under the control of any of the promoters of the present invention), following which the transformed material may be cultivated under conditions promoting plant growth.

The resulting transformed plant cell may then be used to regenerate a transformed plant in a manner known to persons skilled in the art. Accordingly, the method for the production of a transgenic plant as described hereinabove, may further comprise regenerating a plant from said plant cell of (a).

The present invention further provides a plant comprising a plant cell as described hereinabove. The plants may also be able to grow, or even reach maturity including for example fruit production, seed formation, seed ripening and seed setting.

Furthermore, progeny may be produced from these seeds, which progeny may be fertile. Alternatively or additionally, the transformed and regenerated plants may also produce progeny by non-sexual propagation such as cloning, grafting. The generated transformed plants may be propagated by a variety of means, such as by clonal propagation or classical breeding techniques. For example, a first generation (or T1) transformed plant may be selfed to give homozygous second generation (or T2) transformants, and the T2 plants further propagated through classical breeding techniques.

The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

Following DNA transfer and growth of the transformed cells, putatively transformed plant cells or plants may be evaluated, for instance using Southern analysis, for the presence of the gene of interest, copy number and/or genomic organization. Alternatively or additionally, expression levels or expression patterns of the newly introduced DNA may be undertaken using northern and/or Western analysis, both techniques being well known to persons having ordinary skill in the art.

The present invention clearly extends to plants obtainable by any of the methods according to the present invention, which plants comprise any of the isolated promoters or the constructs of the present invention. The present invention clearly extends to any plant parts and propagules of such plant. The present invention extends further to encompass the progeny of a primary transformed cell, tissue, organ or whole plant that has been produced by any of the aforementioned methods, the only requirement being that progeny exhibit the same genotypic and/or phenotypic characteristic(s) as those produced in the parent by the methods according to the invention. The invention also extends to harvestable parts of a plant, such as but not limited to seeds, leaves, fruits, flowers, stem cultures, stem, rhizomes, roots, tubers, bulbs and cotton fibers.

The term “plant” or “plants” as used herein encompasses whole plants, ancestors and progeny of plants and plant parts, including seeds, shoots, stems, roots (including tubers), and plant cells, tissues and organs. The term “plant” therefore also encompasses suspension cultures, embryos, meristematic regions, callus tissue, gametophytes, sporophytes, pollen, and microspores. Plants that are particularly useful in the methods of the invention include all plants which belong to the superfamily Viridiplantae, in particular monocotyledonous and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis, Albizia amara, Alsophila tricolor, Andropogon* spp., *Arachis* spp, *Areca catechu, Astelia fragrans, Astragalus cicer, Baikiaea plurjuga, Betula* spp., *Brassica* spp., *Bruguiera gymnorrhiza, Burkea africana, Butea frondosa, Cadaba farinosa, Calliandra* spp, *Camellia sinensis, Canna indica, Capsicum* spp., *Cassia* spp., *Centroema pubescens, Chaenomeles* spp., *Cinnamomum cassia, Coffea arabica, Colophospermum mopane, Coronillia varia, Cotoneaster serotina, Crataegus* spp., *Cucumis* spp., *Cupressus* spp., *Cyathea dealbata, Cydonia oblonga, Cryptomeria japonica, Cymbopogon* spp., *Cynthea dealbata, Cydonia oblonga, Dalbergia monetaria, Davallia divaricata, Desmodium* spp., *Dicksonia squarosa, Diheteropogon amplectens, Dioclea* spp, *Dolichos* spp., *Dorycnium rectum, Echinochloa pyramidalis, Ehrartia* spp., *Eleusine coracana, Eragrestis* spp., *Erythrina* spp., *Eucalyptus* spp., *Euclea schimperi, Eulalia villosa, Fagopyrum* spp., *Feijoa sellowiana, Fragaria* spp., *Flemingia* spp, *Freycinetia banksii, Geranium thunbergii, Ginkgo biloba, Glycine javanica, Gliricidia* spp, *Gossypium hirsutum, Grevillea* spp., *Guibourtia coleosperma, Hedysarum* spp., *Hemarthia altissima, Heteropogon contortus, Hordeum vulgare, Hyparrhenia rufa, Hypericum erectum, Hyperthelia dissoluta, Indigo incarnata, Iris* spp., *Leptarrhena pyrolifolia, Lespediza* spp., *Lettuca* spp., *Leucaena leucocephala, Loudetia simplex, Lotonus bainesii, Lotus* spp., *Macrotyloma axillare, Malus* spp., *Manihot esculenta, Medicago sativa, Metasequoia glyptostroboides, Musa sapientum, Nicotianum* spp., *Onobrychis* spp., *Ornithopus* spp., *Oryza* spp., *Peltophorum africanum, Pennisetum* spp., *Persea gratissima, Petunia* spp., *Phaseolus* spp., *Phoenix canariensis, Phormium cookianum, Photinia* spp., *Picea glauca, Pinus* spp., *Pisum sativum, Podocarpus totara, Pogonarthria fleckii, Pogonarthria squarrosa, Populus* spp., *Prosopis cineraria, Pseudotsuga menziesii, Pterolobium stellatum, Pyrus communis, Quercus* spp., *Rhaphiolepsis umbellata, Rhopalostylis sapida, Rhus natalensis, Ribes grossularia, Ribes* spp., *Robinia pseudoacacia, Rosa* spp., *Rubus* spp., *Salix* spp., *Schyzachyrium sanguineum, Sciadopitys verticillata, Sequoia sempervirens, Sequoiadendron giganteum, Sorghum bicolor, Spinacia* spp., *Sporobolus fimbriatus, Stiburus alopecuroides, Stylosanthos humilis, Tadehagi* spp, *Taxodium distichum, Themeda triandra, Trifolium* spp., *Triticum* spp., *Tsuga heterophylla, Vac-*

*cinium* spp., *Vicia* spp. *Vitis vinifera, Watsonia pyramidata, Zantedeschia aethiopica, Zea mays*, amaranth, artichoke, asparagus, broccoli, brussel sprout, cabbage, canola, carrot, cauliflower, celery, collard greens, flax, kale, lentil, oilseed rape, okra, onion, potato, rice, soybean, straw, sugarbeet, sugar cane, sunflower, tomato, squash, and tea, trees and algae amongst others. According to a preferred feature of the present invention, the plant is a crop plant such as soybean, sunflower, canola, alfalfa, rapeseed, cotton, tomato, potato, tobacco, squash, papaya, poplar, leguminosa, flax, lupinus or sorghum. According to another preferred embodiment of the present invention the plant is a monocotyledonous plant, such as sugarcane, further preferable a cereal such as rice, maize, wheat, barley, millet, rye or oats.

The invention further provides a method for driving and/or regulating expression of a nucleic acid in a plant or plant cell, comprising:

a) Operably linking a nucleic acid to an isolated nucleic acid according to the invention as described hereinabove, such as to any one of SEQ ID NO 1 to 22 or a variant or fragment thereof, and
b) Introducing the resultant genetic construct into a plant or plant cell.

Preferably the operably linked nucleic acid of (a) is heterologous to the nucleic acids according to the present invention.

This method may further comprise cultivating the transformed plant or plant cell under conditions promoting growth, promoting regeneration and/or promoting maturation.

Furthermore, the expression of the operably linked nucleic acid may be driven and/or regulated in particular cells, tissues or organs of a plant. Accordingly, the invention provides a method as described above, wherein the expression is constitutive expression or tissue-specific expression. For these embodiments, reference is made to the example section where the specific expression patterns of the promoters according to the invention are described and where different types of tissue-specific expression are detailed.

The present invention further encompasses the use of an isolated nucleic acid as defined hereinabove to drive and/or regulate expression of an operably linked nucleic acid.

(i) The person skilled in the art will recognize that provision of sequences SEQ ID NO 1 to 22, readily makes available the tools to isolate related promoters, which may have substantial sequence identity to any of SEQ ID NO 1 to 22. Additionally, provision of sequences SEQ ID NO 23 to 44 (CDS corresponding to the promoters of the present invention, see Table 1), readily makes available the tools to isolate related promoters, of which the related CDSs may have substantial sequence identity to any of SEQ ID NO 23 to 44. Therefore the present invention also encompasses a method for isolating nucleic acids, capable of driving and/or regulating expression of an operably linked nucleic acid, comprising screening a nucleic acid sequence database to find homologues of any of the sequences represented by SEQ ID NO 1 to 22 or SEQ ID NO 23 to 44. Subsequently these homologues are used to screen a library with genomic DNA, which library is for example prepared from the organism of origin of the above mentioned homologue. The screening procedure may for example involve hybridization. Subsequently, the genomic DNA that matches the homologue, is analysed to identify the transcription initiation site and the translation initiation site of the gene corresponding to the homologue. Finally, specific primers are designed for amplification of a nucleic acid located in the region upstream (at the 5' end) of said translation initiation site.

The present invention extends to the identification of regulatory proteins that are involved in the regulation of the activity of the promoters according to the present invention. Such identification may be achieved using a yeast one-hybrid system. In such a yeast one-hybrid system the sequences according to any one of SEQ ID NO 1 to 22 are operably linked to the GAL transcription activator and transformed to a yeast cell culture. That yeast cell culture is again transformed with a library of constructs encoding candidate regulatory factors.

The present invention will now be described with reference to the following figures in which:

FIG. 1 shows a general schematic representation of a promoter. Regulatory elements are sequences that may for example be responsible for special and/or temporal regulation of the promoter activity. The minimal promoter is the minimal sequence necessary and sufficient to drive expression. It includes a TATA box, which is necessary to correctly direct the RNA polymerase II to the transcription initiation site. The transcription initiation element (INR) includes the transcription initiation start site. The 5' untranslated region (5'UTR) is the region that is transcribed into pre-messenger RNA and eventually into mRNA, but is not translated into protein. The translation initiation codon is represented by the startcodon ATG.

FIG. 2 is a map of the vector p4581 useful for expression in plants of a β-glucuronidase (GUS) gene under control of any one of the promoters according to the invention. This binary vector comprises a Gateway recombination cassette, suitable for the recombination cloning of any of the promoters of the present invention in front of the *Escherichia coli*β-glucuronidase (GUS) gene. This cassette contains a chloramphenicol resistance gene (CamR) and the ccdB suicide gene for counter selection of non-recombined plasmids, This GUS expression cassette further comprises the double terminator sequence T-zein and T-rbcS-deltaGA. This expression cassette is located within the left border (LB repeat, LB Ti C58) and the right border (RB repeat, RB Ti C58) of the nopaline Ti plasmid. Cloned within these borders are also selectable marker and a screenable marker genes each under control of a constitutive promoter and a terminator sequence. This vector also contains an origin of replication (pBR322) for bacterial replication and a bacterial selectable marker (Spe/SmeR) for bacterial selection.

The following figures show the results of the GUS staining of plants or plant parts transformed with the reporter vector p4581 carrying a promoter according to the present invention operably linked to the reporter gene GUS. Plants denoted "C plants" are transgenic plants grown to about 5 cm; Plants denoted "B plants" are grown to about 10 cm; and plants denoted "A plants" are grown to maturity. These A plants were used to collect different tissue samples from old leaves, young leaves and seeds.

FIG. 4 shows the expression pattern of PRO0005 (putative beta-amylase, SEQ ID NO 2). GUS staining is visible in seeds, more specifically in the embryo or in the scutellum of the embryo.

FIG. 5 shows the expression pattern of PRO0009 (putative cellulose synthetase, SEQ ID NO 3). GUS staining is visible in roots.

FIG. 6 shows the expression pattern of PRO0058 (proteinase inhibitor Rgpi9, SEQ ID NO 4). GUS staining is visible in the seeds.

EXAMPLES

Figure 1:
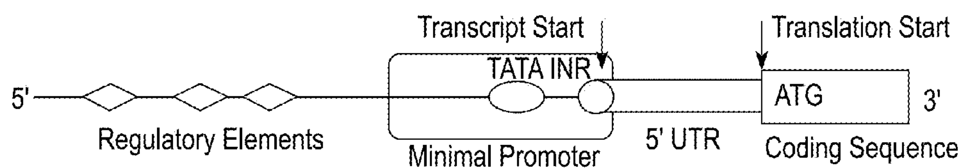

The promoters according to the present invention were isolated as DNA regions spanning about 1.2 kb of the sequence upstream of the translation initiation codon (i.e. first ATG, which codon was excluded) from various rice genes. For determination of their nucleic acid sequence and their expression pattern, the following procedure was followed: First in silico studies on genomic rice sequences were performed. However, procedures based on automated prediction programs to locate promoter-like nucleic acid sequence are highly error prone, even for the localization the best-characterized promoter control elements such as the TATA box and the transcription initiation element (INR). Also, in silico determination of expression pattern is extremely speculative. Therefore, to obtain unambiguous data about the nucleic acid sequence and the expression pattern of the promoters, in vivo studies were performed encompassing (i) isolation of the promoter nucleic acid sequence; (ii) operably linking a reporter gene to the promoter and introducing the resulting genetic construct into a host organisms; (iii) growing the transformed host cell under conditions allowing expression of the reporter gene, and (iv) determination of the reporter gene activity in the different tissues of the host organism. These methods are now described in more detail.

Example 1

Identification and Isolation of the Promoters

Identification of Rice ESTs, the Corresponding Genes and their Location in the Rice Genome Sequence databases, comprising rice sequences, were searched for rice expressed sequence tags (ESTs). Subsequently an "in silico" Northern-blot was performed to allow identification of EST families that are strongly expressed or that are specific for a particular organ. This analysis included normalization of the numbers of ESTs isolated from different plant organs. The ESTs families with an interesting distribution among source cDNA libraries were selected for further analysis and sequence homology searches. After sequence homology searches in combination with scanning scientific data, the genes that correspond to those families of ESTs were identified from sequence databases and a (putative) function and corresponding gene name was given (see Table 1). Subsequently, the corresponding promoter region was isolated by the following procedure. In a first step the TIGR database was searched to find a tentative contig corresponding to an EST family. Sequence homology was found using standard computer programs, such as Blast N using standard parameters (typically G Cost to open a gap=5, E Cost to extend a gap=2, q Penalty for a mismatch in the blast portion of run=−3, r Reward for a match in the blast portion of run=1, e Expectation value=10.0, W Word size=11, v Number of one-line descriptions=100, b Number of alignments to show=100, Matrix=BLOSUM62). The TIGR database (The Institute for Genomic Research), provides Tentative Contigs (TC) which are sequence predictions based on contig building from all known EST, from all known cDNA and from reconstructed mRNA. The TCs used for identification of the promoters of the present invention are represented in Table 1. In a second step these TCs were used to locate the corresponding gene on a genomic sequence, which gene comprises the coding region as well as the promoter region. Generally, these genomic sequences were BAC clones, which are represented herein by their Genbank accession number (see Table 1). From these BAC clones the sequence identity of the promoter region could be determined.

TABLE 1 list of rice promoters of the present invention. The promoter sequences are represented herein by their SEQ ID NO and promoter number (PRO). The coding sequences (CDS) naturally driven by a promoter of the present invention are represented by their name, by SEQ ID NO and by Tentative contig (TC) accession number of the TIGR database. The Genomic sequences (BAC clones or genes) comprising a promoter region of the present invention are represented by their Genbank accession number.

| Prom SEQ ID NO | Prom number | CDS name | CDS SEQ ID NO | CDS TC | BAC clone (*or gene) |
|---|---|---|---|---|---|
| 1 | PRO0110 | RCc3 | 23 | TC89946 | AC037426 |
| 2 | PRO0005 | putative beta-amylase | 24 | TC90358 | AC022457 |
| 3 | PRO0009 | putative cellulose synthase | 25 | TC83635 | AC022457 |
| 4 | PRO0058 | proteinase inhibitor Rgpi9 | 26 | TC83117 | AF044059 |
| 5 | PRO0061 | beta expansine EXPB9 | 27 | TC89913 | AC020666 |
| 6 | PRO0063 | structural protein | 28 | TC89985 | AP001278 |
| 7 | PRO0081 | putative caffeoyl-CoA 3-O-methyltransferase | 29 | TC89891 | AP000364 |
| 8 | PRO0091 | prolamine RP5 | 30 | TC89670 | AF156714* |
| 9 | PRO0095 | putative methionine aminopeptidase | 31 | TC89883 | AC027133 |
| 10 | PRO0111 | uclacyanin 3-like protein | 32 | TC90434 | AJ307662 |
| 11 | PRO0116 | 26S proteasome regulatory particle non-ATPase subunit 11 | 33 | TC83072 | AP000969 |
| 12 | PRO0117 | putative 40S ribosomal protein | 34 | TC90038 | AC090871 |
| 13 | PRO0122 | chlorophyll a/b-binding protein presursor (Cab27) | 35 | TC82936 | AP004700 |
| 14 | PRO0123 | putative protochlorophyllide reductase | 36 | TC89839 | AL606456 |
| 15 | PRO0133 | chitinase Cht-3 | 37 | TC85888 | D16223* |
| 16 | PRO0151 | WSI18 | 38 | TC84300 | AP003023 |
| 17 | PRO0169 | aquaporine | 39 | TC89687 | AP005108 |
| 18 | PRO0170 | High mobility group protein | 40 | TC89846 | AP004004 |
| 19 | PRO0171 | reversibly glycosylated protein RGP1 | 41 | TC82935 | AC090874 |
| 20 | PRO0173 | cytosolic MDH | 42 | TC82977 | AC037425 |
| 21 | PRO0175 | RAB21 | 43 | TC83646 | Y00842* |
| 22 | PRO0177 | Cdc2-1 | 44 | TC90619 | AP004765 |

Identification and Isolation of the Promoter Regions of Rice Genes

Starting from the sequence information of the genes and their location in the rice genome, the promoter regions of these genes were isolated as the DNA region spanning about 1.2 kb upstream of the translation initiation codon (i.e. first ATG), which codon was excluded. When an intervening sequence such as an intron, was present in the 5' untranslated region of the gene, the isolated DNA region was taken as the region spanning about 1.2 kb plus the length of that intervening sequence. The promoter regions were isolated from genomic DNA of *Oryza sativa Japonica* or exceptionally from *Oryza sativa Indica* via PCR using specific primers. These specific primers comprise AttB recombination sites, suitable for recombination cloning of the isolated promoter region These specific primers are herein represented as SEQ ID NO 45 to 88 and are listed in Table 2. Conditions for PCR were as follows: 1 cycle of 2 min at 94° C., 35 cycles of 1 min at 94° C., 1 min at 58° C. and 2 min at 68° C., and 1 cycle of 5 min at 68° C. The length of the expected PCR fragment is also indicated in Table 2. The corresponding PCR fragment was purified from the PCR reaction mix via gele electrophoresis and subsequent purification using Zymoclean Gel DNA Recovery Kit (Zymo Research, Orange, Calif.).

TABLE 2

Overview of the primers used to isolate the rice promoters of the present invention and the length of the rice promoter regions.

| Promoter SEQ ID NO | Promoter number | Prom length | Primer forward SEQ ID NO | Primer forward | Primer reverse SEQ ID NO | Primer reverse |
|---|---|---|---|---|---|---|
| 1 | PRO0110 | 1264 | 45 | prm3780 | 67 | prm3781 |
| 2 | PRO0005 | 1215 | 46 | prm2768 | 68 | prm2769 |
| 3 | PRO0009 | 1038 | 47 | prm2420 | 69 | prm2421 |
| 4 | PRO0058 | 1301 | 48 | prm2853 | 70 | prm2854 |
| 5 | PRO0061 | 1243 | 49 | prm2426 | 71 | prm2427 |
| 6 | PRO0063 | 1019 | 50 | prm2855 | 72 | prm2856 |
| 7 | PRO0081 | 1212 | 51 | prm3025 | 73 | prm3026 |
| 8 | PRO0091 | 1052 | 52 | prm3029 | 74 | prm3030 |
| 9 | PRO0095 | 1216 | 53 | prm3061 | 75 | prm3062 |
| 10 | PRO0111 | 1237 | 54 | prm3031 | 76 | prm3032 |
| 11 | PRO0116 | 1100 | 55 | prm3051 | 77 | prm3052 |
| 12 | PRO0117 | 1216 | 56 | prm3592 | 78 | prm3049 |
| 13 | PRO0122 | 1210 | 57 | prm5131 | 79 | prm2195 |
| 14 | PRO0123 | 123 | 58 | prm3782 | 80 | prm2197 |
| 15 | PRO0133 | 1808 | 59 | prm2844 | 81 | prm2845 |
| 16 | PRO0151 | 1828 | 60 | prm2973 | 82 | prm2974 |
| 17 | PRO0169 | 1267 | 61 | prm3770 | 83 | prm3771 |
| 18 | PRO0170 | 1130 | 62 | prm3772 | 84 | prm3773 |

TABLE 2-continued

Overview of the primers used to isolate the rice promoters of the present invention and the length of the rice promoter regions.

| Promoter SEQ ID NO | Promoter number | Prom length | Primer forward SEQ ID NO | Primer forward | Primer reverse SEQ ID NO | Primer reverse |
|---|---|---|---|---|---|---|
| 19 | PRO0171 | 1230 | 63 | prm3774 | 85 | prm3775 |
| 20 | PRO0173 | 1234 | 64 | prm3776 | 86 | prm3777 |
| 21 | PRO0175 | 1553 | 65 | prm3800 | 87 | prm3801 |
| 22 | PRO0177 | 1087 | 66 | prm5135 | 88 | prm5136 |

Example 2

Cloning of Promoter-GUS Reporter Vectors for Plant Transformation

The purified PCR fragments of Example 1, corresponding to the promoter regions of the present invention, were cloned into the pDONR201 entry plasmid of the Gateway™ system (Life Technologies) using the "BP recombination reaction". The identity and base pair composition of the cloned insert was confirmed by sequencing and additionally, the resulting plasmid was tested via restriction digests.

Figure 2:
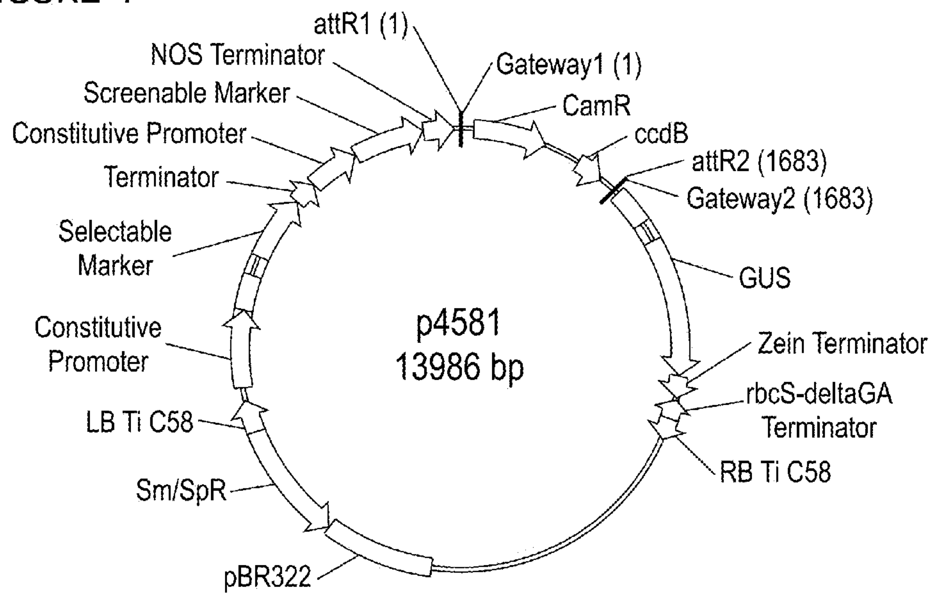
Figure 3:
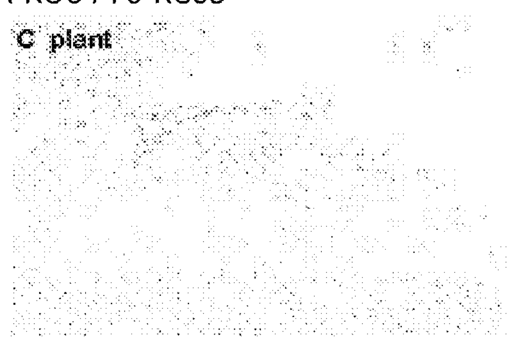
FIG. 3 shows the expression pattern of PRO0110 (RCc3, SEQ ID NO 1). GUS staining is visible in roots.
Figure 7:
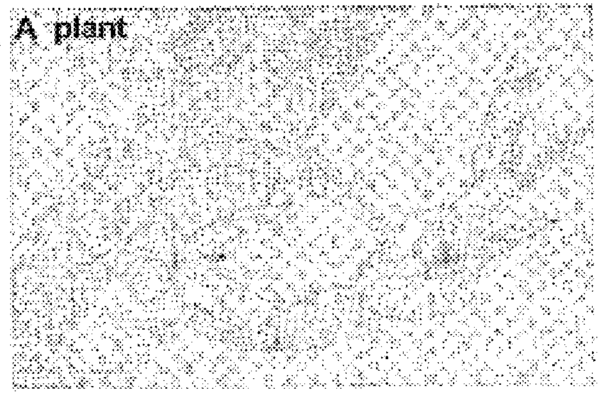
FIG. 7 shows the expression pattern of PRO0061 (beta expansine EXPB9, SEQ ID NO 5). GUS staining is visible in young flowers of A plants (A) and in other young expanding tissues of B plants (B) and C plants (C).
Figure 7:
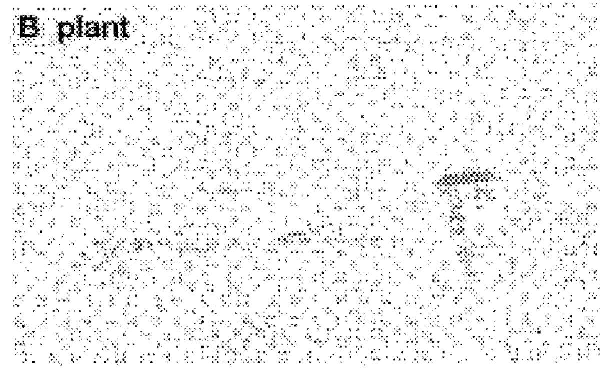
Figure 7:
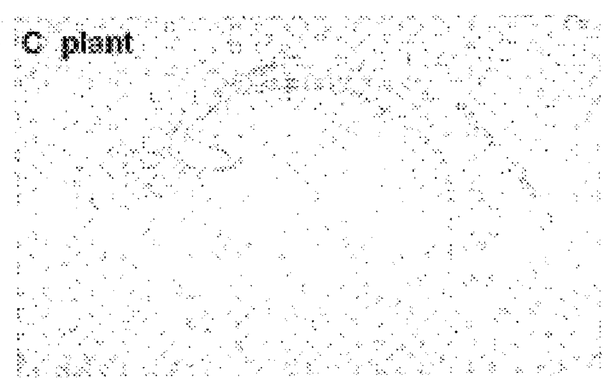
Figure 8:
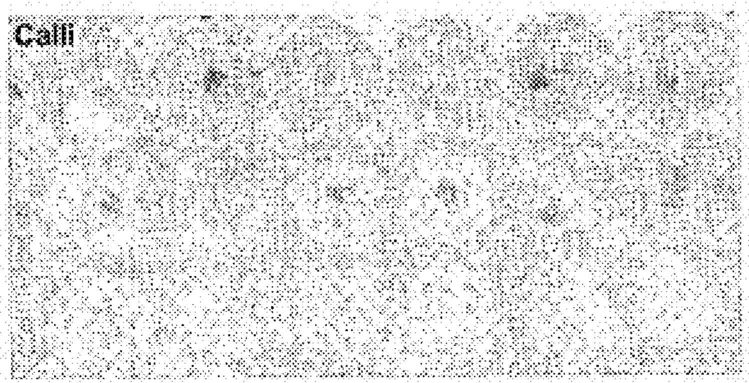
FIG. 8 shows the expression pattern of PRO0063 (putative structural protein, SEQ ID NO 6). GUS staining is visible in young tissues, for example in the calli (A) or old leaves, young leaves and seeds of "A plants" (B).
Figure 9:
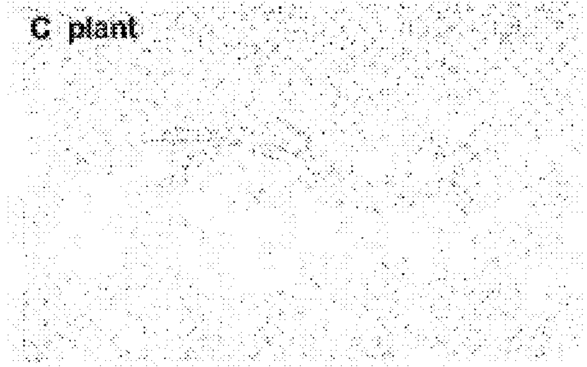
FIG. 9 shows the expression pattern of PRO0081 (putative caffeoyl-CoA 3-O-methyltransferase, SEQ ID NO 7). GUS staining is visible in young tissues, particularly of the shoot.
Figure 10:
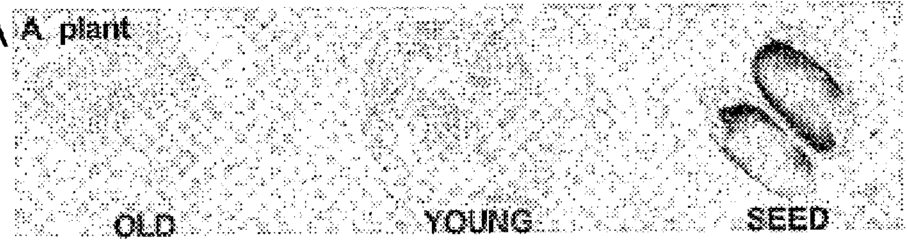
FIG. 10 shows the expression pattern of PRO0091 (prolamine RP5, SEQ ID NO 8). GUS staining is visible in seeds (A), particularly in the endosperm, and in meristem (B).
Figure 11:
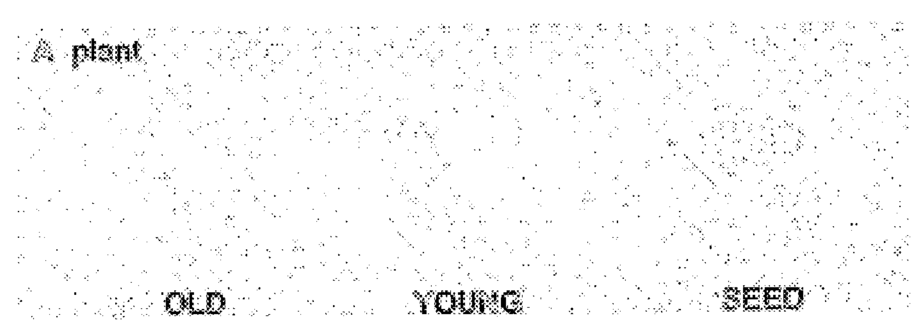
FIG. 11 shows the expression pattern of PRO0095 (putative amino peptidase, SEQ ID NO 9). GUS staining is visible in seeds, more particularly in the embryo.
Figure 12:
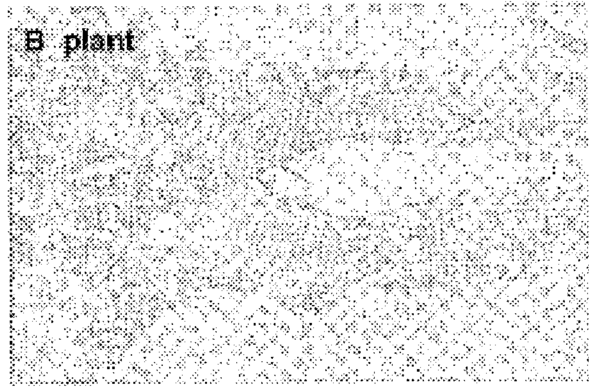
FIG. 12 shows the expression pattern of PRO0111 (uclacyanin 3-like protein, SEQ ID NO 10). GUS staining is visible in roots and in meristem.
Figure 13:
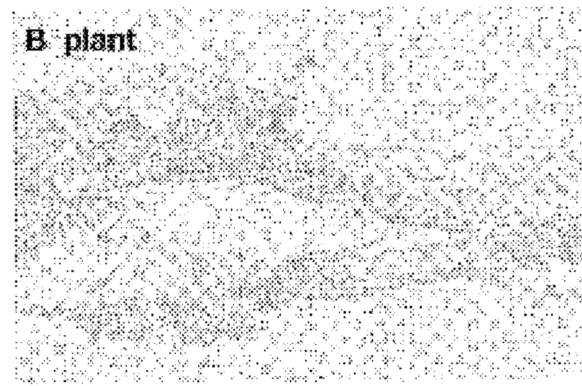
FIG. 13 shows the expression pattern of PRO0116 (26S proteasome regulatory particle non-ATPase subunit 11, SEQ ID NO 11). GUS staining is weakly visible in the whole plant (weak constitutive) and is particularly visible in meristem.
Figure 14:
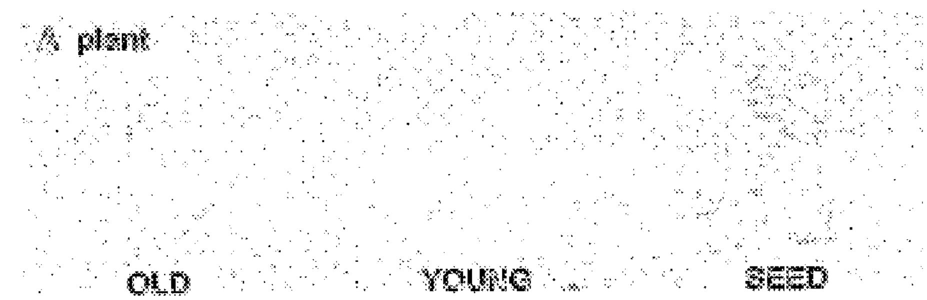
FIG. 14 shows the expression pattern of PRO0117 (putative 40S ribosomal protein, SEQ ID NO 12). GUS staining is visible in the seeds, more particularly in the endosperm.
Figure 15:
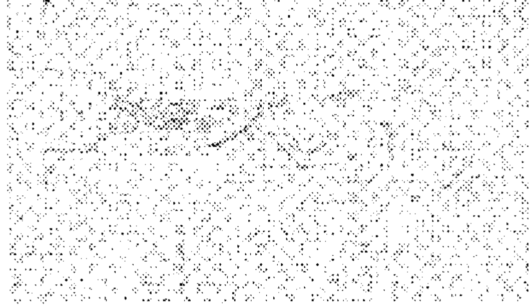
FIG. 15 shows the expression pattern of PRO0122 (chlorophyll a/b-binding protein presursor (Cab27), SEQ ID NO 13). GUS staining is visible in the shoot.
Figure 16:
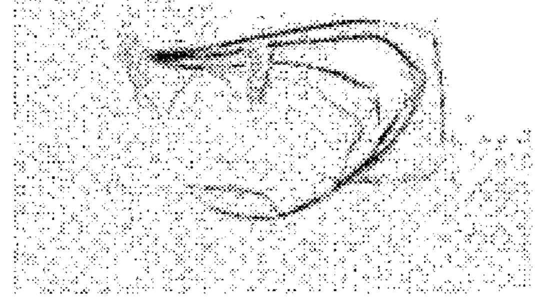
FIG. 16 shows the expression pattern of PRO0123 (putative protochlorophyllide reductase, SEQ ID NO 14). GUS staining is visible in the shoot (above-ground tissues).
Figure 17:
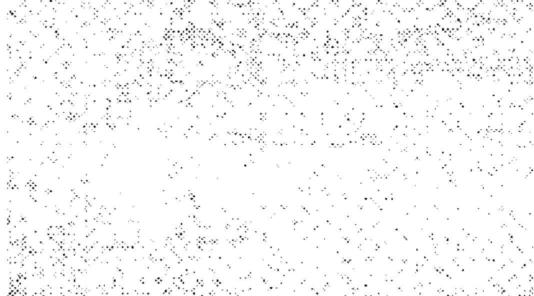
FIG. 17 shows the expression pattern of PRO0133 (chitinase Cht-3, SEQ ID NO 15). GUS staining is visible in the roots and meristem.
Figure 18:
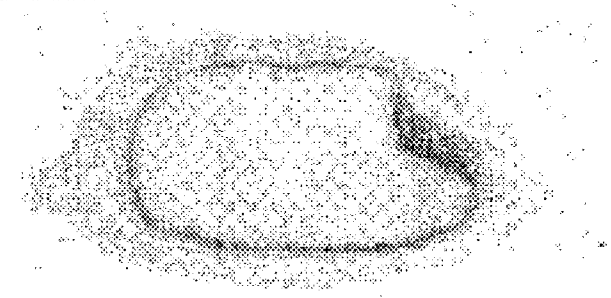
FIG. 18 shows the expression pattern of PRO0151 (WSI18, SEQ ID NO 16). GUS staining is visible in the calli and upper plant parts (A) as well as in the aleurone layer and embryo (B).
Figure 19:
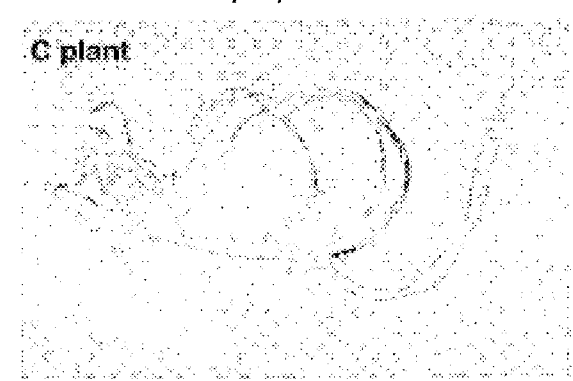
FIG. 19 shows the expression pattern of PRO0169 (aquaporine, SEQ ID NO 17). GUS staining is visible in the whole plant (constitutive expression).
Figure 20:
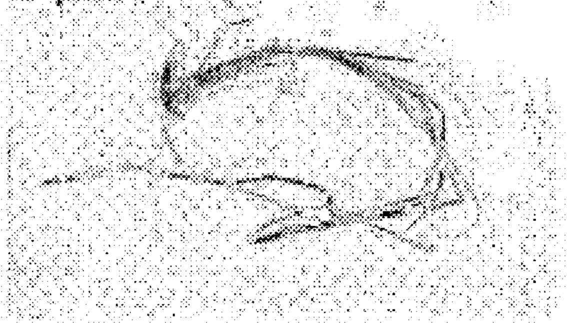
FIG. 20 shows the expression pattern of PRO0170 (High mobility group protein, SEQ ID NO 18). GUS staining is strongly visible in the whole plant as is illustrated by the "B plants" (A), and various tissues such as old leaves, young leaves and seeds (B) and calli (C) (constitutive expression).
Figure 20:
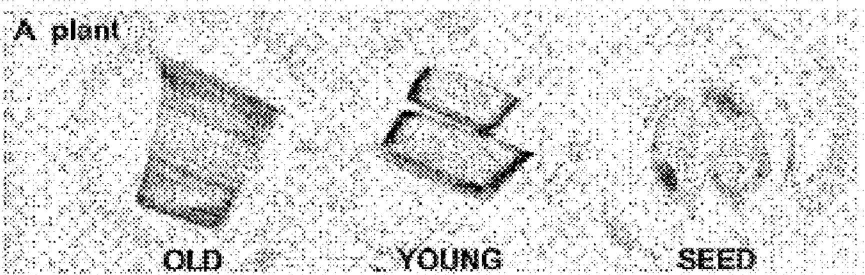
Figure 20:
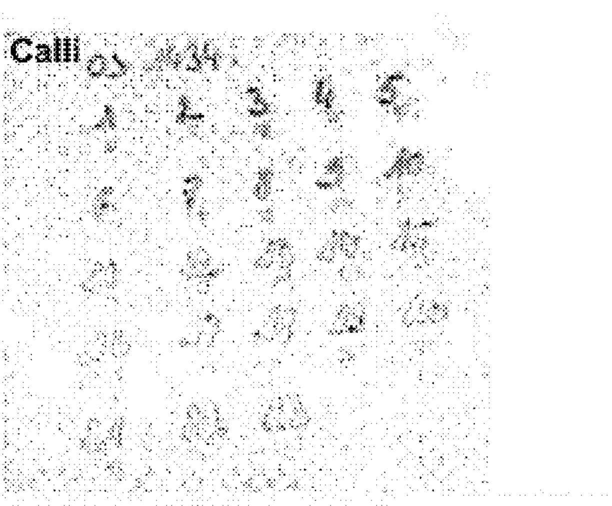
Figure 21:
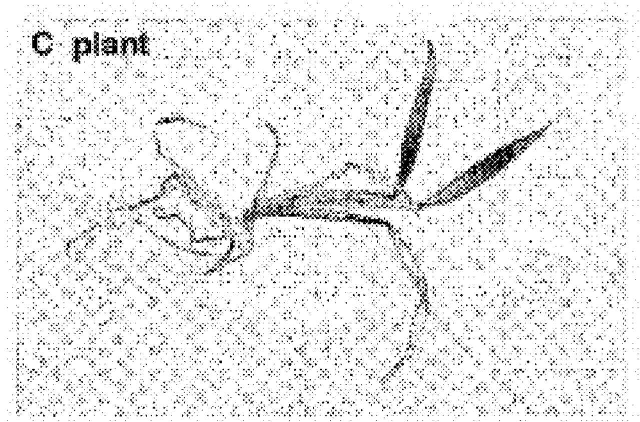
FIG. 21 shows the expression pattern of PRO0171 (reversibly glycosylated protein RGP1, SEQ ID NO 19). GUS staining is visible in all plant parts (constitutive expression).
Figure 22:
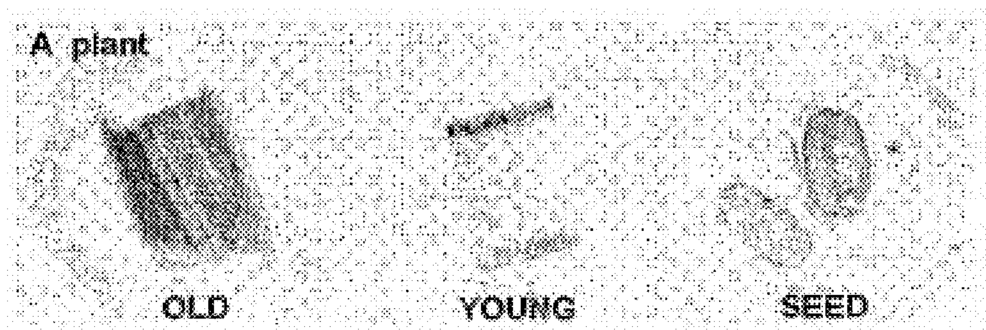
FIG. 22 shows the expression pattern of PRO0173 (cytosolic MDH, SEQ ID NO 20). GUS staining is visible in all plant parts and particularly in the shoot (above-ground tissues) and seeds.
Figure 23:
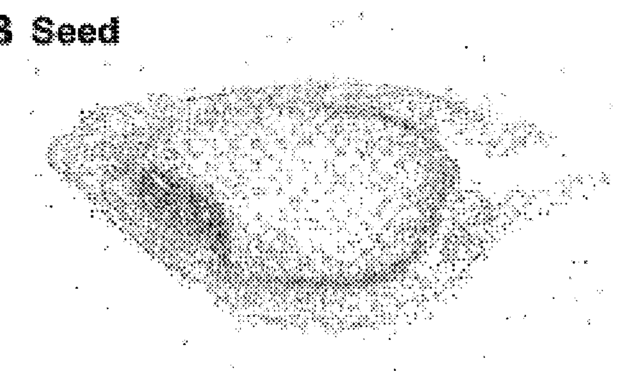
FIG. 23 shows the expression pattern of PRO0175 (RAB21, SEQ ID NO 21). GUS staining is weakly visible in calli (A), meristems and young leaves, and is strongly visible in developing and maturing seeds (B) more particularly in the embryo.
Figure 24:
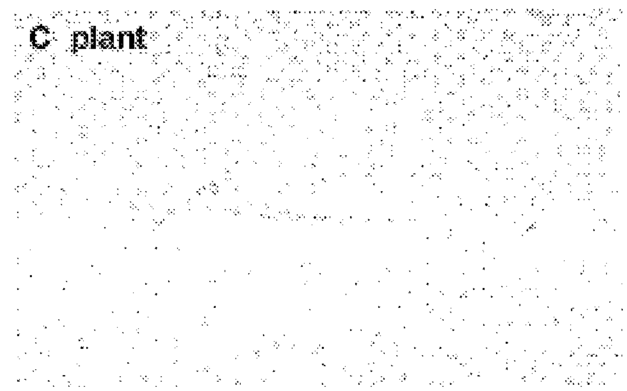
FIG. 24 shows the expression pattern of PRO0177 (Cdc2-1, SEQ ID NO 22). GUS staining is weakly visible in meristem and in leaf sheets.

In order to clone each of the promoters of the present invention in front of a reporter gene, each entry clone of Example 1 was subsequently used in an "LR recombination reaction" (Gateway™) with the destination vector p4581. This destination vector was designed to operably link each promoter of the present invention to the *Escherichia coli* beta-glucuronidase (GUS) gene via the substitution of the Gateway recombination cassette in front of the GUS gene. Furthermore this destination vector is suitable for transformation of plants and comprises within the T-DNA left and right borders the resulting promoter-GUS cassette and selectable marker and screenable marker cassettes (see FIG. 2). The resulting reporter vectors, comprising a promoter of the present invention operably linked to GUS, are subsequently transformed into *Agrobacterium* strain LBA4044 and subsequently into rice plants using standard transformation techniques.

Example 3

Expression Patterns of the Promoter-GUS Reporter Cassette in Plants

Growth and Harvest of Transgenic Plants or Plant Parts at Various Stages (C Plants, B Plants and a Plants)

For each promoter-GUS reporter construct, 3 T0 transgenic rice plants were generated from transformed cells. Plant growth was performed under normal conditions. The first transgenic plant was sacrificed for GUS staining when it had reached a size of about 5 cm, which plant is named herein "C plant". The second transgenic plant was sacrificed for GUS staining when it had reached a size of about 10 cm, which plant is named herein "B plant". The third transgenic plant was kept for seed production and is named herein "A plant". GUS staining was performed on complete C and B plants. On A plants, GUS staining was performed on leaf pieces, flowers and section of seeds at various developmental stages. A plants were allowed to set seed, which seeds were used after harvest for confirmation of the expression pattern in T1 plants.

GUS Staining

The sacrificed plants or plant parts were covered with 90% ice-cold acetone and incubated for 30 min at 4° C. After 3 washes of 5 min with Tris buffer [15.76 g Trizma HCl (Sigma T3253)+2.922 g NaCl in 1 l bidi, adjusted to pH 7.0 with NaOH], the material was covered by a Tris/ferricyanate/X-Gluc solution [9.8 ml Tris buffer+0.2 ml ferricyanate stock (0.33 g Potassium ferricyanate (Sigma P3667) in 10 ml Tris buffer)+0.2 ml X-Gluc stock (26.1 mg X-Gluc (Europa Bioproducts ML 113A) in 500 μl DMSO)]. Vacuum infiltration was applied for 15 to 30 minutes. The plants or plant parts were incubated for up to 16 hours at 37° C. until development of blue colour was visible. The samples were washed 3 times for 5 minutes with Tris buffer. Chlorophyll was extracted in ethanol series of 50%, 70% and 90% (each for 30 minutes).

Expression Patterns of the Promoters of the Present Invention

The expression patterns of the rice promoters of the present invention are summarized in Table 3.

TABLE 3 expression patterns of the rice promoters of the present invention

| PRO SEQ ID NO | Promoter number | Promoter name | Expression pattern |
|---|---|---|---|
| 1 | PRO0110 | RCc3 | strong root |
| 2 | PRO0005 | putative beta-amylase | Embryo (scutellum) |
| 3 | PRO0009 | putative cellulose synthase | weak in roots |
| 4 | PRO0058 | proteinase inhibitor Rgpi9 | seed |
| 5 | PRO0061 | beta expansine EXPB9 | weak in young tissues |
| 6 | PRO0063 | structural protein | young tissues + calli + embryo |
| 7 | PRO0081 | putative caffeoyl-CoA 3-O-methyltransferase | shoot |
| 8 | PRO0091 | prolamine RP5 | meristem + strong in endosperm |
| 9 | PRO0095 | putative methionine aminopeptidase | embryo |
| 10 | PRO0111 | uclacyanin 3-like protein | weak meristem |
| 11 | PRO0116 | 26S proteasome reg. particle non-ATPase s.u. 11 | weak meristem |
| 12 | PRO0117 | putative 40S ribosomal protein | weak in endosperm |

TABLE 3-continued expression patterns of the rice promoters of the present invention

| PRO SEQ ID NO | Promoter number | Promoter name | Expression pattern |
|---|---|---|---|
| 13 | PRO0122 | chlorophyll a/b-binding protein presursor (Cab27) | weak in shoot |
| 14 | PRO0123 | putative protochlorophyllide reductase | strong shoot specific |
| 15 | PRO0133 | chitinase Cht-3 | weak meristem specific |
| 16 | PRO0151 | WSI18 | Calli + shoot + strong embryo |
| 17 | PRO0169 | aquaporine | medium constitutive |
| 18 | PRO0170 | High mobility group protein | strong constitutive |
| 19 | PRO0171 | reversibly glycosylated protein RGP1 | weak constitutive |
| 20 | PRO0173 | cytosolic MDH | Shoot and seed |
| 21 | PRO0175 | RAB21 | embryo |
| 22 | PRO0177 | Cdc2-1 | weak in meristem + strong seed |

The following paragraphs describe the observed expression patterns of the promoters of the present invention in more detail. The observations are based on the visual inspection of the GUS stained tissues as described above. It is to be understood that for some promoters expression may be weak and that expression in certain tissues may only be visible with very sensitive detection methods.

PRO0110—SEQ ID NO 1—RCc3

1 construct (OS1432), which is a reporter vector as described in Example 2 comprising PRO0110 was investigated. 25 calli, 14 C, 21 B plants and 21 A plants were analysed. There was no expression visible in calli, but strong expression in roots of C plants (93%) and of B plants (81%) was observed. No expression in the shoots of A plants was observed. Therefore the RCc3 promoter PRO0110 is suitable for strong expression in roots.

PRO0005—SEQ ID NO 2—Putative Beta-Amylase 1 construct (OS1365) was investigated. 28 calli, 24 B plants and 22 A plants were analysed. Occasional expression in calli (7%) was observed as well as occasional weak expression in roots (4%) and shoots (12%) of B plants, expression in the scutellum of embryos of A plants (43%) and occasional expression in leaves (5%) of A plants. This promoter is therefore suitable for expression in embryo, more preferably in the scutellum of the embryo. This region of the embryo is also referred to as the transfer layer of the embryo. This promoter may have some leakiness in other tissues.

PRO0009—SEQ ID NO 3—Putative Cellulose Synthase 1 construct (OS1461) was investigated. 20 calli, 20 C, 20 B plants and 20 A plants were analysed. Occasional expression in calli (20%) was observed as well as weak expression in roots (55%) of C plants, occasional expression in young leaves (10%) of C plants and weak expression in the roots (25%) of B plants. No expression in leaves of A or B plants was observed. Therefore this promoter is suitable for expression in roots. This promoter may show some leakiness in the leaves.

PRO0058—SEQ ID NO 4—Proteinase Inhibitor Rgpi9

1 construct (OS1370) was investigated. 13 B plants and 12 A plants were analysed. No expression was observed in B plants. In A plants, no expression was observed in the leaves, but there was strong expression in endosperm and embryo (58-42%). Therefore, this promoter PRO0058 is suitable for expression in seeds.

PRO0061—SEQ ID NO 5—Beta Expansine EXPB9

2 constructs (OS1441 and OS1460) were investigated. 20 calli, 32 C, 32 B plants and 32 A plants were analysed. Weak expression was observed in the leaves of C and B plants. In A plants expression in the flowers was observed (44%), more particularly in lemma of young spikelets. It was concluded that the promoter PRO0061 is suitable for expression in young tissue, more preferably in young, developing or expanding tissue, more preferably in green tissue.

PRO0063—SEQ ID NO 6—Putative Structural Protein 1 construct (OS1446) was investigated. 13 calli, 13 C, 13 B plants and 12 A plants were analysed. In calli, weak expression was detected (92%). In C plants, there was no expression in roots and there was weak expression in some leaves (46%). In B plants, there was no expression in roots and weak expression in young tillers (78%) or young leaves (54%), but no expression in old leaves. In A plants, there was occasional expression in young leaves (17%) and expression in embryo and scutellum (42%). Therefore it was concluded that this promoter is active in the above-ground tissues, such as leaf, stem and seed. These data demonstrate that the promoter is suitable for expression in calli and in the shoot, and for expression in young tissues and seeds.

PRO0081—SEQ ID NO 7—Putative Caffeoyl-CoA 3-O-Methyltransferase 1 construct (OS1419) was investigated. 20 calli, 20 C, 20 B plants and 20 A plants were analysed. No expression was observed in Calli. Expression was observed in C plants, more particularly weak expression in root cylinder (40%) and weak expression in young leaves (80%) and in old leaves. Expression was also observed in B plants, more particularly weak expression in roots (25%) and weak expression in young leaves (80%). Expression was also observed in young leaves (50%) of A plants. It was concluded that promoter PRO0081 is suitable for expression in above-ground tissues, preferably in the shoot. This promoter may have some leakage of expression in roots.

PRO0091—SEQ ID NO 8—Prolamine RP5

1 construct (OS1558) was investigated. 12 C, 12 B plants and 12 A plants were analysed. Weak expression was observed in the discrimination centre (50%) of C plants and in the discrimination centre (58%) of B plants. Strong expression was observed in endosperm (55%) of A plants. This promoter was found to be useful for strong expression in the endosperm, with leakiness in meristem, preferably the shoot meristem or discrimination centre.

PRO0095—SEQ ID NO 9—Putative Methionine Aminopeptidase 1 construct (OS1423) was investigated. 16 calli, 14 C, 14 B plants and 16 A plants were analysed. Some expression was observed in root-tips (36%) of C plants and in the embryo (38%) of A plants, but not in endosperm of A plants. It was concluded that PRO0095 is suitable for expression in embryo.

PRO0111—SEQ ID NO 10—Uclacyanin 3-Like Protein 1 construct (OS1421) was investigated. 22 calli, 21 C, 22 B plants and 21 A plants were analysed. Weak expression was observed in the discrimination centre and meristems (77%) of B plants. It was concluded that promoter PRO0111 is suitable for weak expression in the meristem, preferably in shoot meristem or discrimination centre.

PRO0116—SEQ ID NO 11—26S Proteasome Regulatory Particle Non-ATPase Subunit 11

1 construct (OS1679) was investigated. 13 C, 14 B plants and A plants were analysed. Weak expression was observed in meristem/discrimination centre of C plants (38%) and of B plants (71%) and in young leaf sheaths of C plants (77%) and of B plants (21%). It was concluded that promoter PRO0116 is suitable for expression in meristem, preferably in shoot meristem or discrimination centre.

PRO0117—SEQ ID NO 12—Putative 40S Ribosomal Protein 1 construct (OS1425) was investigated. 9 calli, 9 C, 9 B plants and 9 A plants were analysed. Occasional weak expression was observed in roots (22%) and in young leaf blades (44%) of C plants. Expression was mainly observed in endosperm (37%) of A plants. Therefore, promoter PRO117 was found to be suitable for expression in endosperm and may have some leakiness in young leaves.

PRO0122—SEQ ID NO 13—Chlorophyll a/b-Binding Protein Presursor (Cab27)

1 construct (OS1675) was investigated. 38 calli, 38 C, 38 B plants and 15 A plants were analysed. Very weak expression was observed in the discrimination centre and young leaf sheaths of C plants. It was concluded that this promoter PRO0122 is suitable for weak expression in shoots.

PRO0123—SEQ ID NO 14—Putative Protochlorophyllide Reductase 1 construct (OS1433) was investigated. 21 calli, 18 C, 19 B plants and 18 A plants were analysed. Strong expression was observed in shoots (33-68%) of C plants and B plants (63-79%). In B plants there was also occasional expression in roots. In A plants, again strong expression in young leaves (73%) was observed, as well as occasional expression in old leaves (39%). It was concluded that this promoter is suitable for strong expression in shoots, preferably in leaves.

PRO0133—SEQ ID NO 15—Chitinase Cht-3

1 construct (OS1687) was investigated. 15 calli, 12 C, 16 B plants and 12 A plants were analysed. Weak expression was observed in calli (66%) and in the discrimination centre/meristem (50%) of B plants. It was concluded that promoter PRO0133 is suitable for weak expression in meristem, preferably in shoot meristem or discrimination centre.

PRO0151—SEQ ID NO 16—WSI18

1 construct (OS1458) was investigated. 22 calli, 16 C, 16 B plants and 13 A plants were analysed. Strong expression was observed in calli (91%) and weak expression in shoots of C plants (62%). In A plants there was very strong expression in the aleurone layer and in the embryo (46%). It was concluded that promoter PRO0151 is suitable for strong expression in calli and in seeds, more particularly in the aleurone layer and in the embryo of the seeds.

PRO0169—SEQ ID NO 17—Aquaporine 1 construct (OS1911) was investigated. 11 calli, 10 C plants, B plants and A plants were analysed. Some expression (55%) was observed in calli and in roots (30%) of C plants. Furthermore, good expression was observed in shoot tissues (80%) of C plants and in young leaves of B plants. It was concluded that this promoter is suitable for constitutive expression, preferably constitutive in young plants.

PRO170—SEQ ID NO 18—High Mobility Group Protein 1 construct (OS1434) was investigated. 23 calli, 21 C, 21 B plants and 14 A plants were analysed. Expression was observed in calli (52%) and in roots (51%) of C plants. Moreover, strong expression was observed in young leaves (81%) of C plants, in roots (86%) of B plants and in young leaves (86%) of B plants. In A plants there was strong expression in young leaves (75%), old leaves (43%), embryo and aleurone but a weaker expression in endosperm (82%). It was concluded that promoter PRO170 is suitable for strong constitutive expression.

PRO0171—SEQ ID NO 19—Reversibly Glycosylated Protein RGP1

1 construct (OS1762) was investigated. 18 calli, 11 C and 13 B plants were analysed. Strong expression was observed in calli (44%) and in all tissues (27%) of C plants. In all tissues of B plants (16%), expression was somewhat weaker but most pronounced the in discrimination centres (46%). It was concluded that promoter PRO0171 is suitable for constitutive expression.

PRO0173—SEQ ID NO 20—Cytosolic MDH 1 construct (OS1435) was investigated. 17 calli, 17 C, 17 B plants and 15 A plants were analysed. Occasional expression (12%) was observed in calli and weak expression was observed in upper parts (24-69%) of C plants as well as in young leaves (41%) of B plants. In A plants, expression in leaves (33%) was observed and strong expression in seeds (38%), but not in the root. It was concluded that the promoter PRO0173 is suitable for expression in above-ground tissues especially for constitutive expression in the shoot and especially in the seeds.

PRO0175—SEQ ID NO 21—RAB21

1 construct (OS1436) was investigated. 16 calli, 12 C, 15 B plants and 15 A plants were analysed. Expression was observed in some calli (31%), in the discrimination centres (42%) of C plants and in young leaves (25-58%) of C plants and A plants (15%). Furthermore, very strong expression was observed in aleurone and embryo (60%) of a plant. It was concluded that promoter PRO0175 is suitable for strong expression in calli and in seeds, more particularly in developing/maturing seeds, more particularly in the aleurone layer and in the embryo of the seeds.

PRO0177—SEQ ID NO 22—Cdc2-1

1 construct (OS1436) was investigated. 16 calli, 12 C, 15 B plants and 15 A plants were analysed. Expression was observed in some of the calli (31%), in the discrimination centre (42%) of C plants, in young leaves (25-58%) of C plants and occasionally in young leaves (15%) of A plants. Moreover, very strong expression was observed in aleurone and embryo (60%) of seeds from A plants. It was concluded that this promoter is suitable for specific expression in seeds, more particularly in developing/maturing seeds.

Example 4

Stability of the Expression Patterns of the Promoters of the Present Invention in Further Generations The above-mentioned analyses were performed on T0 plants originating from the transformed tissues. The stability of promoter activity in the next generations or progeny plants of the original T0 plant, the so-called T1 and T2 plants, was evaluated as follows. The T0 plant transformed with the reporter constructs as mentioned in the above paragraphs of Example 2, were grown until maturity (A plants), of which the seeds (T1 seeds) were harvested and sown to generate progeny T1 plants. These plants were analysed as described above in Example 3 and the A T1 plants were allowed to reach maturity and to set T2 seeds.

The expression pattern of the promoters of the present invention was studied in T0 plants, T1 seeds, T1 plants and T2 seeds and in all the tissues (including seeds and seed tissues) as described in Example 3. The specific expression patterns as reported from the T0 and T1 seeds and described in Example 3 were confirmed in the following T1 generation and T2 seeds. It is concluded that the expression pattern of the promoters of the present are stably inherited in plants of subsequent generations.

Example 5

Stability of Expression Patterns of the Promoters of the Present Invention in Other Plants The above-mentioned plant analyses were performed on rice plants. This choice was based on the practical consideration that plant genetic engineering is most profitable for crop plants. Also in other crop plants, such as for example *Zea Mays*, the reporter constructs comprising the promoters according to the present invention are introduced and transformed plant are evaluated as described hereinabove. The expression patterns of the promoters according to the present invention are conserved among plants. Therefore, the promoters according to the present invention are also suitable for driving and/or regulating expression of an operably linked nucleic acid in monocots, such as corn.

For many other purposes such as research and horticulture, (small) herbs are being genetically modified, which involves the use of promoters. Therefore the reporter constructs comprising the promoters according to the present invention are introduced into other plants species such as for example *Arabidopsis thaliana* and transformed plants are evaluated as described hereinabove. The expression patterns of the promoters according to the present invention are conserved among plants. Therefore, the promoters according to the present invention are also suitable for driving and/or regulating expression of an operably linked nucleic acid in other plant species such as for example dicots, such as *Arabidopsis*.

What is claimed is:

1. A method for driving weak expression in young tissue of a nucleic acid in a plant, comprising introducing into a cell of a monocot or dicot plant a genetic construct comprising (a) an isolated promoter comprising an isolated nucleic acid comprising the sequence of SEQ ID NO: 5 and (b) a heterologous nucleic acid sequence operably linked to said isolated promoter; and optionally (c) a 3' transcription terminator, and testing and selecting a transgenic plant with weak expression in young tissue of said heterologous nucleic acid sequence.

2. The method according to claim 1, wherein after said introducing step and prior to said testing and selecting step, said cell of a monocot or dicot plant is cultivated under conditions promoting plant growth.

3. The method according to claim 1, wherein said cell of a monocot or dicot plant is selected from the group consisting of rice, maize, wheat, barley, millet, oats, rye, sorghum, soybean, sunflower, canola, sugarcane, alfalfa, bean, pea, flax, lupinus, rapeseed, tobacco, tomato, potato, squash, papaya, poplar and cotton.

* * * * *